United States Patent
Vakalopoulos et al.

(10) Patent No.: US 10,292,970 B2
(45) Date of Patent: May 21, 2019

(54) HETEROARYL-SUBSTITUTED IMIDAZO[1,2-A]PYRIDINES AND THEIR USE

(71) Applicant: BAYER PHARMA AKTIENGESELLSCHAFT, Berlin (DE)

(72) Inventors: Alexandros Vakalopoulos, Hilden (DE); Damian Brockschnieder, Haan (DE); Frank Wunder, Wuppertal (DE); Johannes-Peter Stasch, Grottaferrata (IT); Tobias Marquardt, Wuppertal (DE); Lisa Dietz, Wuppertal (DE); Volkhart Min-Jian Li, Velbert (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 15/531,948

(22) PCT Filed: Nov. 30, 2015

(86) PCT No.: PCT/EP2015/078009
§ 371 (c)(1),
(2) Date: May 31, 2017

(87) PCT Pub. No.: WO2016/087343
PCT Pub. Date: Jun. 9, 2016

(65) Prior Publication Data
US 2017/0304278 A1    Oct. 26, 2017

(30) Foreign Application Priority Data
Dec. 2, 2014   (EP) ..................... 14195902

(51) Int. Cl.
| | | |
|---|---|---|
| A61K 31/437 | (2006.01) | |
| C07D 471/04 | (2006.01) | |
| A61K 31/03 | (2006.01) | |
| B01J 31/14 | (2006.01) | |
| C07F 5/02 | (2006.01) | |

(52) U.S. Cl.
CPC ............ A61K 31/437 (2013.01); A61K 31/03 (2013.01); B01J 31/146 (2013.01); C07D 471/04 (2013.01); C07F 5/025 (2013.01)

(58) Field of Classification Search
CPC .................................................. A61K 31/437
USPC ....................................................... 514/300
See application file for complete search history.

(56) References Cited

U.S. PATENT DOCUMENTS

| | | |
|---|---|---|
| 5,593,993 A | 1/1997 | Morin, Jr. et al. |
| 5,691,336 A | 11/1997 | Dorn et al. |
| 5,698,704 A | 12/1997 | Jackson |
| 5,935,984 A | 8/1999 | Goldmann et al. |
| 6,180,656 B1 | 1/2001 | Furstner et al. |
| 6,403,588 B1 | 6/2002 | Hayakawa et al. |
| 7,173,037 B2 | 2/2007 | Alonso-Alija et al. |
| 8,129,423 B2 | 3/2012 | Ackermann et al. |
| 8,212,041 B2 | 7/2012 | Albrecht et al. |
| 8,314,112 B2 | 11/2012 | Leblanc et al. |
| 8,569,306 B2 | 10/2013 | Buettelmann et al. |
| 8,765,769 B2 | 7/2014 | Follmann et al. |
| 8,778,964 B2 | 7/2014 | Vakalopoulos et al. |
| 8,796,305 B2 | 8/2014 | Vakalopoulos et al. |
| 8,859,569 B2 | 10/2014 | Follmann et al. |
| 8,946,215 B2 | 2/2015 | Vakalopoulos et al. |
| 8,969,045 B2 | 3/2015 | Burkhardt et al. |
| 9,126,998 B2 | 9/2015 | Vakalopoulos et al. |
| 9,688,699 B2 | 6/2017 | Vakalopoulos et al. |
| 9,776,997 B2 * | 10/2017 | Vakalopoulos ...... C07D 471/04 |
| 2004/0176396 A1 | 9/2004 | Biftu et al. |
| 2004/0180896 A1 | 9/2004 | Munson et al. |
| 2005/0228004 A1 | 10/2005 | Gudmundsson et al. |
| 2006/0135517 A1 | 6/2006 | Lee et al. |
| 2008/0051409 A1 | 2/2008 | Gmeiner et al. |
| 2008/0103183 A1 | 5/2008 | Ackermann et al. |
| 2010/0063068 A1 | 3/2010 | Pracitto et al. |
| 2010/0130738 A1* | 5/2010 | Kohno ................. C07D 401/14 544/238 |
| 2012/0029002 A1 | 2/2012 | Straub et al. |
| 2013/0065884 A1 | 3/2013 | No et al. |
| 2013/0203751 A1 | 8/2013 | Hübsch et al. |
| 2014/0088080 A1 | 3/2014 | Koga et al. |
| 2014/0100229 A1 | 4/2014 | Follmann et al. |
| 2014/0128372 A1 | 5/2014 | Vakalopoulos et al. |
| 2014/0171434 A1 | 6/2014 | Follmann et al. |
| 2014/0179672 A1 | 6/2014 | Vakalopoulos et al. |
| 2014/0350020 A1 | 11/2014 | Follmann et al. |
| 2014/0357637 A1 | 12/2014 | Follmann et al. |
| 2015/0274719 A1 | 10/2015 | Vakalopoulos et al. |
| 2016/0122341 A1 | 5/2016 | Vakalopoulos et al. |
| 2016/0347770 A1 | 12/2016 | Vakalopoulos et al. |
| 2017/0050962 A1 | 2/2017 | Vakalopoulos et al. |

FOREIGN PATENT DOCUMENTS

| | | |
|---|---|---|
| CA | 2914100 A1 | 12/2014 |
| EP | 0266890 A1 | 5/1988 |

(Continued)

OTHER PUBLICATIONS

Wolf, Solid State Chemistry and Its Applications, john Wiley & Sons, 1984.*

(Continued)

*Primary Examiner* — Nizal S Chandrakumar
(74) *Attorney, Agent, or Firm* — Ice Miller LLP

(57) ABSTRACT

The present application relates to novel heteroaryl-substituted imidazo[1,2-a]pyridines, to processes for preparation thereof, to the use thereof, alone or in combinations, for the treatment and/or prophylaxis of diseases, and to the use thereof for production of medicaments for the treatment and/or prophylaxis of diseases, especially for the treatment and/or prophylaxis of cardiovascular disorders.

6 Claims, No Drawings

(56) References Cited

FOREIGN PATENT DOCUMENTS

| | | |
|---|---|---|
| EP | 1277754 A1 | 1/2003 |
| JP | 1-258674 A | 10/1989 |
| JP | 2003-313126 A | 11/2003 |
| WO | WO 89/03833 A1 | 5/1989 |
| WO | WO 96/34866 A1 | 11/1996 |
| WO | 98/16223 A1 | 4/1998 |
| WO | WO 98/16223 A1 | 4/1998 |
| WO | WO 2001/096335 A1 | 12/2001 |
| WO | 03/095451 A1 | 11/2003 |
| WO | WO 2005/58325 A1 | 6/2005 |
| WO | 2005/073205 A1 | 8/2005 |
| WO | WO 2005/90358 A2 | 9/2005 |
| WO | 2006/015737 A1 | 2/2006 |
| WO | WO 2006/015737 A1 | 2/2006 |
| WO | WO 2006/135667 A1 | 12/2006 |
| WO | WO 2007/2181 A2 | 1/2007 |
| WO | WO 2007/86800 A1 | 8/2007 |
| WO | 2008/008539 A2 | 1/2008 |
| WO | WO 2008/008539 A2 | 1/2008 |
| WO | 2008/032191 A2 | 3/2008 |
| WO | WO 2008/061626 A1 | 5/2008 |
| WO | WO 2008/082490 A2 | 7/2008 |
| WO | WO 2008/88881 A1 | 7/2008 |
| WO | WO 2008/134553 A1 | 11/2008 |
| WO | 2008/148867 A2 | 12/2008 |
| WO | 2009/155527 A2 | 12/2009 |
| WO | 2010/030538 A2 | 3/2010 |
| WO | WO 2010/030538 A2 | 3/2010 |
| WO | WO 2010/57833 A1 | 5/2010 |
| WO | 2010/065275 A1 | 6/2010 |
| WO | 2010/079120 A1 | 7/2010 |
| WO | 2010/101949 A1 | 9/2010 |
| WO | 2010/125102 A1 | 11/2010 |
| WO | 2010/136971 A1 | 12/2010 |
| WO | 2011/088045 A1 | 7/2011 |
| WO | WO 2011/113606 A1 | 9/2011 |
| WO | 2011/141409 A1 | 11/2011 |
| WO | 2011/149921 A1 | 12/2011 |
| WO | 2012/004258 A1 | 1/2012 |
| WO | 2012/004259 A1 | 1/2012 |
| WO | 2012/006760 A1 | 1/2012 |
| WO | 2012/143510 A1 | 10/2012 |
| WO | 2012/143796 A2 | 10/2012 |
| WO | 2012/152629 A1 | 11/2012 |
| WO | WO 2012/165399 A1 | 12/2012 |
| WO | 2013/030288 A1 | 3/2013 |
| WO | 2013/104703 A1 | 7/2013 |
| WO | WO 2014/068099 A1 | 5/2014 |
| WO | WO 2014/195333 A1 | 12/2014 |
| WO | 2015/082411 A1 | 6/2015 |
| WO | 2015/124544 A1 | 8/2015 |
| WO | 2015/140199 A1 | 9/2015 |
| WO | 2015/140254 A1 | 9/2015 |

OTHER PUBLICATIONS

International Search Report (PCT/ISA/210) dated Jan. 25, 2016, by the European Patent Office as the International Searching Authority for International Application No. PCT/EP2015/078009.
Written Opinion (PCT/ISA/237) dated Jan. 25, 2016, by the European Patent Office as the International Searching Authority for International Application No. PCT/EP2015/078009.
Cui et al., "Structure Based Drug Design of Crizotinib (PF-02341066), a Potent and Selective Dual Inhibitor of Mesenchymal-Epithelial Transition Factor (c-MET) Kinase and Anaplastic Lymphoma Kinase (ALK)", Journal of Medicinal Chemistry, vol. 54, (2011) pp. 6342-6363.
Goldberg et al., "Stimulation of Human Platelet Guanylate Cyclase by Fatty Acids", The Journal of Biological Chemistry, vol. 252, No. 4, 1977, pp. 1279-1285.
Hamill et al., "Improved Patch-Clamp Techniques for High-Resolution Current Recording from Cells and Cell-Free Membrane Patches", Pflügers Archiv, vol. 391, 1981, pp. 85-100.
Hassan et al., "Aryl-Aryl Bond Formation One Century after the Discovery of the Ullmann Reaction", Chem. Rev. 2002, vol. 102, pp. 1359-1469.
Himmel, "Suitability of commonly used excipients for electrophysiological in-vitro safety pharmacology assessment of effects on hERG potassium current and on rabbit Purkinje fiber action potential", Journal of Pharmacological and Toxicological Methods, 2007, vol. 56, pp. 145-158.
Hoenicka et al., "Purified soluble guanylyl cyclase expressed in a baculovirus/Sf9 system: stimulation by YC-1, nitric oxide, and carbon monoxide", J. Mol. Med., 1999, Bd. 77, pp. 14-23.
Mülsch et al., "Effect of YC-1, an NO-independent, superoxide-sensitive stimulator of soluble guanylyl cyclase, on smooth muscle responsiveness to nitrovasodilators", British Journal of Pharmacology, 1997, 120, pp. 681-689.
Palmer et al., "Synthesis and Evaluation of 7H-8,9-Dihydropyrano[2,3-c]imidazo[1,2-α]pyridines as Potassium-Competitive Acid Blockers", J. Med. Chem. 2007, vol. 50, pp. 6240-6264.
Pettibone et al., "A Structurally Novel Stimulator of Guanylate Cyclase With Long-Lasting Hypotensive Activity in the Dog", European Journal of Pharmacology, 1985, Bd. 116, pp. 307-312.
Scheel et al., "Introduction of a Modular Automated Voltage-Clamp Platform and Its Correlation with Manual Human Ether-à-go-go Related Gene Voltage-Clamp Data", Assay Drug Dev Technol 2011, vol. 9, pp. 600-607.
Stasch et al., "Cardiovascular actions of a novel NO-independent guanylyl cyclase stimulator, BAY 41-8543: in vivo studies", British Journal of Pharmacology, 2002, vol. 135, No. 2, pp. 344-355.
Weidmann et al., "2-[(2-Pyridylmethyl)sulfinyl]-1H-thieno[3,4-d]imidazole. A Novel Class of Gastric $H^+/K^+$-ATPase Inhibitors", Journal of Medicinal Chemistry, 1992, 35, pp. 438-450.
Wu et al., "YC-1, a novel activator of platelet guanylate cyclase", Blood, 1994, vol. 84, pp. 4226-4233.
Wunder et al., "A cell-based cGMP assay useful for ultra-high-throughput screening and identification of modulators of the nitric oxide/cGMP pathway", Analytical Biochemistry, 2005, vol. 339, pp. 104-112.
Yu et al., "Vasorelaxant effect of isoliquiritigenin, a novel soluble guanylate cyclase activator, in rat aorta", British Journal of Pharmacology, 1995, 114, pp. 1587-1594.
Zhou et al., "Properties of HERG Channels Stably Expressed in HEK 293 Cells Studied at Physiological Temperature", Biophysical Journal, vol. 74, 1998, pp. 230-241.
Albersen et al., "Synergistic Effects of BAY 60/4552 and Vardenafil on Relaxation of Corpus Cavernosum Tissue of Patients with Erectile Dysfunction and Clinical Phosphodiesterase Type 5 Inhibitor Failure," The Journal of Sexual Medicine, (May 2013), vol. 10, Issue 5, pp. 1268-1277.
Bitler et al., "The Preparation and Properties of Crystalline Firefly Luciferin," Archives of Biochemistry and Biophysics, (1957), vol. 72, No. 2, pp. 358-368.
Bodanszky et al., "The Practice of Peptide Synthesis," Second, Revised Edition, Springer-Verlag Berlin Heidelberg 1994, pp. 1-24.
Chen et al., "Cyclic Guanosine Monophosphate Signalling Pathway in Pulmonary Arterial Hypertension," Vascular Pharmacology, (Mar. 2013), vol. 58, Issue 3, pp. 211-218.
Daley et al., "The First Complete Identification of a Diastereomeric Catalyst-Substrate (Alkoxide) Species in an Enantioselective Ketone Hydrogenation. Mechanistic Investigations," Journal of the American Chemical Society, (2002), vol. 124, No. 14, pp. 3680-3691.
Dembinski, "Recent Advances in the Mitsunobu Reaction: Modified Reagents and the Quest for Chromatography-Free Separation," European Journal of Organic Chemistry, (Jul. 2004), vol. 2004, Issue 13, pp. 2763-2772.
Deng et al., "Studies on Phosphoroheterocycle Chemistry II: A Simple and New Route to 1,3,2-Diazaphospholidine-4-thione 2-sulfide Derivatives," Synthesis, (2001), No. 16, pp. 2445-2449.
Evgenov et al., "NO-Independent Stimulators and Activators of Soluble Guanylate Cyclase: Discovery and Therapeutic Potential," Nature Reviews Drug Discovery, (2006), vol. 5, No. 9, pp. 755-768.
Florentin et al., "Etude des pKa et de la Protodéboronation des Acides Furanneboroniques," Journal of Heterocyclic Chemistry, (Dec. 1976), vol. 13, Issue 6, pp. 1265-1272.

(56) References Cited

OTHER PUBLICATIONS

Gensini et al., "3-Azabicyclo[3.1.0]hex-1-ylamines by Ti-Mediated Intramolecular Reductive Cyclopropanation of α-(N-Allylamino)-Substituted N,N-Dialkylcarboxamides and Carbonitriles," European Journal of Organic Chemistry, (2002), vol. 2002, No. 15, pp. 2499-2507.

Gheorghiade et al., "Soluble Guanylate Cyclase: A Potential Therapeutic Target for Heart Failure," Heart Failure Reviews (Mar. 2013), vol. 18, Issue 2, pp. 123-134.

Greene et al., "The Role of Protective Groups in Organic Synthesis," Greene's Protective Groups in Organic Synthesis, Fourth Edition, (2007), pp. 1-15.

Hjørringgaard et al., "An Automatic Solid-Phase Synthesis of Peptaibols," The Journal of Organic Chemistry, (2009), vol. 74, No. 3, pp. 1329-1332.

Hughes, "The Mitsunobu Reaction," Organic Reactions, (1992), vol. 42, Chapter 2, Published by John Wiley & Sons, Inc., pp. 335-395 and 636-656.

Kozo et al., "Spontaneous Hypertension in Rats," Int Rev. Exp. Pathol, (1969), vol. 7, pp. 227-270.

Lasker et al., "Targeting Soluble Guanylate Cyclase for the Treatment of Pulmonary Hypertension," Expert Review of Respiratory Medicine, (Apr. 2011), vol. 5, Issue 2, pp. 153-161.

Mittendorf et al., "Discovery of Riociguat (BAY 63/2521): A Potent, Oral Stimulator of Soluble Guanylate Cyclase for the Treatment of Pulmonary Hypertension," ChemMedChem, (May 2009), vol. 4, No. 5, pp. 853-865.

Ogrel et al., "Synthesis of 15N-Labelled D-Isovaline and α-Aminoisobutyric Acid," European Journal of Organic Chemistry, (Mar. 2000), vol. 2000, Issue 5, pp. 857-859.

Oudot et al., "Combination of BAY 60/4552 and Vardenafil Exerts Proerectile Facilitator Effects in Rats With Cavernous Nerve Injury: A Proof of Concept Study for the Treatment of Phosphodiesterase Type 5 Inhibitor Failure," European Urology, (2011), vol. 60, No. 5, pp. 1020-1026.

Patani et a., "Bioisosterism: A Rational Approach in Drug Design," Chemical Reviews, (1996), vol. 96, No. 8, pp. 3147-3176.

Sharkovska et al., "Nitric Oxide-Independent Stimulation of Soluble Guanylate Cyclase Reduces Organ Damage in Experimental Low-Renin and High-Renin Models," Journal of Hypertension, (2010), vol. 28, No. 8, pp. 1666-1675.

Soler et al., "Betulinic Acid Derivatives: A New Class of Specific Inhibitors of Human Immunodeficiency Virus Type 1 Entry," Journal of Medicinal Chemistry, (1996), vol. 39, Issue 5, pp. 1069-1083.

Stasch et al., "Pharmacological Actions of a Novel NO-Independent Guanylyl Cyclase Stimulator, BAY 41-8543: in vitro Studies," British Journal of Pharmacology, (2002), vol. 135, No. 2, pp. 333-343.

Stasch et al., "Soluble Guanylate Cyclase as an Emerging Therapeutic Target in Cardiopulmonary Disease," Circulation, (2011), vol. 123, No. 20, pp. 2263-2273.

Van Den Buuse, "Circadian Rhythms of Blood Pressure, Heart Rate, and Locomotor Activity in Spontaneously Hypertensive Rats as Measured with Radio-Telemetry," Physiology & Behavior, (Apr. 1994), vol. 55, Issue 4, pp. 783-787.

Wermuth, "Molecular Variations Based on Isosteric Replacements," The Practice of Medical Chemistry, (1996), pp. 203-237.

Witte et al., "Experimental heart failure in rats: effects on cardiovascular circadian rhythms and on myocardial β-adrenergic signaling," Cardiovascular Research, (Aug. 2000), vol. 47, No. 2, pp. 350-358.

\* cited by examiner

HETEROARYL-SUBSTITUTED IMIDAZO[1,2-A]PYRIDINES AND THEIR USE

The present application relates to novel heteroaryl-substituted imidazo[1,2-a]pyridines, to processes for preparation thereof, to the use thereof, alone or in combinations, for the treatment and/or prophylaxis of diseases, and to the use thereof for production of medicaments for the treatment and/or prophylaxis of diseases, especially for the treatment and/or prophylaxis of cardiovascular disorders.

One of the most important cellular transmission systems in mammalian cells is cyclic guanosine monophosphate (cGMP). Together with nitrogen monoxide (NO), which is released from the endothelium and transmits hormonal and mechanical signals, it forms the NO/cGMP system. Guanylate cyclases catalyse the biosynthesis of cGMP from guanosine triphosphate (GTP). The representatives of this family known to date can be classified into two groups either by structural features or by the type of ligands: the particulate guanylate cyclases which can be stimulated by natriuretic peptides, and the soluble guanylate cyclases which can be stimulated by NO. The soluble guanylate cyclases consist of two subunits and very probably contain one heme per heterodimer, which is part of the regulatory centre. This is of central importance for the activation mechanism. NO is able to bind to the iron atom of heme and thus markedly increase the activity of the enzyme. Heme-free preparations cannot, by contrast, be stimulated by NO. Carbon monoxide (CO) is also able to bind to the central iron atom of heme, but the stimulation by CO is much less than that by NO.

By forming cGMP, and owing to the resulting regulation of phosphodiesterases, ion channels and protein kinases, guanylate cyclase plays an important role in various physiological processes, in particular in the relaxation and proliferation of smooth muscle cells, in platelet aggregation and platelet adhesion and in neuronal signal transmission, and also in disorders which are based on a disruption of the aforementioned processes. Under pathophysiological conditions, the NO/cGMP system can be suppressed, which can lead, for example, to hypertension, platelet activation, increased cell proliferation, endothelial dysfunction, atherosclerosis, angina pectoris, heart failure, myocardial infarction, thromboses, stroke and sexual dysfunction.

Owing to the expected high efficiency and low level of side effects, a possible NO—independent treatment for such disorders by targeting the influence of the cGMP signal pathway in organisms is a promising approach.

Hitherto, for the therapeutic stimulation of the soluble guanylate cyclase, use has exclusively been made of compounds such as organic nitrates whose effect is based on NO. The latter is formed by bioconversion and activates soluble guanylate cyclase by attacking the central iron atom of heme. In addition to the side effects, the development of tolerance is one of the crucial disadvantages of this mode of treatment.

In recent years, some substances have been described which stimulate soluble guanylate cyclase directly, i.e. without prior release of NO, such as, for example, 3-(5'-hydroxymethyl-2'-furyl)-1-benzylindazole [YC-1; Wu et al., Blood 84 (1994), 4226; Mtilsch et al., Brit. J. Pharmacol. 120 (1997), 681], fatty acids [Goldberg et al., J. Biol. Chem. 252 (1977), 1279], diphenyliodonium hexafluorophosphate [Pettibone et al., Eur. J. Pharmacol. 116 (1985), 307], isoliquiritigenin [Yu et al., Brit. J. Pharmacol. 114 (1995), 1587] and various substituted pyrazole derivatives (WO 98/16223).

Various imidazo[1,2-a]pyridine derivatives which can be used for treating disorders are described, inter alia, in EP 0 266 890-A1, WO 89/03833-A1, JP 01258674-A [cf. Chem. Abstr. 112:178986], WO 96/34866-A1, EP 1 277 754-A1, WO 2001/096335, WO 2006/015737-A1, WO 2006/135667, WO 2008/008539-A2, WO 2008/082490-A2, WO 2008/134553-A1, WO 2010/030538-A2, WO 2011/113606-A1 and WO 2012/165399-A1.

It was an object of the present invention to provide novel substances which act as stimulators of soluble guanylate cyclase and are suitable as such for the treatment and/or prophylaxis of diseases.

The present invention provides compounds of the general formula (I)

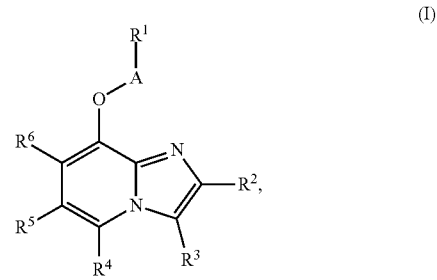

in which
A represents $CH_2$, $CD_2$ or $CH(CH_3)$,
$R^1$ represents $(C_3-C_7)$-cycloalkyl, phenyl or pyridyl,
  where $(C_3-C_7)$-cycloalkyl may be substituted by 1 to 4 substituents independently of one another selected from the group consisting of fluorine, trifluoromethyl and $(C_1-C_4)$-alkyl,
  where phenyl is substituted by 1 to 4 substituents independently of one another selected from the group consisting of halogen, cyano, monofluoromethyl, difluoromethyl, trifluoromethyl, $(C_1-C_4)$-alkyl, $(C_1-C_4)$-alkoxy and difluoromethoxy
  and
  where pyridyl is substituted by 1 or 2 substituents independently of one another selected from the group consisting of halogen, cyano and $(C_1-C_4)$-alkyl,
$R^2$ represents $(C_1-C_4)$-alkyl, cyclopropyl, cyclobutyl, monofluoromethyl, difluoromethyl or trifluoromethyl,
$R^3$ represents phenyl or 6-membered heteroaryl,
  where phenyl is substituted by —$NR^7R^8$,
  in which
    $R^7$ represents hydrogen or $(C_1-C_4)$-alkyl,
    $R^8$ represents $(C_1-C_6)$-alkyl or $(C_1-C_4)$-alkylcarbonyl,
      in which $(C_1-C_6)$-alkyl may be substituted by amino and up to three times by fluorine,
    or
    $R^7$ and $R^8$ together with the nitrogen atom to which they are attached form a 4- to 6-membered heterocycle,
  where phenyl may be substituted by 1 or 2 substituents independently of one another selected from the group consisting of fluorine, chlorine, bromine, methyl and ethyl,
  where 6-membered heteroaryl is up to disubstituted by —$NR^9R^{10}$,
    in which
    $R^9$ represents hydrogen or $(C_1-C_4)$-alkyl,
    $R^{10}$ represents hydrogen, $(C_1-C_6)$-alkyl, phenyl or $(C_1-C_4)$-alkylcarbonyl, in which ($C_1$-$C_6$)-alkyl may be substituted by 1 or 2 substituents independently of one another selected from the group consisting of ($C_1$-$C_4$)-alkoxy, amino and phenyl, and up to pentasubstituted by fluorine, or $R^9$ and $R^{10}$ together with the nitrogen atom to which they are attached form a 4- to 6-membered heterocycle, in which the 4- to 6-membered heterocycle may be substituted by 1 or 2 ($C_1$-$C_4$)-alkyl substituents, where 6-membered heteroaryl may be substituted by 1 or 2 substituents independently of one another selected from the group consisting of fluorine, chlorine, bromine, cyclopropyl, methyl and ethyl, $R^4$ represents hydrogen, $R^5$ represents hydrogen, fluorine, chlorine, cyano, ($C_1$-$C_4$)-alkyl, cyclopropyl, difluoromethyl or trifluoromethyl, $R^6$ represents hydrogen or fluorine, and the N-oxides, salts, solvates, salts of the N-oxides and solvates of the N-oxides and salts thereof.

Except for the Compounds

N-(3-{8-[(2,6-difluorobenzyl)oxy]-2-methylimidazo[1,2-a]pyridin-3-yl}phenyl)acetamide, 8-[(2,6-difluorobenzyl)oxy]-2-methyl-3-[3-(piperidin-1-yl)phenyl]imidazo[1,2-a]pyridine.

Compounds of the invention are the compounds of the formula (I) and the salts, solvates and solvates of the salts thereof, the compounds that are encompassed by formula (I) and are of the formulae mentioned below and the salts, solvates and solvates of the salts thereof and the compounds that are encompassed by formula (I) and are cited below as working examples and the salts, solvates and solvates of the salts thereof if the compounds that are encompassed by formula (I) and are mentioned below are not already salts, solvates and solvates of the salts.

Preferred salts in the context of the present invention are physiologically acceptable salts of the compounds according to the invention. Also encompassed are salts which are not themselves suitable for pharmaceutical applications but can be used, for example, for isolation or purification of the compounds according to the invention.

Physiologically acceptable salts of the compounds of the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, formic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates in the context of the invention are described as those forms of the compounds according to the invention which form a complex in the solid or liquid state by coordination with solvent molecules. Hydrates are a specific form of the solvates in which the coordination is with water. Solvates preferred in the context of the present invention are hydrates.

The compounds of the invention may, depending on their structure, exist in different stereoisomeric forms, i.e. in the form of configurational isomers or else, if appropriate, as conformational isomers (enantiomers and/or diastereomers, including those in the case of atropisomers). The present invention therefore encompasses the enantiomers and diastereomers, and the respective mixtures thereof. The stereoisomerically homogeneous constituents can be isolated from such mixtures of enantiomers and/or diastereomers in a known manner; chromatographic processes are preferably used for this purpose, especially HPLC chromatography on an achiral or chiral phase.

If the compounds according to the invention can occur in tautomeric forms, the present invention encompasses all the tautomeric forms.

The present invention also encompasses all suitable isotopic variants of the compounds according to the invention. An isotopic variant of a compound of the invention is understood here to mean a compound in which at least one atom within the compound of the invention has been exchanged for another atom of the same atomic number, but with a different atomic mass from the atomic mass which usually or predominantly occurs in nature. Examples of isotopes which can be incorporated into a compound of the invention are those of hydrogen, carbon, nitrogen, oxygen, phosphorus, sulfur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of a compound according to the invention, especially those in which one or more radioactive isotopes have been incorporated, may be beneficial, for example, for the examination of the mechanism of action or of the active ingredient distribution in the body; due to the comparatively easy preparability and detectability, especially compounds labelled with $^3$H or $^{14}$C isotopes are suitable for this purpose. In addition, the incorporation of isotopes, for example of deuterium, may lead to particular therapeutic benefits as a consequence of greater metabolic stability of the compound, for example an extension of the half-life in the body or a reduction in the active dose required; such modifications of the compounds according to the invention may therefore in some cases also constitute a preferred embodiment of the present invention. Isotopic variants of the compounds of the invention can be prepared by the processes known to those skilled in the art, for example by the methods described further down and the procedures described in the working examples, by using corresponding isotopic modifications of the respective reagents and/or starting materials.

The present invention additionally also encompasses prodrugs of the compounds according to the invention. The term "prodrugs" in this context refers to compounds which may themselves be biologically active or inactive but are reacted (for example metabolically or hydrolytically) to give compounds according to the invention during their residence time in the body.

In the context of the present invention, unless specified otherwise, the substituents are defined as follows:

Alkyl in the context of the invention is a straight-chain or branched alkyl radical having the particular number of carbon atoms specified. By way of example and with preference, mention may be made of the following: methyl, ethyl, n-propyl, isopropyl, n-butyl, isobutyl, 1-methylpropyl, tert-butyl, n-pentyl, isopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl, 2-ethylbutyl.

Cycloalkyl or carbocycle in the context of the invention represents a monocyclic saturated alkyl radical having the particular number of ring carbon atoms specified. By way of example and with preference, mention may be made of the following: cyclopropyl, cyclobutyl, cyclopentyl, cyclohexyl and cycloheptyl.

Alkoxy in the context of the invention is a straight-chain or branched alkoxy radical having 1 to 4 carbon atoms. By way of example and with preference, mention may be made of the following: methoxy, ethoxy, n-propoxy, isopropoxy, 1-methylpropoxy, n-butoxy, isobutoxy and tert-butoxy.

Alkoxycarbonyl in the context of the invention is a straight-chain or branched alkoxy radical having 1 to 4 carbon atoms and a carbonyl group attached to the oxygen atom. By way of example and with preference, mention may be made of the following: methoxycarbonyl, ethoxycarbonyl, n-propoxycarbonyl, isopropoxycarbonyl and tert-butoxycarbonyl.

Heterocycle or heterocyclyl in the context of the invention is a monocyclic saturated heterocycle which has a total of 4 to 7 ring atoms, contains one or two ring heteroatoms from the group consisting of N, O, S, SO and $SO_2$ and is attached via a ring carbon atom or, where appropriate, a ring nitrogen atom. The following may be mentioned by way of example: azetidinyl, oxetanyl, pyrrolidinyl, pyrazolidinyl, tetrahydrofuranyl, thiolanyl, piperidinyl, piperazinyl, tetrahydropyranyl, tetrahydrothiopyranyl, morpholinyl, thiomorpholinyl, hexahydroazepinyl and hexahydro-1,4-diazepinyl. Preference is given to azetidinyl, oxetanyl, pyrrolidinyl, tetrahydrofuranyl, piperidinyl, piperazinyl, tetrahydropyranyl and morpholinyl.

Heteroaryl in the context of the invention represents a monocyclic aromatic heterocycle (heteroaromatic) which has a total of 5 to 10 ring atoms, contains up to three identical or different ring heteroatoms from the group of N, O and/or S and is attached via a ring carbon atom or optionally via a ring nitrogen atom. By way of example and with preference, mention may be made of the following: furyl, pyrrolyl, thienyl, 1H-pyrazol-4-yl, 1H-pyrazol-5-yl, imidazolyl, 1,3-thiazol-5-yl, 1,3-thiazol-2-yl, 1,3-oxazol-5-yl, 1,3-oxazol-2-yl, isoxazolyl, isothiazolyl, triazolyl, 1,3,4-oxadiazol-2-yl, 1,2,4-oxadiazol-3-yl, 1,2,4-oxadiazol-5-yl, 1,3,4-thiadiazol-2-yl, 1,2,4-thiadiazol-3-yl, 1,2,4-thiadiazol-5-yl, pyridyl, pyrimidinyl, pyridazinyl, pyrazinyl and triazinyl.

Halogen in the context of the invention includes fluorine, chlorine, bromine and iodine. Preference is given to chlorine or fluorine.

In the formula of the group that $R^1$ may represent, the end point of the line marked by the symbol # or ## does not represent a carbon atom or a $CH_2$ group but is part of the bond to the respectively marked atom to which $R^1$ is attached.

When radicals in the compounds according to the invention are substituted, the radicals may be mono- or polysubstituted, unless specified otherwise. In the context of the present invention, all radicals which occur more than once are defined independently of one another. Substitution by one, two or three identical or different substituents is preferred.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

In the context of the present invention, preference is given to compounds of the formula (I) in which A represents $CH_2$, $R^1$ represents cyclohexyl, phenyl or pyridyl,
    where phenyl is substituted by 1 to 4 substituents independently of one another selected from the group consisting of fluorine, chlorine, cyano and methyl,
    and
    where pyridyl is substituted by 1 or 2 fluorine substituents, $R^2$ represents methyl, cyclopropyl or trifluoromethyl, $R^3$ represents phenyl, 3-pyridyl, 4-pyridyl, 2-pyrimidyl, 5-pyrimidyl or 1,3,5-triazinyl,
    where phenyl is substituted in the 3-position by $-NR^7R^8$,
    in which
        $R^7$ represents hydrogen,
        $R^8$ represents methyl, ethyl, methylcarbonyl or ethylcarbonyl,
        or
        $R^7$ and $R^8$ together with the nitrogen atom to which they are attached form a 5- or 6-membered heterocycle,
    where phenyl may be substituted by 1 or 2 substituents independently of one another selected from the group consisting of fluorine and chlorine,
    where 3-pyridyl, 4-pyridyl, 2-pyrimidyl and 5-pyrimidyl are substituted by $-NR^9R^{10}$,
    in which
        $R^9$ represents hydrogen or methyl,
        $R^{10}$ represents $(C_1-C_6)$-alkyl or phenyl,
            in which $(C_1-C_6)$-alkyl may be substituted by 1 or 2 substituents independently of one another selected from the group consisting of $(C_1-C_4)$-alkoxy, amino and phenyl, and up to trisubstituted by fluorine,
        or
        $R^9$ and $R^{10}$ together with the nitrogen atom to which they are attached form a 5- or 6-membered heterocycle,
            in which the 5- or 6-membered heterocycle may be substituted by 1 or 2 methyl substituents,
    where 3-pyridyl, 4-pyridyl, 2-pyrimidyl and 5-pyrimidyl may be substituted by 1 or 2 substituents independently of one another selected from the group consisting of fluorine, chlorine and methyl,
    where 1,3,5-triazinyl is up to disubstituted by $-NR^{9A}R^{10A}$,
    in which
        $R^{9A}$ represents hydrogen or methyl,
        $R^{10A}$ represents hydrogen, $(C_1-C_6)$-alkyl or phenyl,
            in which $(C_1-C_6)$-alkyl may be substituted by amino and up to three times by fluorine,
        or $R^{9A}$ and $R^{10A}$ together with the nitrogen atom to which they are attached form a 5- or 6-membered heterocycle,
in which the 5- or 6-membered heterocycle may be substituted by 1 or 2 methyl substituents,
where 1,3,5-triazinyl may be substituted by chlorine,
$R^4$ represents hydrogen,
$R^5$ represents hydrogen, chlorine, methyl or cyclopropyl,
$R^6$ represents hydrogen,
and the N-oxides, salts, solvates, salts of the N-oxides and solvates of the N-oxides and salts thereof.
Except for the Compounds
N-(3-{8-[(2,6-difluorobenzyl)oxy]-2-methylimidazo[1,2-a]pyridin-3-yl}phenyl)acetamide,
8-[(2,6-difluorobenzyl)oxy]-2-methyl-3-[3-(piperidin-1-yl)phenyl]imidazo[1,2-a]pyridine.
In the context of the present invention, preference is given to compounds of the formula (I) in which
A represents $CH_2$,
$R^1$ represents cyclohexyl, phenyl or pyridyl,
where phenyl is substituted by 1 to 3 fluorine substituents,
where pyridyl is substituted by 1 fluorine substituent,
$R^2$ represents methyl,
$R^3$ represents phenyl, 3-pyridyl, 4-pyridyl, 2-pyrimidyl, 5-pyrimidyl or 1,3,5-triazinyl,
where phenyl is substituted in the 3-position by —$NR^7R^8$,
in which
$R^7$ represents hydrogen,
$R^8$ represents methyl, ethyl, methylcarbonyl or ethylcarbonyl,
or
$R^7$ and $R^8$ together with the nitrogen atom to which they are attached form a 5- or 6-membered heterocycle,
where 3-pyridyl, 4-pyridyl, 2-pyrimidyl and 5-pyrimidyl are substituted by —$NR^9R^{10}$,
in which
$R^9$ represents hydrogen or methyl,
$R^{10}$ represents $(C_1-C_6)$-alkyl or phenyl,
in which $(C_1-C_6)$-alkyl may be substituted by 1 or 2 substituents independently of one another selected from the group consisting of $(C_1-C_4)$-alkoxy, amino and phenyl, and up to trisubstituted by fluorine,
or
$R^9$ and $R^{10}$ together with the nitrogen atom to which they are attached form a 5- or 6-membered heterocycle,
in which the 5- or 6-membered heterocycle may be substituted by 1 or 2 methyl substituents,
where 3-pyridyl, 4-pyridyl, 2-pyrimidyl and 5-pyrimidyl may be substituted by 1 or 2 substituents independently of one another selected from the group consisting of fluorine, chlorine and methyl,
where 1,3,5-triazinyl is up to disubstituted by —$NR^{9A}R^{10A}$,
in which
$R^{9A}$ represents hydrogen or methyl,
$R^{10A}$ represents hydrogen, $(C_1-C_6)$-alkyl or phenyl,
in which $(C_1-C_6)$-alkyl may be substituted by amino and up to three times by fluorine,
where 1,3,5-triazinyl may be substituted by chlorine,
$R^4$ represents hydrogen,
$R^5$ represents hydrogen, chlorine, methyl or cyclopropyl,
$R^6$ represents hydrogen,
and the N-oxides, salts, solvates, salts of the N-oxides and solvates of the N-oxides and salts thereof.
Except for the Compounds
N-(3-{8-[(2,6-difluorobenzyl)oxy]-2-methylimidazo[1,2-a]pyridin-3-yl}phenyl)acetamide,
8-[(2,6-difluorobenzyl)oxy]-2-methyl-3-[3-(piperidin-1-yl)phenyl]imidazo[1,2-a]pyridine.
In the context of the present invention, preference is given to compounds of the formula (I) in which
A represents $CH_2$,
$R^1$ represents cyclohexyl, phenyl or pyridyl,
where phenyl is substituted by 1 to 3 fluorine substituents,
$R^2$ represents methyl,
$R^3$ represents phenyl, 3-pyridyl, 4-pyridyl, 2-pyrimidyl, 5-pyrimidyl or 1,3,5-triazinyl,
where phenyl is substituted in the 3-position by —$NR^7R^8$,
in which
$R^7$ represents hydrogen,
$R^8$ represents methyl, ethyl, methylcarbonyl or ethylcarbonyl,
or
$R^7$ and $R^8$ together with the nitrogen atom to which they are attached form a 5- or 6-membered heterocycle,
where 3-pyridyl, 4-pyridyl, 2-pyrimidyl and 5-pyrimidyl are substituted by —$NR^9R^{10}$,
in which
$R^9$ represents hydrogen or methyl,
$R^{10}$ represents $(C_1-C_6)$-alkyl or phenyl,
in which $(C_1-C_6)$-alkyl may be substituted by 1 or 2 substituents independently of one another selected from the group consisting of $(C_1-C_4)$-alkoxy, amino and phenyl, and up to trisubstituted by fluorine,
or
$R^9$ and $R^{10}$ together with the nitrogen atom to which they are attached form a 5- or 6-membered heterocycle,
in which the 5- or 6-membered heterocycle may be substituted by 1 or 2 methyl substituents,
where 3-pyridyl, 4-pyridyl, 2-pyrimidyl and 5-pyrimidyl may be substituted by 1 or 2 substituents independently of one another selected from the group consisting of fluorine, chlorine and methyl,
where 1,3,5-triazinyl is up to disubstituted by —$NR^{9A}R^{10A}$,
in which
$R^{9A}$ represents hydrogen or methyl,
$R^{10A}$ represents hydrogen, $(C_1-C_6)$-alkyl or phenyl,
in which $(C_1-C_6)$-alkyl may be substituted by amino and up to three times by fluorine,
where 1,3,5-triazinyl may be substituted by chlorine,
$R^4$ represents hydrogen,
$R^5$ represents hydrogen, chlorine, methyl or cyclopropyl,
$R^6$ represents hydrogen,
and the N-oxides, salts, solvates, salts of the N-oxides and solvates of the N-oxides and salts thereof.
Except for the Compounds
N-(3-{8-[(2,6-difluorobenzyl)oxy]-2-methylimidazo[1,2-a]pyridin-3-yl}phenyl)acetamide,
8-[(2,6-difluorobenzyl)oxy]-2-methyl-3-[3-(piperidin-1-yl)phenyl]imidazo[1,2-a]pyridine.
Particular preference is given in the context of the present invention to compounds of the formula (I) in which
A represents $CH_2$,
$R^1$ represents cyclohexyl,
or represents a phenyl group of the formula

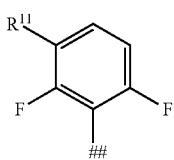

where
represents the point of attachment to A,
and
$R^{11}$ represents hydrogen or fluorine,
or
represents a pyridyl group of the formula

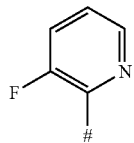

where
\# represents the point of attachment to A,
$R^2$ represents methyl,
$R^3$ represents phenyl, 3-pyridyl, 4-pyridyl, 2-pyrimidyl, 5-pyrimidyl or 1,3,5-triazinyl,
 where phenyl is substituted in the 3-position by —$NR^7R^8$,
  in which
  $R^7$ represents hydrogen,
  $R^8$ represents methylcarbonyl,
  or
  $R^7$ and $R^8$ together with the nitrogen atom to which they are attached form a pyrrolidinyl ring,
 where 3-pyridyl is substituted in the 4-position by —$NR^9R^{10}$,
 where 4-pyridyl is substituted in the 3-position by —$NR^9R^{10}$,
 where 2-pyrimidyl is substituted in the 4-position by —$NR^9R^{10}$,
 where 5-pyrimidyl is substituted in the 2-position by —$NR^9R^{10}$,
  in which in each case
  $R^9$ represents hydrogen or methyl,
  $R^{10}$ represents $(C_1-C_6)$-alkyl or phenyl,
   in which $(C_1-C_6)$-alkyl may be substituted by 1 or 2 substituents independently of one another selected from the group consisting of $(C_1-C_4)$-alkoxy, amino and phenyl, and up to trisubstituted by fluorine,
  or
  $R^9$ and $R^{10}$ together with the nitrogen atom to which they are attached form a pyrrolidinyl, morpholinyl or piperazinyl ring,
   in which the pyrrolidinyl, morpholinyl or piperazinyl ring may be substituted by 1 or 2 methyl substituents,
 where 4-pyridyl may be substituted in the 2-position by fluorine,
 where 1,3,5-triazinyl is up to disubstituted by —$NR^{9A}R^{10A}$,
  in which
  $R^{9A}$ represents hydrogen or methyl,
  $R^{10A}$ represents hydrogen, $(C_1-C_6)$-alkyl or phenyl,
   in which $(C_1-C_6)$-alkyl may be substituted by amino and up to three times by fluorine,
  where 1,3,5-triazinyl may be substituted by chlorine,
$R^4$ represents hydrogen,
$R^5$ represents hydrogen, chlorine or methyl,
$R^6$ represents hydrogen,
and the N-oxides, salts, solvates, salts of the N-oxides and solvates of the N-oxides and salts thereof.
Except for the Compounds
N-(3-{8-[(2,6-difluorobenzyl)oxy]-2-methylimidazo[1,2-a]pyridin-3-yl}phenyl)acetamide,
8-[(2,6-difluorobenzyl)oxy]-2-methyl-3-[3-(piperidin-1-yl)phenyl]imidazo[1,2-a]pyridine.
In the context of the present invention, preference is also given to compounds of the formula (I) in which
$R^1$ represents a phenyl group of the formula

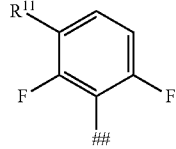

where
represents the point of attachment to A,
and
$R^{11}$ represents hydrogen or fluorine,
and the N-oxides, salts, solvates, salts of the N-oxides and solvates of the N-oxides and salts thereof.
In the context of the present invention, preference is also given to compounds of the formula (I) in which
$R^1$ represents a pyridyl group of the formula

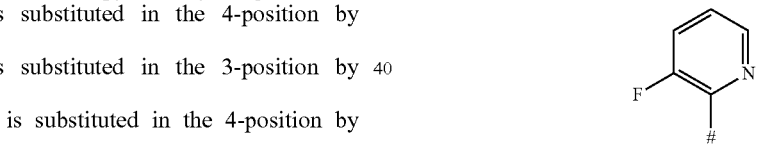

where
\# represents the point of attachment to A,
and the N-oxides, salts, solvates, salts of the N-oxides and solvates of the N-oxides and salts thereof.
In the context of the present invention, preference is also given to compounds of the formula (I) in
which
$R^2$ represents methyl,
and the N-oxides, salts, solvates, salts of the N-oxides and solvates of the N-oxides and salts thereof.
In the context of the present invention, preference is also given to compounds of the formula (I) in
which
$R^3$ represents phenyl,
 where phenyl is substituted in the 3-position by —$NR^7R^8$,
  in which
  $R^7$ represents hydrogen,
  $R^8$ represents methylcarbonyl,
  or
  $R^7$ and $R^8$ together with the nitrogen atom to which they are attached form a pyrrolidinyl ring,
and the N-oxides, salts, solvates, salts of the N-oxides and solvates of the N-oxides and salts thereof.

In the context of the present invention, preference is also given to compounds of the formula (I) in
which
$R^3$ represents 3-pyridyl, 4-pyridyl, 2-pyrimidyl, 5-pyrimidyl or 1,3,5-triazinyl,
  where 3-pyridyl is substituted in the 4-position by —$NR^9R^{10}$,
  where 4-pyridyl is substituted in the 3-position by —$NR^9R^{10}$,
  where 2-pyrimidyl is substituted in the 4-position by —$NR^9R^{10}$,
  where 5-pyrimidyl is substituted in the 2-position by —$NR^9R^{10}$,
    in which in each case
    $R^9$ represents hydrogen or methyl,
    $R^{10}$ represents $(C_1-C_6)$-alkyl or phenyl,
      in which $(C_1-C_6)$-alkyl may be substituted by 1 or 2 substituents independently of one another selected from the group consisting of $(C_1-C_4)$-alkoxy, amino and phenyl, and up to trisubstituted by fluorine,
    or
    $R^9$ and $R^{10}$ together with the nitrogen atom to which they are attached form a pyrrolidinyl, morpholinyl or piperazinyl ring,
      in which the pyrrolidinyl, morpholinyl or piperazinyl ring may be substituted by 1 or 2 methyl substituents,
  where 4-pyridyl may be substituted in the 2-position by fluorine,
  where 1,3,5-triazinyl is up to disubstituted by —$NR^{9A}R^{10A}$,
    in which
    $R^{9A}$ represents hydrogen or methyl,
    $R^{10A}$ represents hydrogen, $(C_1-C_6)$-alkyl or phenyl,
      in which $(C_1-C_6)$-alkyl may be substituted by amino and up to three times by fluorine,
  where 1,3,5-triazinyl may be substituted by chlorine,
and the N-oxides, salts, solvates, salts of the N-oxides and solvates of the N-oxides and salts thereof.

In the context of the present invention, preference is also given to compounds of the formula (I) in
which
$R^3$ represents 3-pyridyl,
  where 3-pyridyl is substituted in the 4-position by —$NR^9R^{10}$,
    in which
    $R^9$ represents hydrogen or methyl,
    $R^{10}$ represents $(C_1-C_6)$-alkyl or phenyl,
      in which $(C_1-C_6)$-alkyl may be substituted by 1 or 2 substituents independently of one another selected from the group consisting of $(C_1-C_4)$-alkoxy, amino and phenyl, and up to trisubstituted by fluorine,
    or
    $R^9$ and $R^{10}$ together with the nitrogen atom to which they are attached form a pyrrolidinyl, morpholinyl or piperazinyl ring,
      in which the pyrrolidinyl, morpholinyl or piperazinyl ring may be substituted by 1 or 2 methyl substituents,
and the N-oxides, salts, solvates, salts of the N-oxides and solvates of the N-oxides and salts thereof.

In the context of the present invention, particular preference is also given to compounds of the formula (I) in
which
$R^3$ represents 3-pyridyl,
  where 3-pyridyl is substituted in the 4-position by —$NR^9R^{10}$,
    in which
    $R^9$ represents hydrogen or methyl,
    $R^{10}$ represents methyl, ethyl or phenyl,
      in which methyl and ethyl may be substituted by $(C_1-C_4)$-alkoxy, amino and phenyl,
    or
    $R^9$ and $R^{10}$ together with the nitrogen atom to which they are attached form a morpholinyl or piperazinyl ring,
      in which the morpholinyl or piperazinyl ring may be substituted by 1 or 2 methyl substituents,
and the N-oxides, salts, solvates, salts of the N-oxides and solvates of the N-oxides and salts thereof.

In the context of the present invention, preference is also given to compounds of the formula (I) in
which
$R^3$ represents 4-pyridyl,
  where 4-pyridyl is substituted in the 3-position by —$NR^9R^{10}$,
    in which
    $R^9$ represents hydrogen or methyl,
    $R^{10}$ represents $(C_1-C_6)$-alkyl or phenyl,
      in which $(C_1-C_6)$-alkyl may be substituted by 1 or 2 substituents independently of one another selected from the group consisting of $(C_1-C_4)$-alkoxy, amino and phenyl, and up to trisubstituted by fluorine,
    or
    $R^9$ and $R^{10}$ together with the nitrogen atom to which they are attached form a pyrrolidinyl, morpholinyl or piperazinyl ring,
      in which the pyrrolidinyl, morpholinyl or piperazinyl ring may be substituted by 1 or 2 methyl substituents,
  where 4-pyridyl may be substituted in the 2-position by fluorine,
and the N-oxides, salts, solvates, salts of the N-oxides and solvates of the N-oxides and salts thereof.

In the context of the present invention, particular preference is also given to compounds of the formula (I) in
which
$R^3$ represents 4-pyridyl,
  where 4-pyridyl is substituted in the 3-position by —$NR^9R^{10}$,
    in which
    $R^9$ represents hydrogen,
    $R^{10}$ represents $(C_1-C_6)$-alkyl,
      in which $(C_1-C_6)$-alkyl is substituted by amino,
    or
    $R^9$ and $R^{10}$ together with the nitrogen atom to which they are attached form a piperazinyl ring,
  where 4-pyridyl may be substituted in the 2-position by fluorine,
and the N-oxides, salts, solvates, salts of the N-oxides and solvates of the N-oxides and salts thereof.

In the context of the present invention, preference is also given to compounds of the formula (I) in
which
$R^3$ represents 2-pyrimidyl,
  where 2-pyrimidyl is substituted in the 4-position by —$NR^9R^{10}$, in which
R⁹ represents hydrogen or methyl,
R¹⁰ represents (C₁-C₆)-alkyl or phenyl,
in which (C₁-C₆)-alkyl may be substituted by 1 or 2 substituents independently of one another selected from the group consisting of (C₁-C₄)-alkoxy, amino and phenyl, and up to trisubstituted by fluorine,
or
R⁹ and R¹⁰ together with the nitrogen atom to which they are attached form a pyrrolidinyl, morpholinyl or piperazinyl ring,
in which the pyrrolidinyl, morpholinyl or piperazinyl ring may be substituted by 1 or 2 methyl substituents,
and the N-oxides, salts, solvates, salts of the N-oxides and solvates of the N-oxides and salts thereof.

In the context of the present invention, particular preference is also given to compounds of the formula (I) in which
R³ represents 2-pyrimidyl,
where 2-pyrimidyl is substituted in the 4-position by —NR⁹R¹⁰,
in which
R⁹ represents hydrogen or methyl,
R¹⁰ represents methyl or phenyl,
in which methyl may be substituted by phenyl,
or
R⁹ and R¹⁰ together with the nitrogen atom to which they are attached form a pyrrolidinyl ring,
and the N-oxides, salts, solvates, salts of the N-oxides and solvates of the N-oxides and salts thereof.

In the context of the present invention, preference is also given to compounds of the formula (I) in which
R³ represents 1,3,5-triazinyl,
where 1,3,5-triazinyl is up to disubstituted by —NR⁹ᴬR¹⁰ᴬ,
in which
R⁹ᴬ represents hydrogen or methyl,
R¹⁰ᴬ represents hydrogen, (C₁-C₆)-alkyl or phenyl,
in which (C₁-C₆)-alkyl may be substituted by amino and up to three times by fluorine,
where 1,3,5-triazinyl may be substituted by chlorine,
and the N-oxides, salts, solvates, salts of the N-oxides and solvates of the N-oxides and salts thereof.

In the context of the present invention, preference is also given to compounds of the formula (I) in which
R⁵ represents hydrogen, chlorine or methyl,
and the N-oxides, salts, solvates, salts of the N-oxides and solvates of the N-oxides and salts thereof.

In the context of the present invention, preference is also given to compounds of the formula (I) in which
R⁵ represents chlorine,
and the N-oxides, salts, solvates, salts of the N-oxides and solvates of the N-oxides and salts thereof.

In the context of the present invention, particular preference is also given to compounds of the formula (I) in which
R⁵ represents hydrogen or methyl,
and the N-oxides, salts, solvates, salts of the N-oxides and solvates of the N-oxides and salts thereof.

In the context of the present invention, particular preference is also given to compounds of the formula (I) in which
R⁵ represents hydrogen,
and the N-oxides, salts, solvates, salts of the N-oxides and solvates of the N-oxides and salts thereof.

In the context of the present invention, particular preference is also given to compounds of the formula (I) in which
R⁵ represents methyl,
and the N-oxides, salts, solvates, salts of the N-oxides and solvates of the N-oxides and salts thereof.

The individual radical definitions specified in the respective combinations or preferred combinations of radicals are, independently of the respective combinations of the radicals specified, also replaced as desired by radical definitions of other combinations.

Particular preference is given to combinations of two or more of the preferred ranges mentioned above.

The invention further provides a process for preparing the compounds of the formula (I) according to the invention, characterized in that
[A] a compound of the formula (II)

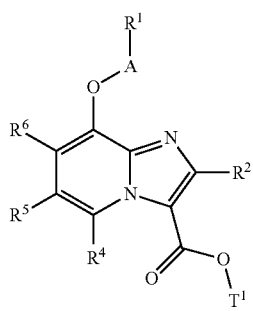

in which A, R¹, R², R⁴, R⁵ and R⁶ are each as defined above and
T¹ represents (C₁-C₄)-alkyl or benzyl,
is reacted in an inert solvent in the presence of a suitable base or acid to give a carboxylic acid of the formula (III)

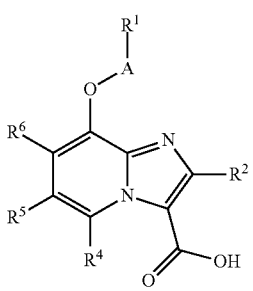

in which A, R¹, R², R⁴, R⁵ and R⁶ each have the meanings given above, and these are subsequently reacted in the presence of a suitable acid to give an imidazo[1,2-a]-pyridine of the formula (IV)

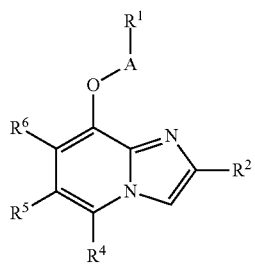

(IV)

in which A, R¹, R², R⁴, R⁵ and R⁶ each have the meanings given above, and this is then converted with a halogen equivalent into a compound of the formula (V)

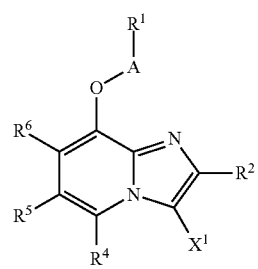

(V)

in which A, R¹, R², R⁴, R⁵ and R⁶ are each as defined above and

X¹ represents chlorine, bromine or iodine, and this is subsequently reacted in an inert solvent, in the presence of a suitable transition metal catalyst, with a compound of the formula (VI)

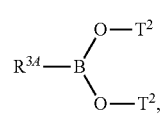

(VI)

in which

R³·⁴ has the meanings given above for R³ and

T² represents hydrogen or (C₁-C₄)-alkyl, or the two T² radicals together form a —C(CH₃)₂—C(CH₃)₂— bridge, any protective groups present are subsequently detached, and the resulting compounds of the formula (I) are optionally converted with the appropriate (i) solvents and/or (ii) acids or bases to the solvates, salts and/or solvates of the salts thereof.

The preparation processes described can be illustrated by way of example by the following synthesis scheme (Scheme 1):

Scheme 1:

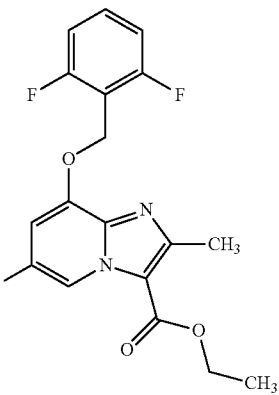

a)

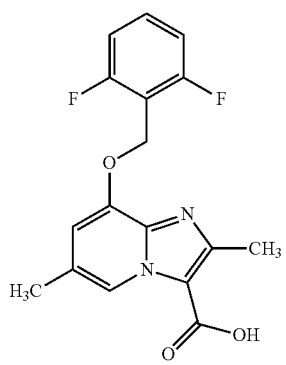

b)

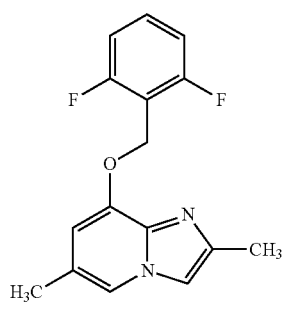

c)

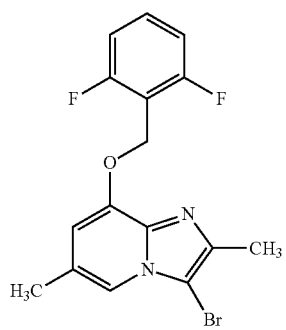

d)

-continued

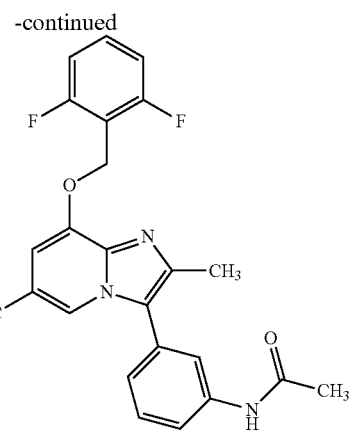

[a): lithium hydroxide, THF/methanol/ H₂O, RT; b): 6N hydrochloric acid, 100° C.; c): N-bromosuccinimide, ethanol, RT; d): (3-acetamidophenyl)boric acid, bis(tri-tert-butylphosphine)palladium(0), K₃PO₄, ethanol/water/toluene, 120° C.].

The compounds of the formulae (VI), (VIII) and (X) are commercially available, known from the literature or can be prepared in analogy to literature processes.

The hydrolysis of the ester group $T^1$ in the compounds of the formula (II) is carried out by customary methods, by treating the esters in inert solvents with acids or bases, in which latter case the salts formed at first are converted to the free carboxylic acids by treating with acid. In the case of the tert-butyl esters, the ester hydrolysis is preferably carried out with acids. In the case of the benzyl esters, the ester cleavage is preferably carried out by hydrogenolysis with palladium on activated carbon or Raney nickel. Suitable inert solvents for this reaction are water or the organic solvents customary for ester hydrolysis. These preferably include alcohols such as methanol, ethanol, n-propanol, isopropanol, n-butanol or tert-butanol, or ethers such as diethyl ether, tetrahydrofuran, 2-methyltetrahydrofuran, dioxane or glycol dimethyl ether, or other solvents such as acetone, dichloromethane, dimethylformamide or dimethyl sulfoxide. It is also possible to use mixtures of the solvents mentioned. In the case of a basic ester hydrolysis, preference is given to using mixtures of water with dioxane, tetrahydrofuran, methanol and/or ethanol.

Suitable bases for the ester hydrolysis are the customary inorganic bases. These preferably include alkali metal or alkaline earth metal hydroxides, for example sodium hydroxide, lithium hydroxide, potassium hydroxide or barium hydroxide, or alkali metal or alkaline earth metal carbonates, such as sodium carbonate, potassium carbonate or calcium carbonate. Particular preference is given to sodium hydroxide or lithium hydroxide.

Suitable acids for the ester hydrolysis are generally sulfuric acid, hydrogen chloride/hydrochloric acid, hydrogen bromide/hydrobromic acid, phosphoric acid, acetic acid, trifluoroacetic acid, toluenesulfonic acid, methanesulfonic acid or trifluoromethanesulfonic acid, or mixtures thereof, optionally with addition of water. Preference is given to hydrogen chloride or trifluoroacetic acid in the case of the tert-butyl esters and to hydrochloric acid in the case of the methyl esters.

The ester hydrolysis is generally carried out within a temperature range from 0° C. to +100° C., preferably at +0° C. to +50° C.

These conversions can be performed at atmospheric, elevated or reduced pressure (for example from 0.5 to 5 bar). In general, the reaction is in each case carried out at atmospheric pressure.

A suitable solvent for the process step (III)→(IV) is water.

Suitable acids for the process step (III)→(IV) are hydrogen chloride/hydrochloric acid, hydrogen bromide/hydrobromic acid, sulfuric acid, acetic acid or mixtures thereof, optionally with addition of water. Preference is given to using hydrochloric acid.

The decarboxylation (III)→(IV) is generally carried out in a temperature range of from +20° C. to +100° C., preferably at from 75° C. to +100° C. The conversion can be carried out under atmospheric, elevated or reduced pressure (for example from 0.5 to 5 bar). In general, the reaction is carried out at atmospheric pressure.

Suitable solvents for process step (IV)→(V) include alcohols such as methanol, ethanol, n-propanol, isopropanol, n-butanol or tert-butanol, or ethers such as diethyl ether, tetrahydrofuran, 2-methyltetrahydrofuran, dioxane or glycol dimethyl ether, or other solvents such as acetone, dichloromethane, dimethylformamide or dimethyl sulfoxide. It is also possible to use mixtures of the solvents mentioned. Preference is given to using methanol and/or ethanol.

A suitable halogen source for the reaction (IV)→(V) is, for example, N-bromosuccinimide, N-chlorosuccinimide, N-iodosuccinimide, chlorine, bromine or iodine. Preference is given to using N-bromosuccinimide.

The reaction (IV)→(V) is generally carried out in a temperature range of from +20° C. to +100° C., preferably in the range from +20° C. to +80° C. The reaction can be performed at atmospheric, elevated or reduced pressure (for example in the range from 0.5 to 5 bar). In general, the reaction is carried out at atmospheric pressure.

Process step (V)+(VI)→(I) is carried out in a solvent which is inert under the reaction conditions. Suitable solvents are, for example, alcohols such as methanol, ethanol, n-propanol, isopropanol, n-butanol or tert-butanol, ethers such as diethyl ether, dioxane, tetrahydrofuran, glycol dimethyl ether or diethylene glycol dimethyl ether, or other solvents such as 1,2-dimethoxyethane (DME), dimethylformamide (DMF), dimethyl sulfoxide (DMSO), N,N'-dimethylpropyleneurea (DMPU), N-methylpyrrolidone (NMP), pyridine, acetonitrile, toluene or else water. It is also possible to use mixtures of the solvents mentioned. Preference is given to methanol, ethanol, dioxane, toluene and water. The conversion (V)+(VI)→(I) can optionally be carried out in the presence of a suitable palladium and/or copper catalyst. A suitable palladium catalyst is, for example, palladium (II) acetate, tetrakis(triphenylphosphine)palladium(0), bis(tri-tert-butylphosphine)palladium(0), bis(triphenylphosphine)palladium(II) chloride, bis(acetonitrile) palladium(II) chloride and [1,1'-bis(diphenylphosphino) ferrocene]dichloropalladium(II) and the corresponding dichloromethane complex, optionally in conjunction with additional phosphane ligands, for example (2-biphenyl)di-tert-butylphosphine, 2-dicyclohexylphosphino-2',6'-dimethoxybiphenyl (SPHOS), dicyclohexyl[2',4',6'-tris(1-methylethyl)biphenyl-2-yl]phosphane (XPHOS), bis(2-phenylphosphinophenyl) ether (DPEphos), 4,5-bis(diphenylphosphino)-9,9-dimethylxanthene (Xantphos) [cf., for example, Hassan J. et al., Chem. Rev. 102, 1359-1469 (2002)] or chloro(2-dicyclohexylphosphino-2',4',6'-triisopropyl-1,1'-biphenyl) [2-(2'-amino-1,1'-biphenyl)palladium (II) [CAS: 1310584-14-5].

The conversion (V)+(VI)→(I) is optionally carried out in the presence of a suitable base. Suitable bases for this conversion are the customary inorganic or organic bases. These preferably include alkali metal hydroxides, for example lithium hydroxide, sodium hydroxide or potassium hydroxide, alkali metal or alkaline earth metal carbonates such as lithium carbonate, sodium carbonate, potassium carbonate, calcium carbonate or caesium carbonate, alkali metal alkoxides such as sodium methoxide or potassium methoxide, sodium ethoxide or potassium ethoxide or sodium or potassium tert-butoxide, alkali metal hydrides such as sodium hydride or potassium hydride, amides such as sodium amide, lithium bis(trimethylsilyl)amide, sodium bis(trimethylsilyl)amide or potassium bis(trimethylsilyl)amide or lithium diisopropylamide, or organic amines such as triethylamine, N-methylmorpholine, N-methylpiperidine, N,N-diisopropylethylamine, pyridine, 1,5-diazabicyclo[4.3.0]non-5-ene (DBN), 1,8-diazabicyclo[5.4.0]undec-7-ene (DBU) or 1,4-diazabicyclo[2.2.2]octane (DABCO®) or potassium phosphate. Preference is given to using potassium phosphate.

The reaction (V)+(VI)→(I) is generally carried out in a temperature range from 0° C. to +200° C., preferably at from +60° C. to +120° C. The conversion can be carried out under atmospheric, elevated or reduced pressure (for example from 0.5 to 5 bar). In general, the reaction is carried out at atmospheric pressure.

The compounds of the formula (II) are known from the literature or can be prepared by reacting a compound of the formula (VII)

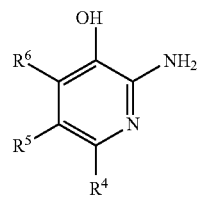

(VII)

in which $R^4$, $R^5$ and $R^6$ have the meaning given above, in an inert solvent in the presence of a suitable base with a compound of the formula (VIII)

(VIII)

in which A and $R^1$ have the meaning given above and $X^1$ represents a suitable leaving group, in particular chlorine, bromine, iodine, mesylate, triflate or tosylate, to give a compound of the formula (IX)

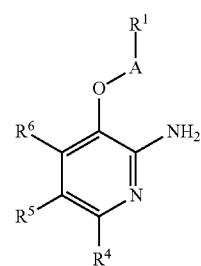

(IX)

in which A, $R^1$, $R^4$, $R^5$ and $R^6$ each have the meanings given above,
and then reacting this in an inert solvent with a compound of the formula (X)

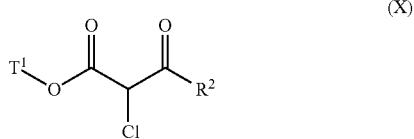

(X)

in which $R^2$ and $T^1$ are each as defined above.

The process described is illustrated in an exemplary manner by the scheme below (Scheme 2):

Scheme 2:

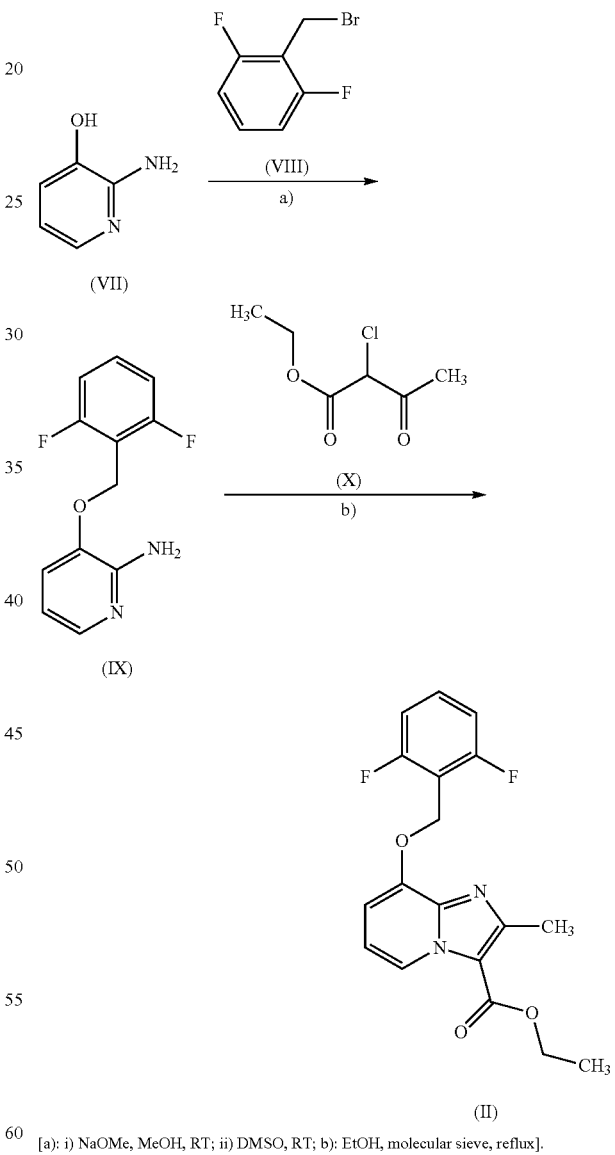

[a): i) NaOMe, MeOH, RT; ii) DMSO, RT; b): EtOH, molecular sieve, reflux].

The synthesis sequence shown can be modified such that the respective reaction steps are carried out in a different order. An example of such a modified synthesis sequence is shown in Scheme 3.

Scheme 3:

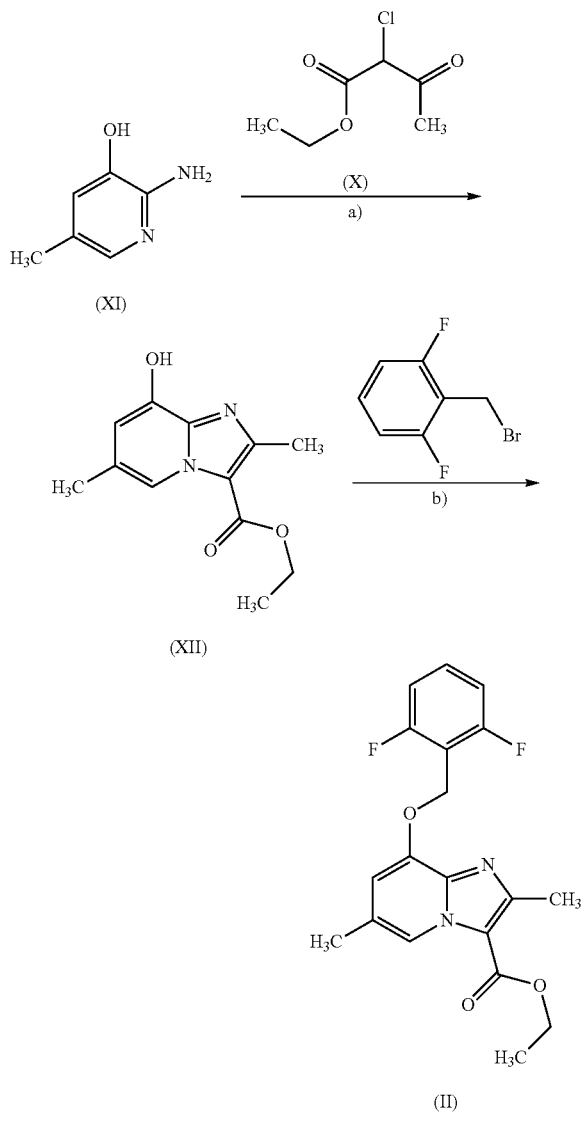

[a]: EtOH, molecular sieve, reflux; b): b) Cs$_2$CO$_3$, DMF, 50° C.].

Inert solvents for the process step (VII)+(VIII)→(IX) are, for example, halohydrocarbons such as dichloromethane, trichloromethane, tetrachloromethane, trichloroethylene or chlorobenzene, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, alcohols such as methanol, ethanol, tert-butanol, or other solvents such as acetone, methyl ethyl ketone, ethyl acetate, acetonitrile, N,N-dimethylformamide, dimethyl sulfoxide, N,N'-dimethylpropyleneurea (DMPU), N-methylpyrrolidone (NMP) or pyridine. It is also possible to use mixtures of the solvents mentioned. Preference is given to using methanol, dimethylformamide or dimethyl sulfoxide.

Suitable bases for the process step (VII)+(VIII)→(IX) are the customary inorganic or organic bases. These preferably include alkali metal hydroxides, for example lithium hydroxide, sodium hydroxide or potassium hydroxide, alkali metal or alkaline earth metal carbonates such as lithium carbonate, sodium carbonate, potassium carbonate, calcium carbonate or caesium carbonate, optionally with addition of an alkali metal iodide, for example sodium iodide or potassium iodide, alkali metal alkoxides such as sodium methoxide or potassium methoxide, sodium ethoxide or potassium ethoxide or sodium or potassium tert-butoxide, alkali metal hydrides such as sodium hydride or potassium hydride, amides such as sodium amide, lithium bis(trimethylsilyl) amide or potassium bis(trimethylsilyl)amide or lithium diisopropylamide, or organic amines such as triethylamine, N-methylmorpholine, N-methylpiperidine, N,N-diisopropylethylamine, pyridine, 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using potassium carbonate, caesium carbonate or sodium methoxide.

The reaction is generally carried out within a temperature range from 0° C. to +120° C., preferably at +20° C. to +80° C., optionally in a microwave. The reaction can be carried out under atmospheric, elevated or reduced pressure (for example from 0.5 to 5 bar).

Inert solvents for the ring closure to give the imidazo[1,2-a]pyridine skeleton (IX)+(X)→(II) or (XI)+(X)→(XII) are the customary organic solvents. These preferably include alcohols such as methanol, ethanol, n-propanol, isopropanol, n-butanol, n-pentanol or tert-butanol, or ethers such as diethyl ether, tetrahydrofuran, 2-methyltetrahydrofuran, dioxane or glycol dimethyl ether, or other solvents such as acetone, dichloromethane, 1,2-dichloroethane, acetonitrile, dimethylformamide or dimethyl sulfoxide. It is also possible to use mixtures of the solvents mentioned. Preference is given to using ethanol.

The ring closure is generally carried out within a temperature range from +50° C. to +150° C., preferably at +50° C. to +100° C., optionally in a microwave.

The ring closure (IX)+(X)→(II) or (XI)+(X)→(XII) is optionally carried out in the presence of dehydrating reaction additives, for example in the presence of molecular sieve (pore size 4 Å) or by means of a water separator. The reaction (IX)+(X)→(II) or (XI)+(X)→(XII) is carried out using an excess of the reagent of the formula (X), for example with 1 to 20 equivalents of the reagent (X), optionally with addition of bases (for example sodium hydrogencarbonate), in which case the addition of this reagent can be effected all at once or in several portions.

Further compounds of the invention can optionally also be prepared by conversions of functional groups of individual substituents, especially those listed for $R^3$, proceeding from the compounds of the formula (I) obtained by above processes. These conversions are performed by customary methods known to those skilled in the art and include, for example, reactions such as nucleophilic and electrophilic substitutions, oxidations, reductions, hydrogenations, transition metal-catalysed coupling reactions, eliminations, alkylation, amination, esterification, ester hydrolysis, etherification, ether hydrolysis, formation of carbonamides, and introduction and removal of temporary protective groups.

The compounds of the invention have valuable pharmacological properties and can be used for prevention and treatment of diseases in humans and animals. The compounds of the invention offer a further treatment alternative and thus enlarge the field of pharmacy.

The compounds of the invention bring about vasorelaxation and inhibition of platelet aggregation, and lead to a decrease in blood pressure and to a rise in coronary blood flow. These effects are mediated by a direct stimulation of soluble guanylate cyclase and an intracellular rise in cGMP.

In addition, the compounds of the invention enhance the action of substances which increase the cGMP level, for example EDRF (endothelium-derived relaxing factor), NO donors, protoporphyrin IX, arachidonic acid or phenylhydrazine derivatives.

The compounds of the invention are suitable for the treatment and/or prophylaxis of cardiovascular, pulmonary, thromboembolic and fibrotic disorders.

Accordingly, the compounds according to the invention can be used in medicaments for the treatment and/or prophylaxis of cardiovascular disorders such as, for example, high blood pressure (hypertension), resistant hypertension, acute and chronic heart failure, coronary heart disease, stable and unstable angina pectoris, peripheral and cardiac vascular disorders, arrhythmias, atrial and ventricular arrhythmias and impaired conduction such as, for example, atrioventricular blocks degrees I-III (AB block I-III), supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, sick sinus syndrome, syncopes, AV-nodal re-entry tachycardia, Wolff-Parkinson-White syndrome, of acute coronary syndrome (ACS), autoimmune cardiac disorders (pericarditis, endocarditis, valvolitis, aortitis, cardiomyopathies), shock such as cardiogenic shock, septic shock and anaphylactic shock, aneurysms, boxer cardiomyopathy (premature ventricular contraction (PVC)), for the treatment and/or prophylaxis of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation such as, for example, pulmonary oedema, cerebral oedema, renal oedema or oedema caused by heart failure, peripheral circulatory disturbances, reperfusion damage, arterial and venous thromboses, microalbuminuria, myocardial insufficiency, endothelial dysfunction, to prevent restenoses, for example after thrombolysis therapies, percutaneous transluminal angioplasties (PTA), transluminal coronary angioplasties (PTCA), heart transplants and bypass operations, and also micro- and macrovascular damage (vasculitis), increased levels of fibrinogen and of low-density lipoprotein (LDL) and increased concentrations of plasminogen activator inhibitor 1 (PAI-1), and also for the treatment and/or prophylaxis of erectile dysfunction and female sexual dysfunction.

In the context of the present invention, the term "heart failure" encompasses both acute and chronic manifestations of heart failure, and also more specific or related types of disease, such as acute decompensated heart failure, right heart failure, left heart failure, global failure, ischaemic cardiomyopathy, dilated cardiomyopathy, hypertrophic cardiomyopathy, idiopathic cardiomyopathy, congenital heart defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, diastolic heart failure and systolic heart failure and acute phases of worsening of existing chronic heart failure (worsening heart failure).

In addition, the compounds of the invention can also be used for the treatment and/or prophylaxis of arteriosclerosis, impaired lipid metabolism, hypolipoproteinaemias, dyslipidaemias, hypertriglyceridaemias, hyperlipidaemias, hypercholesterolaemias, abetelipoproteinaemia, sitosterolaemia, xanthomatosis, Tangier disease, adiposity, obesity and of combined hyperlipidaemias and metabolic syndrome.

The compounds of the invention can also be used for the treatment and/or prophylaxis of primary and secondary Raynaud's phenomenon, microcirculation impairments, claudication, peripheral and autonomic neuropathies, diabetic microangiopathies, diabetic retinopathy, diabetic ulcers on the extremities, gangrene, CREST syndrome, erythematosis, onychomycosis, rheumatic disorders and for promoting wound healing.

The compounds according to the invention are furthermore suitable for treating urological disorders such as, for example, benign prostate syndrome (BPS), benign prostate hyperplasia (BPH), benign prostate enlargement (BPE), bladder outlet obstruction (BOO), lower urinary tract syndromes (LUTS, including Feline Urological Syndrome (FUS)), disorders of the urogenital system including neurogenic over-active bladder (OAB) and (IC), incontinence (UI) such as, for example, mixed urinary incontinence, urge urinary incontinence, stress urinary incontinence or overflow urinary incontinence (MUI, UUI, SUI, OUI), pelvic pain, benign and malignant disorders of the organs of the male and female urogenital system.

The compounds of the invention are also suitable for the treatment and/or prophylaxis of kidney disorders, in particular of acute and chronic renal insufficiency and acute and chronic renal failure. In the context of the present invention, the term "renal insufficiency" encompasses both acute and chronic manifestations of renal insufficiency, and also underlying or related renal disorders such as renal hypoperfusion, intradialytic hypotension, obstructive uropathy, glomerulopathies, glomerulonephritis, acute glomerulonephritis, glomerulosclerosis, tubulointerstitial diseases, nephropathic disorders such as primary and congenital kidney disease, nephritis, immunological kidney disorders such as kidney transplant rejection and immunocomplex-induced kidney disorders, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphatemia and/or need for dialysis. The present invention also encompasses the use of the compounds of the invention for the treatment and/or prophylaxis of sequelae of renal insufficiency, for example pulmonary edema, heart failure, uremia, anemia, electrolyte disorders (for example hyperkalemia, hyponatremia) and disorders in bone and carbohydrate metabolism.

In addition, the compounds of the invention are also suitable for the treatment and/or prophylaxis of asthmatic disorders, pulmonary arterial hypertension (PAH) and other forms of pulmonary hypertension (PH) including left-heart disease-, HIV-, sickle cell anaemia-, thromboembolism- (CTEPH), sarcoidosis-, COPD- or pulmonary fibrosis-associated pulmonary hypertension, chronic-obstructive pulmonary disease (COPD), acute respiratory distress syndrome (ARDS), acute lung injury (ALI), alpha-1-antitrypsin deficiency (AATD), pulmonary fibrosis, pulmonary emphysema (for example pulmonary emphysema induced by cigarette smoke) and cystic fibrosis (CF).

The compounds described in the present invention are also active compounds for control of central nervous system disorders characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post-stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelinization, multiple sclerosis, thalamic degeneration, Creutzfeldt-Jakob dementia, HIV dementia, schizophrenia with dementia or Korsakoff's psychosis. They are also suitable for the treatment and/or prophylaxis of central nervous system disorders such as states of anxiety, tension and depression, CNS-related sexual dysfunctions and sleep disturbances, and for controlling pathological disturbances of the intake of food, stimulants and addictive substances.

In addition, the compounds of the invention are also suitable for controlling cerebral blood flow and are effective agents for controlling migraine. They are also suitable for the prophylaxis and control of sequelae of cerebral infarct (Apoplexia cerebri) such as stroke, cerebral ischemias and skull-brain trauma. The compounds of the invention can likewise be used for controlling states of pain and tinnitus.

In addition, the compounds of the invention have anti-inflammatory action and can therefore be used as anti-inflammatory agents for the treatment and/or prophylaxis of sepsis (SIRS), multiple organ failure (MODS, MOF), inflammatory disorders of the kidney, chronic intestinal inflammations (IBD, Crohn's disease, UC), pancreatitis, peritonitis, rheumatoid disorders, inflammatory skin disorders and inflammatory eye disorders.

Furthermore, the compounds according to the invention can also be used for the treatment and/or prophylaxis of autoimmune diseases.

The compounds of the invention are also suitable for the treatment and/or prophylaxis of fibrotic disorders of the internal organs, for example the lung, the heart, the kidney, the bone marrow and in particular the liver, and also dermatological fibroses and fibrotic eye disorders. In the context of the present invention, the term fibrotic disorders includes in particular the following terms: hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis and similar fibrotic disorders, scleroderma, morphea, keloids, hypertrophic scarring (also following surgical procedures), naevi, diabetic retinopathy, proliferative vitroretinopathy and disorders of the connective tissue (for example sarcoidosis).

The compounds of the invention are also suitable for controlling postoperative scarring, for example as a result of glaucoma operations.

The compounds of the invention can also be used cosmetically for ageing and keratinizing skin.

Moreover, the compounds according to the invention are suitable for the treatment and/or prophylaxis of hepatitis, neoplasms, osteoporosis, glaucoma and gastroparesis.

The present invention further provides for the use of the compounds of the invention for the treatment and/or prophylaxis of disorders, especially the disorders mentioned above.

The present invention further provides for the use of the compounds according to the invention for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides the compounds of the invention for use in a method for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides for the use of the compounds of the invention for production of a medicament for the treatment and/or prophylaxis of disorders, especially the disorders mentioned above.

The present invention further provides for the use of the compounds according to the invention for production of a medicament for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides a method for the treatment and/or prophylaxis of disorders, in particular the disorders mentioned above, using an effective amount of at least one of the compounds of the invention.

The present invention further provides a method for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis using an effective amount of at least one of the compounds of the invention.

The compounds according to the invention can be used alone or, if required, in combination with other active ingredients. The present invention further provides medicaments comprising at least one of the compounds of the invention and one or more further active compounds, especially for the treatment and/or prophylaxis of the aforementioned disorders. Preferred examples of suitable combination active ingredients include:

organic nitrates and NO donors, for example sodium nitroprusside, nitroglycerin, isosorbide mononitrate, isosorbide dinitrate, molsidomine or SIN-1, and inhaled NO; and/or compounds which inhibit the breakdown of cyclic guanosine monophosphate (cGMP), for example inhibitors of phosphodiesterases (PDE) 1, 2 and/or 5, especially PDE 5 inhibitors such as sildenafil, vardenafil and tadalafil; and/or agents having antithrombotic activity, for example and with preference from the group of the platelet aggregation inhibitors, the anticoagulants and the profibrinolytic substances; and/or hypotensive active compounds, by way of example and with preference from the group of the calcium antagonists, angiotensin AII antagonists, ACE inhibitors, endothelin antagonists, renin inhibitors, alpha-receptor blockers, beta-receptor blockers, mineralocorticoid receptor antagonists, neutral endopeptidase (NEP) inhibitors and combinations of these groups and the diuretics; and/or lipid metabolism modifiers, by way of example and with preference from the group of the thyroid receptor agonists, cholesterol synthesis inhibitors, by way of example and with preference HMG-CoA reductase or squalene synthesis inhibitors, of the ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists; and/or antifibrotic agents, by way of example and with preference from the group of the kinase inhibitors or TGF-beta or TNF-alpha modulators.

Antithrombotic agents are preferably understood to mean compounds from the group of the platelet aggregation inhibitors, the anticoagulants or the profibrinolytic substances.

In a preferred embodiment of the invention, the compounds of the invention are administered in combination with a platelet aggregation inhibitor, by way of example and with preference aspirin, clopidogrel, ticlopidine or dipyridamole.

In a preferred embodiment of the invention, the compounds of the invention are administered in combination with a thrombin inhibitor, by way of example and with preference ximelagatran, dabigatran, melagatran, bivalirudin or clexane.

In a preferred embodiment of the invention, the compounds of the invention are administered in combination with a GPIIb/IIIa antagonist, by way of example and with preference tirofiban or abciximab.

In a preferred embodiment of the invention, the compounds according to the invention are administered in combination with a factor Xa inhibitor, by way of example and with preference rivaroxaban (BAY 59-7939), edoxaban (DU-176b), apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds of the invention are administered in combination with heparin or with a low molecular weight (LMW) heparin derivative.

In a preferred embodiment of the invention, the compounds of the invention are administered in combination with a vitamin K antagonist, by way of example and with preference coumarin.

Hypotensive agents are preferably understood to mean compounds from the group of the calcium antagonists, angiotensin AII antagonists, ACE inhibitors, endothelin antagonists, renin inhibitors, alpha-receptor blockers, beta-receptor blockers, mineralocorticoid receptor antagonists, neutral endopeptidase (NEP) inhibitors, and the diuretics.

In a preferred embodiment of the invention, the compounds of the invention are administered in combination with a calcium antagonist, by way of example and with preference nifedipine, amlodipine, verapamil or diltiazem.

In a preferred embodiment of the invention, the compounds of the invention are administered in combination with an alpha-1-receptor blocker, by way of example and with preference prazosin.

In a preferred embodiment of the invention, the compounds of the invention are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist, by way of example and with preference losartan, candesartan, valsartan, telmisartan or embursatan or a dual angiotensin AII antagonist/NEP inhibitor, for example and with preference LCZ696 (valsartan/sacubitril).

In a preferred embodiment of the invention, the compounds of the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds of the invention are administered in combination with an endothelin antagonist, by way of example and with preference bosentan, darusentan, ambrisentan or sitaxsentan.

In a preferred embodiment of the invention, the compounds of the invention are administered in combination with a renin inhibitor, by way of example and with preference aliskiren, SPP-600 or SPP-800.

In a preferred embodiment of the invention, the compounds of the invention are administered in combination with a mineralocorticoid receptor antagonist, by way of example and with preference spironolactone or eplerenone.

In a preferred embodiment of the invention, the compounds of the invention are administered in combination with a loop diuretic, for example furosemide, torasemide, bumetanide and piretanide, with potassium-sparing diuretics, for example amiloride and triamterene, with aldosterone antagonists, for example spironolactone, potassium canrenoate and eplerenone, and also thiazide diuretics, for example hydrochlorothiazide, chlorthalidone, xipamide and indapamide.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbers, bile acid reabsorption inhibitors, lipase inhibitors and the lipoprotein(a) antagonists.

In a preferred embodiment of the invention, the compounds of the invention are administered in combination with a CETP inhibitor, by way of example and with preference dalcetrapib, BAY 60-5521, anacetrapib or CETP vaccine (CETi-1).

In a preferred embodiment of the invention, the compounds of the invention are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the compounds of the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds of the invention are administered in combination with a squalene synthesis inhibitor, by way of example and with preference BMS-188494 or TAK-475.

In a preferred embodiment of the invention, the compounds of the invention are administered in combination with an ACAT inhibitor, by way of example and with preference avasimibe, melinamide, pactimibe, eflucimibe or SMP-797.

In a preferred embodiment of the invention, the compounds of the invention are administered in combination with an MTP inhibitor, by way of example and with preference implitapide, BMS-201038, R-103757 or JTT-130.

In a preferred embodiment of the invention, the compounds of the invention are administered in combination with a PPAR-gamma agonist, by way of example and with preference pioglitazone or rosiglitazone.

In a preferred embodiment of the invention, the compounds of the invention are administered in combination with a PPAR-delta agonist, by way of example and with preference GW 501516 or BAY 68-5042.

In a preferred embodiment of the invention, the compounds of the invention are administered in combination with a cholesterol absorption inhibitor, by way of example and with preference ezetimibe, tiqueside or pamaqueside.

In a preferred embodiment of the invention, the compounds of the invention are administered in combination with a lipase inhibitor, by way of example and with preference orlistat.

In a preferred embodiment of the invention, the compounds of the invention are administered in combination with a polymeric bile acid adsorber, by way of example and with preference cholestyramine, colestipol, colesolvam, CholestaGel or colestimide.

In a preferred embodiment of the invention, the compounds of the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds of the invention are administered in combination with a lipoprotein(a) antagonist, by way of example and with preference gemcabene calcium (CI-1027) or nicotinic acid.

In a preferred embodiment of the invention, the compounds of the invention are administered in combination with a kinase inhibitor, by way of example and with preference nintedanib.

In a preferred embodiment of the invention, the compounds according to the invention are administered in combination with an TGF-beta or TNF-alpha modulator, by way of example and with preference pirfenidone.

The present invention further provides medicaments which comprise at least one compound of the invention, typically together with one or more inert, non-toxic, pharmaceutically suitable excipients, and for the use thereof for the aforementioned purposes.

The compounds according to the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds according to the invention can be administered in administration forms suitable for these administration routes.

Suitable administration forms for oral administration are those which work according to the prior art and release the compounds of the invention rapidly and/or in a modified manner and which contain the compounds of the invention in crystalline and/or amorphized and/or dissolved form, for example tablets (uncoated or coated tablets, for example with gastric juice-resistant or retarded-dissolution or insoluble coatings which control the release of the compound of the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can be accomplished with avoidance of a resorption step (for example by an intravenous, intraarterial, intracardiac, intraspinal or intralumbar route) or with inclusion of a resorption (for example by an intramuscular, subcutaneous, intracutaneous, percutaneous or intraperitoneal route). Administration forms suitable for parenteral administration include preparations for injection and infusion in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Preference is given to oral or parenteral administration, especially oral administration.

The compounds according to the invention can be converted to the administration forms mentioned. This can be accomplished in a manner known per se by mixing with inert, non-toxic, pharmaceutically suitable auxiliaries. These excipients include carriers (for example microcrystalline cellulose, lactose, mannitol), solvents (e.g. liquid polyethylene glycols), emulsifiers and dispersing or wetting agents (for example sodium dodecylsulfate, polyoxysorbitan oleate), binders (for example polyvinylpyrrolidone), synthetic and natural polymers (for example albumin), stabilizers (e.g. antioxidants, for example ascorbic acid), colourants (e.g. inorganic pigments, for example iron oxides) and flavour and/or odour correctors.

In general, it has been found to be advantageous in the case of parenteral administration to administer amounts of about 0.001 to 1 mg/kg, preferably about 0.01 to 0.5 mg/kg, of body weight to achieve effective results. In the case of oral administration, the dose is about 0.001 to 2 mg/kg, preferably about 0.001 to 1 mg/kg, of body weight.

It may nevertheless be necessary in some cases to deviate from the stated amounts, specifically as a function of body weight, route of administration, individual response to the active ingredient, nature of the preparation and time or interval over which administration takes place. Thus in some cases it may be sufficient to manage with less than the abovementioned minimum amount, while in other cases the upper limit mentioned must be exceeded. In the case of administration of greater amounts, it may be advisable to divide them into several individual doses over the day.

The working examples which follow illustrate the invention. The invention is not restricted to the examples.

Unless stated otherwise, the percentages in the tests and examples which follow are percentages by weight; parts are parts by weight. Solvent ratios, dilution ratios and concentration data for liquid/liquid solutions are based in each case on volume.

A. Examples

Abbreviations and Acronyms abs. absolute (=dried)
aq. aqueous solution
calc. calculated
Boc tert-butyloxycarbonyl
br. broad signal (NMR coupling pattern)
CAS No. Chemical Abstracts Service number
Cbz benzyloxycarbonyl
δ shift in the NMR spectrum (stated in ppm)
d doublet (NMR coupling pattern)
TLC thin-layer chromatography
DCI direct chemical ionization (in MS)
DMAP 4-N, N-dimethylaminopyridine
DMF dimethylformamide
DMSO dimethyl sulfoxide
EDCI N-[3-(dimethylamino)propyl]-N'-ethylcarbodiimide
ent enantiomerically pure
eq. equivalent(s)
ESI electrospray ionization (in MS)
Et ethyl
h hour(s)
HATU N-[(dimethylamino)(3H-[1,2,3]triazolo[4,5-b]-pyridin-3-yloxy)methylene]-N-methylmethanaminium hexafluorophosphate
HOBT 1H-benzotriazol-1-ol
HPLC high-pressure, high-performance liquid chromatography
HRMS high-resolution mass spectrometry
ID internal diameter
conc. concentrated
LC-MS liquid chromatography-coupled mass spectrometry
LiHMDS lithium hexamethyldisilazide
m multiplet
Me methyl
min minute(s)
MS mass spectrometry
NMR nuclear magnetic resonance spectrometry
PDA photodiode array detector
$Pd_2dba_3$ tris(dibenzylideneacetone)dipalladium
Ph phenyl
q quartet (NMR coupling pattern)
quint. quintet (NMR coupling pattern)
rac racemic
rel relative stereochemistry
$R_F$ retention factor (in thin-layer chromatography)
RT room temperature
$R_t$ retention time (in HPLC)
s singlet (NMR coupling pattern)
t triplet (NMR coupling pattern)
THF tetrahydrofuran
TBTU (benzotriazol-1-yloxy)bisdimethylaminomethylium fluoroborate
UPLC-MS ultra-pressure liquid chromatography-coupled mass spectrometry
UV ultraviolet spectrometry
v/v volume to volume ratio (of a solution)
Xantphos 4,5-bis(diphenylphosphino)-9,9-dimethylxanthene
XPHOS dicyclohexyl(2',4',6'-triisopropylbiphenyl-2-yl)phosphine Unless stated otherwise, the percentages in the tests and examples which follow are percentages by weight; parts are parts by weight. Solvent ratios, dilution ratios and concentration data for liquid/liquid solutions are based in each case on volume. Details given for coupling patterns in NMR spectra are of a descriptive nature; coupling patterns of a higher order are not described as such.

LC/MS and HPLC Methods:

Method 1 (LC-MS):
Instrument: Waters ACQUITY SQD UPLC system; column: Waters Acquity UPLC HSS T3 1.8 μ 50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 210-400 nm.

Method 2 (LC-MS):
Instrument: Micromass Quattro Premier with Waters UPLC Acquity; column: Thermo Hypersil GOLD 1.9 μ 50 mm×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; flow rate: 0.33 ml/min; oven: 50° C.; UV detection: 210 nm.

Method 3 (LC-MS):
MS instrument type: Waters Micromass Quattro Micro; HPLC instrument type: Agilent 1100 series; column: Thermo Hypersil GOLD 3 μ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.

Method 4 (LC-MS):
MS instrument: Waters SQD; HPLC instrument: Waters UPLC; column: Zorbax SB-Aq (Agilent), 50 mm×2.1 mm, 1.8 μm; mobile phase A: water+0.025% formic acid, mobile phase B: acetonitrile (ULC)+0.025% formic acid; gradient: 0.0 min 98% A—0.9 min 25% A—1.0 min 5% A—1.4 min 5% A—1.41 min 98% A—1.5 min 98% A; oven: 40° C.; flow rate: 0.600 ml/min; UV detection: DAD; 210 nm.

Method 5 (LC-MS):
MS instrument: Waters ZQ 2000; HPLC instrument: Agilent 1100, 2-column system, autosampler: HTC PAL; column: YMC-ODS-AQ, 50 mm×4.6 mm, 3.0 μm; mobile phase A: water+0.1% formic acid, mobile phase B: acetonitrile+0.1% formic acid; gradient: 0.0 min 100% A—0.2 min 95% A—1.8 min 25% A—1.9 min 10% A—2.0 min 5% A—3.2 min 5% A—3.21 min 100% A—3.35 min 100% A; oven: 40° C.; flow rate: 3.0 ml/min; UV detection: 210 nm.

Method 6 (Preparative HPLC):
Column: Macherey-Nagel VP 50/21 Nucleosil 100-5 C18 Nautilus. Flow rate: 25 ml/min. Gradient: A=acetonitrile, B=water+0.1% formic acid, 0 min 10% A; 2.00 min 10% A; 6.00 min 90% A; 7.00 min 90% A; 7.10 min 10% A; 8 min 10% A; UV detection: 220 nm.

Method 7 (Preparative HPLC):
Column: Phenomenex Gemini C18; 110 A, AXIA, 5 μm, 21.2×50 mm 5 micron; gradient: A=water+0.1% conc. ammonia, B=acetonitrile, 0 min=10% B, 2 min=10% B, 6 min=90% B, 7 min=90% B, 7.1 min=10% B, 8 min=10% B, flow rate 25 ml/min, UV detection 220 nm.

Method 8 (Preparative HPLC):
Column: Axia Gemini 5μ C18 110 A, 50×21.5 mm, P/NO: 00B-4435-P0-AX, S/NO: 35997-2, gradient: A=water+0.1% conc. aq. ammonia, B=acetonitrile, 0 min=30% B, 2 min=30% B, 6 min=100% B, 7 min=100% B, 7.1 min=30% B, 8 min=30% B, flow rate 25 ml/min, UV detection 220 nm.

Method 9 (Preparative HPLC):

Column: Macherey-Nagel VP 50/21 Nucleosil 100-5 C18 Nautilus. Flow rate: 25 ml/min. Gradient: A=water+0.1% formic acid, B=methanol, 0 min=30% B, 2 min=30% B, 6 min=100% B, 7 min=100% B, 7.1 min=30% B, 8 min=30% B, flow rate 25 ml/min, UV detection 220 nm.

Method 10 (Preparative HPLC):

Column: Macherey-Nagel VP 50/21 Nucleosil 100-5 C18 Nautilus. Flow rate: 25 ml/min. Gradient: A=water+0.1% conc. aq. ammonia, B=methanol, 0 min=30% B, 2 min=30% B, 6 min=100% B, 7 min=100% B, 7.1 min=30% B, 8 min=30% B, flow rate 25 ml/min, UV detection 220 nm.

Method 11 (Preparative HPLC):

MS instrument: Waters, HPLC instrument: Waters (column Waters X-Bridge C18, 18 mm×50 mm, 5 μm, mobile phase A: water+0.05% triethylamine, mobile phase B: acetonitrile (ULC)+0.05% triethylamine, gradient: 0.0 min 95% A—0.15 min 95% A—8.0 min 5% A—9.0 min 5% A; flow rate: 40 ml/min; UV detection: DAD; 210-400 nm). or:

MS instrument: Waters, HPLC instrument: Waters (column Phenomenex Luna 5 μ C18(2) 100 A, AXIA Tech. 50×21.2 mm, mobile phase A: water+0.05% formic acid, mobile phase B: acetonitrile (ULC)+0.05% formic acid, gradient: 0.0 min 95% A—0.15 min 95% A—8.0 min 5% A—9.0 min 5% A; flow rate: 40 ml/min; UV detection: DAD; 210-400 nm).

Method 12 (LC-MS):

MS instrument: Waters SQD; HPLC instrument: Waters UPLC; column: Zorbax SB-Aq (Agilent), 50 mm×2.1 mm, 1.8 μm; mobile phase A: water+0.025% formic acid, mobile phase B: acetonitrile (ULC)+0.025% formic acid; gradient: 0.0 min 98% A—0.9 min 25% A—1.0 min 5% A—1.4 min 5% A—1.41 min 98% A—1.5 min 98% A; oven: 40° C.; flow rate: 0.600 ml/min; UV detection: DAD; 210 nm.

Method 13 (DCI-MS):

Instrument: DSQ II; Thermo Fisher-Scientific; DCI with NH₃, flow rate: 1.1 ml/min; source temperature: 200° C.; ionization energy 70 eV; heat DCI filament to 800° C.; mass range 80-900.

Method 14 (GC-MS):

Instrument: Micromass GCT, GC6890; column: Restek RTX-35, 15 m×200 μm×0.33 μm; constant helium flow rate: 0.88 ml/min; oven: 70° C.; inlet: 250° C.; gradient: 70° C., 30° C./min→310° C. (maintain for 3 min).

Method 15 (MS):

Instrument: Waters ZQ; ionization type: ESI (+); mobile phase; acetonitrile/water.

Method 16 (LCMS):

Instrument: Waters ACQUITY SQD UPLC system; column: Waters Acquity UPLC HSS T3 1.8 μ 30×2 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.60 ml/min; UV detection: 208-400 nm.

Method 17 (LC-MS):

Instrument: Micromass Quattro Premier with Waters UPLC Acquity; column: Thermo Hypersil GOLD 1.9 μ 50×1 mm; mobile phase A: 1 l of water+0.5 ml of 50% strength formic acid, mobile phase B: 1 l of acetonitrile+0.5 ml of 50% strength formic acid; gradient: 0.0 min 97% A→0.5 min 97% A→3.2 min 5% A→4.0 min 5% A; oven: 50° C.; flow rate: 0.3 ml/min; UV detection: 210 nm.

Unless stated otherwise, the percentages in the tests and examples which follow are percentages by weight; parts are parts by weight. Solvent ratios, dilution ratios and concentration data for liquid/liquid solutions are based in each case on volume.

The multiplicities of proton signals in ¹H NMR spectra reported in the paragraphs which follow represent the signal form observed in each case and do not take account of any higher-order signal phenomena. In all ¹H NMR spectra data, the chemical shifts δ are stated in ppm.

Additionally, the starting materials, intermediates and working examples may be present as hydrates. There was no quantitative determination of the water content. In certain cases, the hydrates may affect the ¹H NMR spectrum and possibly shift and/or significantly broaden the water signal in the ¹H NMR.

When compounds of the invention are purified by preparative HPLC by the above-described methods in which the mobile phases contain additives, for example trifluoroacetic acid, formic acid or ammonia, the compounds of the invention may be obtained in salt form, for example as trifluoroacetate, formate or ammonium salt, if the compounds of the invention contain a sufficiently basic or acidic functionality. Such a salt can be converted to the corresponding free base or acid by various methods known to the person skilled in the art.

In the case of the synthesis intermediates and working examples of the invention described hereinafter, any compound specified in the form of a salt of the corresponding base or acid is generally a salt of unknown exact stoichiometric composition, as obtained by the respective preparation and/or purification process. Unless specified in more detail, additions to names and structural formulae, such as "hydrochloride", "trifluoroacetate", "sodium salt" or "×HCl", "×CF₃CO₂H", "×Na⁺" should not therefore be understood in a stoichiometric sense in the case of such salts, but have merely descriptive character with regard to the salt-forming components present therein.

This applies correspondingly if synthesis intermediates or working examples or salts thereof were obtained in the form of solvates, for example hydrates, of unknown stoichiometric composition (if they are of a defined type) by the preparation and/or purification processes described.

STARTING COMPOUNDS AND INTERMEDIATES

Example 1A

3-[(2,6-Difluorobenzyl)oxy]pyridine-2-amine

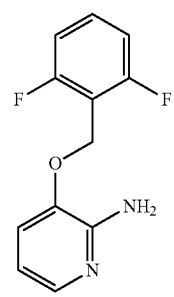 [SMILES: Nc1ncccc1OCc1c(F)cccc1F]

At RT, 51 g of sodium methoxide (953 mmol, 1.05 equivalents) were initially charged in 1000 ml of methanol, 100 g of 2-amino-3-hydroxypyridine (908 mmol, 1 equivalent) were added and the mixture was stirred at RT for 15 min. The reaction mixture was concentrated under reduced pressure, the residue was taken up in 2500 ml of DMSO and 197 g of 2,6-difluorobenzyl bromide (953 mmol, 1.05 equivalents) were added. After 4 h at RT, the reaction mixture was added to 20 l of water, the mixture was stirred for a further 15 min and the solid was filtered off. The solid was washed with 1 l of water and 100 ml of isopropanol and 500 ml of petroleum ether and dried under high vacuum. This gave 171 g of the title compound (78% of theory).

$^1$H-NMR (400 Mhz, DMSO-$d_6$): δ=5.10 (s, 2 H), 5.52 (br. s, 2 H), 6.52 (dd, 1 H), 7.16-7.21 (m, 3 H), 7.49-7.56 (m, 2 H).

Example 2A

Ethyl 8-[(2,6-difluorobenzyl)oxy]-2-methylimidazo[1,2-a]pyridine-3-carboxylate

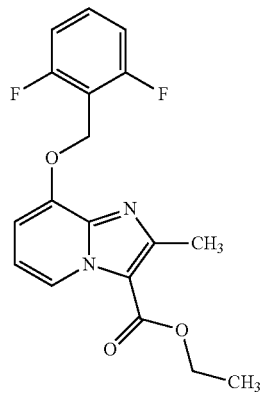 [SMILES: CCOC(=O)c1c(C)nc2c(OCc3c(F)cccc3F)cccn12]

170 g of 3-[(2,6-difluorobenzyl)oxy]pyridine-2-amine (Example 1A; 719 mmol, 1 equivalent) were initially charged in 3800 ml of ethanol, and 151 g of powdered molecular sieve 3 Å and 623 g of ethyl 2-chloroacetoacetate (3.6 mol, 5 equivalents) were added. The reaction mixture was heated at reflux for 24 h and then filtered off through silica gel and concentrated under reduced pressure. The mixture was kept at RT for 48 h and the solid formed was filtered off. The solid was then stirred three times with a little isopropanol and then filtered off, and washed with diethyl ether. This gave 60.8 g (23% of theory) of the title compound. The combined filtrates of the filtration steps were concentrated and the residue was chromatographed on silica gel using the mobile phase cyclohexane/diethyl ether. This gave a further 46.5 g (18% of theory; total yield: 41% of theory) of the title compound.

LC-MS (Method 1): $R_t$=1.01 min

MS (ESpos): m/z=347 (M+H)$^+$ $^1$H-NMR (400 Mhz, DMSO-$d_6$): δ=1.36 (t, 3 H), 2.54 (s, 3 H; obscured by DMSO signal), 4.36 (q, 2 H), 5.33 (s, 2 H), 7.11 (t, 1 H), 7.18-7.27 (m, 3 H), 7.59 (quint, 1 H), 8.88 (d, 1 H).

Example 3A

8-[(2,6-Difluorobenzyl)oxy]-2-methylimidazo[1,2-a]pyridine-3-carboxylic acid

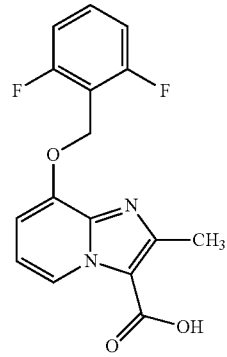 [SMILES: Cc1nc2c(OCc3c(F)cccc3F)cccn2c1C(=O)O]

107 g of ethyl 8-[(2,6-difluorobenzyl)oxy]-2-methylimidazo[1,2-a]pyridine-3-carboxylate (Example 2A; 300 mmol, 1 equivalent) were dissolved in 2.8 l of THF/methanol (1:1), 1.5 l of 1 N aqueous lithium hydroxide solution (1.5 mol, 5 equivalents) were added and the mixture was stirred at RT for 16 h. The organic solvents were removed under reduced pressure and the resulting aqueous solution was, in an ice bath, adjusted to pH 3-4 using 1 N aqueous hydrochloric acid. The resulting solid was filtered off, washed with water and isopropanol and dried under reduced pressure. This gave 92 g (95% of theory) of the title compound.

LC-MS (Method 1): $R_t$=0.62 min

MS (ESpos): m/z=319.1 (M+H)$^+$ $^1$H-NMR (400 Mhz, DMSO-$d_6$): δ=2.55 (s, 3 H; superposed by DMSO signal), 5.32 (s, 2 H); 7.01 (t, 1 H), 7.09 (d, 1 H), 7.23 (t, 2 H), 7.59 (quint, 1 H), 9.01 (d, 1 H).

Example 4A 3-(Cyclohexylmethoxy)pyridine-2-amine

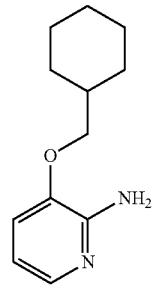 [SMILES: Nc1ncccc1OCC1CCCCC1]

At RT, 96 g of sodium hydroxide, 45% strength in water (1081 mmol, 1 equivalent), were initially charged in 1170 ml of methanol, 119 g of 2-amino-3-hydroxypyridine (1080 mmol, 1 equivalent) were added and the mixture was stirred at RT for another 10 min. The reaction mixture was concentrated under reduced pressure, the residue was taken up in 2900 ml of DMSO and 101 g of cyclohexylmethyl bromide (1135 mmol, 1.05 equivalents) were added. After 16 h at RT, the reaction mixture was slowly added to 6 l of water and the aqueous solution was extracted twice with in each case 2 l of ethyl acetate. The combined organic phases were washed with in each case 1 l of saturated aqueous sodium bicarbonate solution and water, dried, filtered and concentrated. The residue was stirred with 500 ml of n-pentane, filtered and dried under reduced pressure. This gave 130 g (58% of theory) of the title compound.

LC-MS (Method 3): $R_t$=1.41 min

MS (ESpos): m/z=207.1 (M+H)$^+$

Example 5A

Ethyl 8-(cyclohexylmethoxy)-2-methylimidazo[1,2-a]pyridine-3-carboxylate

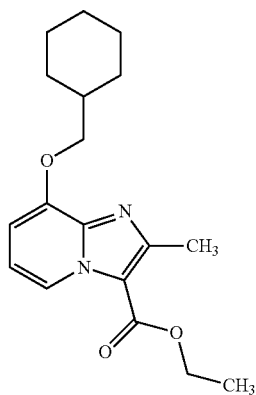 [SMILES: CCOC(=O)c1c(C)nc2c(OCC3CCCCC3)cccn12]

130 g of 3-(cyclohexylmethoxy)pyridine-2-amine (Example 4A; 630 mmol, 1 equivalent) were initially charged in 3950 ml of ethanol, and 436 ml of ethyl 2-chloroacetoacetate (3.2 mol, 5 equivalents) were added. The mixture was heated at reflux for 24 h and then concentrated under reduced pressure. The crude product thus obtained was chromatographed on silica gel using the mobile phase cyclohexane/diethyl ether, giving 66.2 g (33% of theory) of the title compound.

LC-MS (Method 1): $R_t$=1.17 min

MS (ESpos): m/z=317.1 (M+H)$^+$ $^1$H-NMR (400 Mhz, DMSO-d$_6$): δ=1.02-1.31 (m, 5 H), 1.36 (t, 3 H), 1.64-1.77 (m, 3 H), 1.79-1.90 (m, 3 H), 2.60 (s, 3 H), 3.97 (d, 2 H), 4.35 (q, 2 H), 6.95 (d, 1 H), 7.03 (t, 1 H), 8.81 (d, 1 H).

Example 6A 8-(Cyclohexylmethoxy)-2-methylimidazo[1,2-a]pyridine-3-carboxylic acid

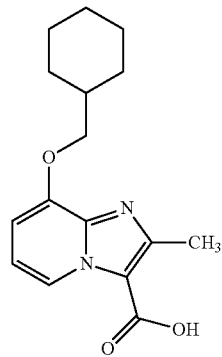 [SMILES: Cc1nc2c(OCC3CCCCC3)cccn2c1C(=O)O]

50 g of ethyl 8-(cyclohexylmethoxy)-2-methylimidazo[1,2-a]pyridine-3-carboxylate (Example 5A; 158 mmol, 1 equivalent) were dissolved in 600 ml of 1,4-dioxane, 790 ml of 2 N aqueous sodium hydroxide solution (1.58 mol, 10 equivalents) were added and the mixture was stirred at RT for 16 h. 316 ml of 6 N aqueous hydrochloric acid were added and the mixture was concentrated to about ⅕ of the total volume. The resulting solid was filtered off, washed with water and tert-butyl methyl ether and dried under reduced pressure. This gave 35 g (74% of theory) of the title compound.

LC-MS (Method 1): $R_t$=0.81 min

MS (ESpos): m/z=289.0 (M+H)$^+$ $^1$H-NMR (400 Mhz, DMSO-d$_6$): δ=1.03-1.44 (m, 5 H), 1.64-1.78 (m, 3 H), 1.81-1.92 (m, 3 H), 2.69 (s, 3 H), 4.07 (d, 2 H), 7.30-7.36 (m, 2 H), 9.01 (d, 1 H).

Example 7A

5-Bromo-3-[(2,6-difluorobenzyl)oxy]pyridine-2-amine

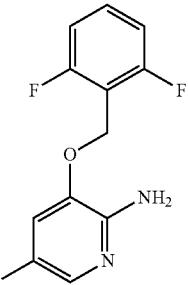

32.6 g of 3-[(2,6-difluorobenzyl)oxy]pyridine-2-amine (Example 1A; 138 mmol, 1 equivalent) were suspended in 552 ml of 10% strength sulfuric acid, and the mixture was cooled to 0° C. 8.5 ml of bromine (165 mmol, 1.2 equivalents) were dissolved in 85 ml of acetic acid and then, over 90 min, added dropwise to the reaction solution, cooled with ice. After the addition had ended, the mixture was stirred at 0° C. for 90 min and then diluted with 600 ml of ethyl acetate, and the aqueous phase was separated off. The aqueous phase was extracted with ethyl acetate. The organic phases were combined, washed with saturated aqueous sodium bicarbonate solution, dried and concentrated. The residue was dissolved in dichloromethane and chromatographed on silica gel (petroleum ether/ethyl acetate gradient as mobile phase). This gave 24 g (55% of theory) of the title compound.

LC-MS (Method 1): $R_t$=0.96 min

MS (ESpos): m/z=315.1/317.1 (M+H)$^+$ $^1$H-NMR (400 Mhz, DMSO-d$_6$): δ=5.14 (s, 2 H), 5.83 (br. s, 2 H), 7.20 (t, 2 H), 7.42 (d, 1 H), 7.54 (q, 1 H), 7.62 (d, 1 H).

Example 8A

Ethyl 6-bromo-8-[(2,6-difluorobenzyl)oxy]-2-methylimidazo[1,2-a]pyridine-3-carboxylate

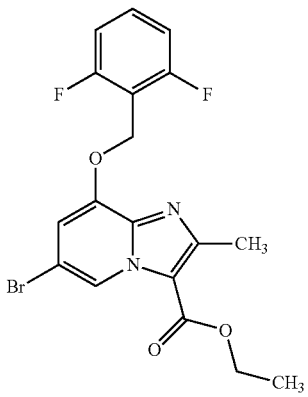 [SMILES: CCOC(=O)c1c(C)nc2c(OCc3c(F)cccc3F)cc(Br)cn12]

16 g of powdered molecular sieve 3 Å and 52.7 ml of ethyl 2-chloroacetoacetate (380.8 mmol, 5 equivalents) were added to 24 g of 5-bromo-3-[(2,6-difluorobenzyl)oxy]pyridine-2-amine (Example 7A; 76.2 mmol; 1 equivalent) in 400 ml of ethanol, and the mixture was heated at reflux overnight. 8 g of molecular sieve were added and the mixture was heated at reflux for a further 24 h. The reaction mixture was concentrated under reduced pressure, and the residue was taken up in dichloromethane and chromatographed on silica gel (mobile phase: dichloromethane/methanol 20:1). The product-containing fractions were concentrated and the residue was stirred with 100 ml of diethyl ether for 30 min. The solid was then filtered off, washed with a little diethyl ether and dried. This gave 15 g (45% of theory) of the title compound.

LC-MS (Method 2): $R_t$=1.43 min

MS (ESpos): m/z=414.9/416.8 (M+H)$^+$ $^1$H-NMR (400 Mhz, DMSO-$d_6$): δ=1.36 (t, 3 H), 2.54 (s, 3 H; obscured by DMSO signal), 4.37 (q, 2 H), 5.36 (s, 2 H), 7.25 (t, 2 H), 7.42 (d, 1 H), 7.61 (q, 1 H), 9.00 (d, 1 H).

Example 9A

6-Bromo-8-[(2,6-difluorobenzyl)oxy]-2-methylimidazo[1,2-a]pyridine-3-carboxylic acid

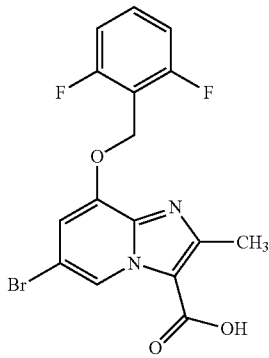 [SMILES: Cc1nc2c(OCc3c(F)cccc3F)cc(Br)cn2c1C(=O)O]

1.5 g of ethyl 6-bromo-8-[(2,6-difluorobenzyl)oxy]-2-methylimidazo[1,2-a]pyridine-3-carboxylate (Example 8A; 3.5 mmol, 1 equivalent) were dissolved in 72 ml of THF/methanol 5:1, 17.6 ml of 1N aqueous lithium hydroxide solution (17.6 mmol, 5 equivalents) were added and the mixture was warmed to 40° C. and stirred at this temperature for 6 h. Using 6 N aqueous hydrochloric acid, the mixture was then adjusted to pH 4 and concentrated under reduced pressure. Water was added to the solid formed, the mixture was stirred and the product was filtered off, washed with water and dried under reduced pressure. This gave 1.24 g of the title compound (88% of theory).

LC-MS (Method 1): $R_t$=0.93 min

MS (ESpos): m/z=397.0/399.1 (M+H)$^+$ $^1$H-NMR (400 Mhz, DMSO-$d_6$): δ=2.54 (s, 3 H; superposed by DMSO signal); 5.36 (s, 2 H); 7.25 (t, 2 H); 7.40 (d, 1 H); 7.61 (q, 1 H); 9.06 (d, 1 H); 13.35 (br. s, 1 H).

Example 10A

Ethyl 8-[(2,6-difluorobenzyl)oxy]-2,6-dimethylimidazo[1,2-a]pyridine-3-carboxylate

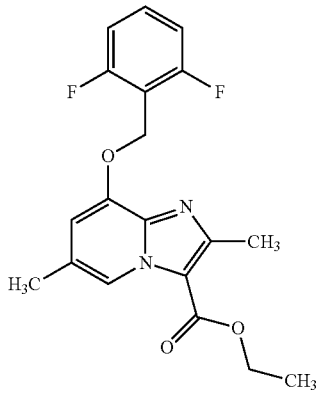 [SMILES: CCOC(=O)c1c(C)nc2c(OCc3c(F)cccc3F)cc(C)cn12]

Method 1:

600 mg of ethyl 6-bromo-8-[(2,6-difluorobenzyl)oxy]-2-methylimidazo[1,2-a]pyridine-3-carboxylate (Example 8A; 1.4 mmol, 1 equivalent) and 230 mg of 1,1'-bis(diphenylphosphino)ferrocenepalladium(II) dichloride/dichloromethane complex (0.282 mmol, 20 mol %) were dissolved in 25 ml of THF, and 0.88 ml (1.76 mmol, 1.2 equivalents) of a 2 M solution of methylzinc chloride in THF was added. In a microwave, the reaction mixture was heated at 100° C. for 40 min. The reaction mixture was filtered through Celite and then concentrated under reduced pressure. The residue was chromatographed (Biotage Isolera Four; cyclohexane:ethyl acetate). 225 mg (38% of theory) of the title compound were obtained.

Method 2:

20.00 g (85.38 mmol) of ethyl 8-hydroxy-2,6-dimethylimidazo[1,2-a]pyridine-3-carboxylate from Example 15A, 19.44 g (93.91 mmol) of 2,6-difluorobenzyl bromide and 61.20 g (187.83 mmol) of caesium carbonate in 1.18 l of DMF were stirred at 60° C. for 5 h. The reaction mixture was then added to 6.4 l of 10% strength aqueous sodium chloride solution and then twice extracted with ethyl acetate. The combined organic phases were washed with 854 ml of 10% strength aqueous sodium chloride solution, dried, concentrated and dried at RT under high vacuum overnight. This gave 28.2 g (92% of theory; purity: 90%) of the title compound.

LC-MS (Method 1): $R_t$=1.05 min

MS (ESpos): m/z=361.1 (M+H)$^+$ $^1$H-NMR (400 Mhz, DMSO-d$_6$): δ=1.38 (t, 3 H), 2.36 (s, 3 H), 4.35 (q, 2 H), 5.30 (s, 2 H), 7.10 (s, 1 H), 7.23 (t, 2 H), 7.59 (q, 1 H), 8.70 (s, 1 H).

Example 11A

8-[(2,6-Difluorobenzyl)oxy]-2,6-dimethylimidazo[1,2-a]pyridine-3-carboxylic acid

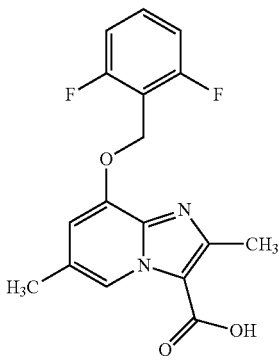

220 mg of ethyl 8-[(2,6-difluorobenzyl)oxy]-2,6-dimethylimidazo[1,2-a]pyridine-3-carboxylate (Example 10A; 0.524 mmol, 1 equivalent) were dissolved in 7 ml of THF/methanol 1:1, 2.6 ml of 1 N aqueous lithium hydroxide solution (2.6 mmol, 5 equivalents) were added and the mixture was stirred at RT for 16 h. The mixture was concentrated under reduced pressure and the residue was acidified with 1N aqueous hydrochloric acid and stirred for 15 min. The solid was filtered off, washed with water and dried under reduced pressure. This gave 120 mg of the title compound (60% of theory).

LC-MS (Method 1): $R_t$=0.68 min

MS (ESpos): m/z=333.1 (M+H)$^+$ $^1$H-NMR (400 Mhz, DMSO-d$_6$): δ=2.34 (s, 3 H), 5.28 (s, 2 H), 7.09 (s, 1 H), 7.23 (t, 2 H), 7.58 (q, 1 H), 8.76 (s, 1 H), 13.1 (br. s, 1 H).

Example 12A 3-(Benzyloxy)-5-bromopyridine-2-amine

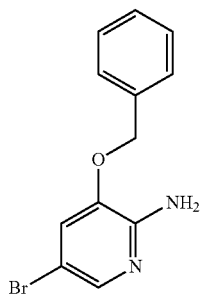 [SMILES: Nc1ncc(Br)cc1OCc1ccccc1]

The target compound is known from the literature and described:

1) Palmer, A. M. et al. J Med. Chem. 2007, 50, 6240-6264.
2) ALTANA WO2005/58325
3) ALTANA WO2005/90358
4) Cui, J. T. et al. J Med. Chem. 2011, 54, 6342-6363

Further Preparation Method:

200 g (1 mol) of 2-amino-3-benzyloxypyridine were initially charged in 4 l of dichloromethane, and at 0° C. a solution of 62 ml (1.2 mol) of bromine in 620 ml of dichloromethane was added over 30 min. After the addition had ended, the reaction solution was stirred at 0° C. for 60 min. About 4 l of saturated aqueous sodium bicarbonate solution were then added to the mixture. The organic phase was removed and concentrated. The residue was purified by silica gel column chromatography (petroleum ether:ethyl acetate 6:4) and the product fractions were concentrated. This gave 214 g (77% of theory) of the title compound.

LC-MS (Method 1): $R_t$=0.92 min

MS (ESpos): m/z=279 (M+H)$^+$ $^1$H-NMR (400 Mhz, DMSO-d$_6$): δ=5.16 (s, 2H), 5.94-6.00 (m, 2H), 7.26-7.29 (m, 1H), 7.31-7.36 (m, 1H), 7.37-7.43 (m, 2H), 7.47-7.52 (m, 2H), 7.57-7.59 (m, 1H).

Example 13A

Ethyl 8-(benzyloxy)-6-bromo-2-methylimidazo[1,2-a]pyridine-3-carboxylate

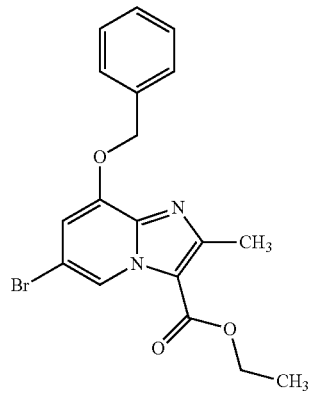 [SMILES: CCOC(=O)c1c(C)nc2c(OCc3ccccc3)cc(Br)cn12]

Under argon, 200 g (0.72 mol) of 3-(benzyloxy)-5-bromopyridine-2-amine from Example 12A, 590 g (3.58 mol) of ethyl 2-chloroacetoacetate and 436 g of 3 A molecular sieve were suspended in 6 l of ethanol, and the suspension was stirred at reflux for 72 h. The reaction mixture was filtered off through silica gel and concentrated. The residue was purified by silica gel chromatography (petroleum ether:ethyl acetate 9:1, then 6:4) and the product fractions were concentrated. This gave 221 g (79% of theory) of the target compound.

LC-MS (Method 16): $R_t$=1.31 min

MS (ESpos): m/z=389 (M+H)$^+$ $^1$H-NMR (400 Mhz, DMSO-d$_6$): δ=1.36 (t, 3 H), 2.58 (s, 3 H), 4.32-4.41 (m, 2 H), 5.33 (s, 2 H), 7.28-7.32 (m, 1 H), 7.36-7.47 (m, 3 H), 7.49-7.54 (m, 2 H), 8.98 (d, 1 H).

Example 14A

Ethyl 8-(benzyloxy)-2,6-dimethylimidazo[1,2-a]pyridine-3-carboxylate

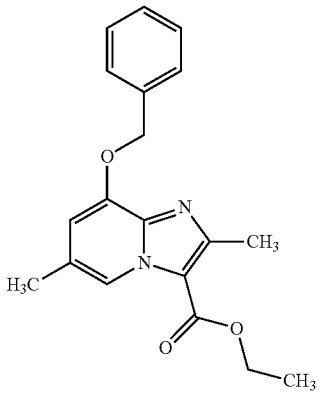 [SMILES: CCOC(=O)c1c(C)nc2c(OCc3ccccc3)cc(C)cn12]

Under argon, 105 g (270 mmol) of ethyl 8-(benzyloxy)-6-bromo-2-methylimidazo[1,2-a]pyridine-3-carboxylate from Example 13A were suspended in 4.2 l of 1,4-dioxane, and 135.4 g (539 mmol, purity 50%) of trimethylboroxine, 31.2 g (27 mmol) of tetrakis(triphenylphosphine)palladium (0) and 78.3 g (566 mmol) of potassium carbonate were added in succession and the mixture was stirred under reflux for 8 h. The reaction mixture was cooled to RT and, using silica gel, freed from the precipitate by filtration, and the filtrate was concentrated. The residue was dissolved in dichloromethane and purified by silica gel chromatography (dichloromethane:ethyl acetate=9:1). This gave 74 g (84.6% of theory) of the target compound.

LC-MS (Method 16): $R_t$=1.06 min
MS (ESpos): m/z=325 (M+H)$^+$
$^1$H-NMR (400 Mhz, DMSO-d$_6$): δ=1.35 (t, 3 H), 2.34 (br. s, 3 H), 2.56 (s, 3 H), 4.31-4.38 (m, 2 H), 5.28 (br. s, 2 H), 6.99-7.01 (m, 1 H), 7.35-7.47 (m, 3 H), 7.49-7.54 (m, 2 H), 8.68-8.70 (m, 1 H).

Example 15A

Ethyl 8-hydroxy-2,6-dimethylimidazo[1,2-a]pyridine-3-carboxylate

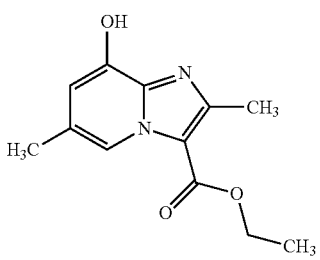 [SMILES: CCOC(=O)c1c(C)nc2c(O)cc(C)cn12]

74 g (228 mmol) of ethyl 8-(benzyloxy)-2,6-dimethylimidazo[1,2-a]pyridine-3-carboxylate from Example 14A were initially charged in 1254 ml of dichloromethane and 251 ml of ethanol, and 20.1 g of 10% palladium on activated carbon (moist with water, 50%) were added under argon. The reaction mixture was hydrogenated at RT and under standard pressure overnight. The reaction mixture was filtered off through silica gel and concentrated. The crude product was purified by silica gel chromatography (dichloromethane:methanol=95:5). This gave 50.4 g (94% of theory) of the target compound.

DCI-MS: (Method 13) (ESpos): m/z=235.2 (M+H)$^+$
$^1$H-NMR (400 Mhz, DMSO-d$_6$): δ=1.35 (t, 3 H), 2.27 (s, 3 H), 2.58 (s, 3 H), 4.30-4.38 (m, 2 H), 6.65 (d, 1 H), 8.59 (s, 1 H), 10.57 (br. s, 1H).

Example 16A

Ethyl 2,6-dimethyl-8-[(2,3,6-trifluorobenzyl)oxy]imidazo[1,2-a]pyridine-3-carboxylate

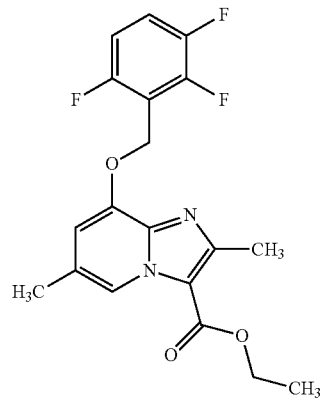 [SMILES: CCOC(=O)c1c(C)nc2c(OCc3c(F)ccc(F)c3F)cc(C)cn12]

3.00 g (12.81 mmol) of ethyl 8-hydroxy-2,6-dimethylimidazo[1,2-a]pyridine-3-carboxylate Example 15A, 3.27 g (14.1 mmol) of 2-(bromomethyl)-1,3,4-trifluorobenzene and 9.18 g (28.17 mmol) of caesium carbonate were initially charged in 183 ml of dry DMF, and the mixture was heated in an oil bath at 60° C. for 30 min. About 1.8 l of water were then added, and the mixture was stirred for 30 min. The solid was filtered off, washed with water and dried under reduced pressure. This gave 5.07 g of the title compound (99% of theory).

LC-MS (Method 1): $R_t$=1.14 min
MS (ESpos): m/z=379 (M+H)$^+$
$^1$H-NMR (400 Mhz, DMSO-d$_6$): δ=1.35 (t, 3 H), 2.36 (s, 3 H); 2.55 (s, 3 H; superposed by DMSO signal), 4.36 (q, 2 H), 5.35 (s, 2 H), 7.09 (s, 1 H), 7.22-7.32 (m, 1 H), 7.60-7.73 (m, 1 H), 8.72 (s, 1 H).

Example 17A 2,6-Dimethyl-8-[(2,3,6-trifluorobenzyl)oxy]imidazo[1,2-a]pyridine-3-carboxylic acid

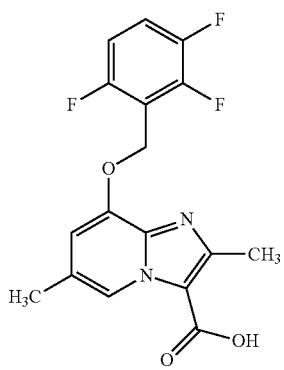

5.07 g (12.87 mmol) of ethyl 2,6-dimethyl-8-[(2,3,6-trifluorobenzyl)oxy]imidazo[1,2-a]pyridine-3-carboxylate Example 16A were dissolved in 275 ml of THF/methanol (5/1), 64.4 ml of 1 N aqueous lithium hydroxide solution were added and the mixture was stirred at 40° C. for 3.5 h. At 0° C., the reaction was brought to a pH of about 4 using 6 N aqueous hydrochloric acid and then concentrated. The solid obtained was filtered off, washed with water and dried under reduced pressure. This gave 4.77 g (98% of theory; purity about 93%) of the title compound.

LC-MS (Method 1): $R_t$=0.72 min

MS (ESpos): m/z=351 (M+H)$^+$ $^1$H-NMR (400 Mhz, DMSO-d$_6$): δ=2.37 (s, 3 H), 2.54 (s, 3 H; superposed by DMSO signal), 5.36 (s, 2 H), 7.11 (s, 1 H), 7.25-7.33 (m, 1 H), 7.61-7.73 (m, 1 H), 8.78 (s, 1 H), 13.10 (br. s, 1 H).

Example 18A

8-[(2,6-Difluorobenzyl)oxy]-2-methylimidazo[1,2-a]pyridine

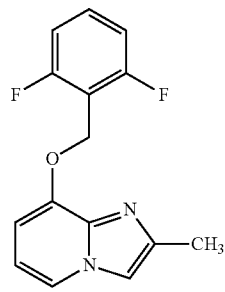 [SMILES: Cc1cn2cccc(OCc3c(F)cccc3F)c2n1]

12 g of 3-[(2,6-difluorobenzyl)oxy]pyridine-2-amine (Example 1A, 50.8 mmol, 1 equivalent) and 8 g of 1-chloroacetone (86.4 mmol, 1.7 equivalents) in 90 ml of ethanol were stirred at 80° C. overnight. Silica gel was added and the reaction mixture was concentrated. The residue was purified by silica gel chromatography (mobile phase mixture dichloromethane/ethanol=50:1). The product mixture obtained was then purified by silica gel chromatography (mobile phase mixture dichloromethane/ethanol/diethylamine=50:1:0.1, 40:1:0.5, 30:1:0.5). This gave 6.3 g (45% of theory) of the title compound.

LC-MS (Method 1): $R_t$=0.58 min

MS (ESpos): m/z=274 (M+H)$^+$ $^1$H-NMR (400 Mhz, DMSO-d$_6$): δ=2.27 (s, 3 H), 5.27 (s, 2 H), 6.69-6.80 (m, 2 H), 7.23 (s, 2 H), 7.51-7.62 (m, 1 H), 7.65 (s, 1 H), 8.03-8.12 (m, 1 H).

Example 19A

3-Bromo-8-[(2,6-difluorobenzyl)oxy]-2-methylimidazo[1,2-a]pyridine

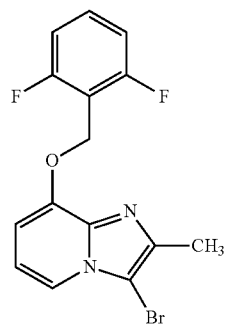 [SMILES: Cc1nc2c(OCc3c(F)cccc3F)cccn2c1Br]

193 g of 8-[(2,6-difluorobenzyl)oxy]-2-methylimidazo[1,2-a]pyridine (Example 18A, 0.7 mmol, 1 equivalent) were initially charged in 2.2 l of ethanol, and 150.3 g of N-bromosuccinimide (0.8 mmol, 1.2 equivalents) were added. After 1.5 h at RT, the mixture was concentrated under reduced pressure at RT. The residue was then diluted with ethyl acetate, and the organic phase was washed with saturated aqueous sodium hydrogencarbonate solution, dried over sodium sulfate, filtered and concentrated by rotary evaporation. The residue was purified by silica gel chromatography (mobile phase mixture cyclohexane/ethyl acetate=98:2, 96:4, 92:8, 9:1, 8:2 and 7:3). The product obtained was stirred with 600 ml of ethyl acetate and decanted off. The residue was dried under reduced pressure. 23.4 g (9% of theory) of the title compound were obtained.

The filtrate was concentrated under reduced pressure and the residue was stirred with 100 ml of ethyl acetate. The ethyl acetate phase was decanted off and the residue was dried under reduced pressure. This gave a further 6.1 g (2.3% of theory) of the title compound.

LC-MS (Method 1): $R_t$=0.90 min

MS (ESpos): m/z=353 (M+H)$^+$ $^1$H-NMR (400 Mhz, DMSO-d$_6$): δ=2.27 (s, 3 H), 5.27 (s, 2 H), 6.70-6.80 (m, 2 H), 7.23 (t, 2 H), 7.52-7.62 (m, 1 H), 7.65 (s, 1 H), 8.09 (d, 1 H).

Example 20A

8-[(2,6-Difluorobenzyl)oxy]-2,6-dimethylimidazo[1,2-a]pyridine

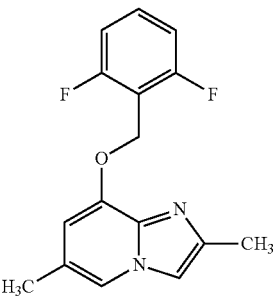

10.0 g (30.09 mmol) of 8-[(2,6-difluorobenzyl)oxy]-2,6-dimethylimidazo[1,2-a]pyridine-3-carboxylic acid from Example 11A were initially charged in 228 ml of dioxane, 25.1 ml of 6 N aqueous hydrochloric acid solution were added and the mixture was stirred at 100° C. for 2 h. After cooling, dioxane was removed under reduced pressure and the aqueous residue was adjusted to pH 8 using 2 N aqueous sodium hydroxide solution. The solid obtained was filtered off, washed with water and dried under high vacuum. This gave 8.97 g of the target compound (97% of theory, purity 94%).

LC-MS (Method 1): $R_t$=0.70 min

MS (ESpos): m/z=289 (M+H)$^+$ $^1$H-NMR (400 Mhz, DMSO-d$_6$): δ=2.22-2.30 (m, 6 H); 5.27 (s, 2 H); 6.67 (s, 1 H); 7.21 (t, 2 H); 7.53-7.63 (m, 2 H); 7.89 (s, 1 H).

Example 21A

3-Bromo-8-[(2,6-difluorobenzyl)oxy]-2,6-dimethylimidazo[1,2-a]pyridine

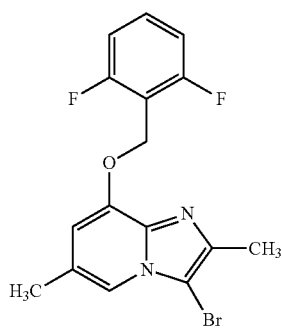

Under argon and with exclusion of light, 3.865 g (13.41 mmol) of 8-[(2,6-difluorobenzyl)oxy]-2,6-dimethylimidazo[1,2-a]pyridine from Example 20A were initially charged in 42 ml of ethanol, 2.625 g (14.75 mmol) of N-bromosuccinimide were added and the mixture was stirred at room temperature for 4 h. The reaction mixture was concentrated. The residue was stirred with about 100 ml of water, and the resulting suspension was then stirred at RT for 30 min. The precipitate formed was filtered off, washed with water and dried under high vacuum. This gave 4.48 g of the target compound (91% of theory).

LC-MS (Method 1): $R_t$=0.93 min

MS (ESpos): m/z=267 (M+H)$^+$ $^1$H-NMR (400 Mhz, DMSO-d$_6$): δ=2.28 (s, 3 H), 2.33 (s, 3 H); 5.30 (s, 2 H); 6.89 (s, 1 H); 7.22 (t, 2 H); 7.53-7.63 (m, 1 H); 7.75 (s, 1 H).

Example 22A 2,6-Dimethyl-8-[(2,3,6-trifluorobenzyl)oxy]imidazo[1,2-a]pyridine

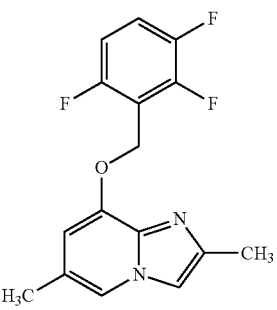

6.48 g (18.50 mmol) of 2,6-dimethyl-8-[(2,3,6-trifluorobenzyl)oxy]imidazo[1,2-a]pyridine-3-carboxylic acid from Example 17A were initially charged in 140 ml of dioxane, 15.4 ml of 6 N aqueous hydrochloric acid solution were added and the mixture was stirred at 100° C. for 4 h. After cooling, the dioxane was removed under reduced pressure and the aqueous residue was adjusted to pH 8 using 1 N aqueous sodium hydroxide solution. The solid formed was filtered off, washed with water and dried under high vacuum. This gave 5.57 g of the target compound (96% of theory).

LC-MS (Method 1): $R_t$=0.65 min

MS (ESpos): m/z=307 (M+H)$^+$ $^1$H-NMR (400 Mhz, DMSO-d$_6$): δ=2.20-2.29 (m, 6 H), 5.29 (s, 2 H), 6.69 (s, 1 H), 7.23-7.33 (m, 1 H), 7.57 (s, 1 H), 7.60-7.73 (m, 1 H), 7.91 (s, 1 H).

Example 23A

3-Bromo-2,6-dimethyl-8-[(2,3,6-trifluorobenzyl)oxy]imidazo[1,2-a]pyridine

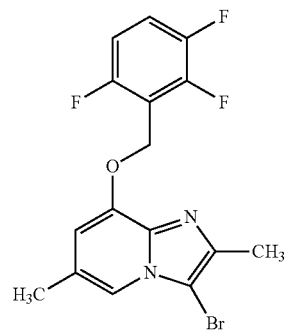

Under argon and with exclusion of light, 2.28 g (7.45 mmol) of 2,6-dimethyl-8-[(2,3,6-trifluorobenzyl)oxy]imidazo[1,2-a]pyridine from Example 22A were initially charged in 23.4 ml of ethanol, 1.46 g (8.20 mmol) of N-bromosuccinimide were added and the mixture was stirred at room temperature for 1.5 h. The reaction mixture was concentrated under reduced pressure. The residue was stirred with 200 ml of water, and the resulting suspension was then stirred at RT for 2 h. The precipitate formed was filtered off, washed with water and dried under high vacuum. This gave 2.47 g of the target compound (86% of theory).

LC-MS (Method 1): $R_t$=0.97 min

MS (ESpos): m/z=385 (M+H)$^+$ $^1$H-NMR (400 Mhz, DMSO-d$_6$): δ=2.28 (s, 3 H), 2.33 (s, 3 H); 5.32 (s, 2 H); 6.87 (s, 1 H); 7.24-7.33 (m, 1 H); 7.62-7.73 (m, 1 H); 7.76 (s, 1 H).

Example 24A

8-[(2,6-Difluorobenzyl)oxy]-2-methylimidazo[1,2-a]pyridine-3-carboxamide

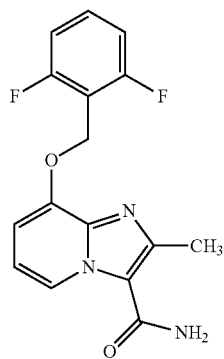 [SMILES: Cc1nc2c(OCc3c(F)cccc3F)cccn2c1C(N)=O]

Under argon, 5 g of 8-[(2,6-difluorobenzyl)oxy]-2-methylimidazo[1,2-a]pyridine-3-carboxylic acid (Example 3A, 15.7 mmol, 1 equivalent) were initially charged in 300 ml of dichloromethane, 4.5 g of 1-(3-dimethylaminopropyl)-3-ethylcarbodiimide hydrochloride (23.6 mmol, 1.5 equivalents) and 3.6 g of 1-hydroxy-1H-benzotriazole hydrate (HOBT, 23.6 mmol, 1.5 equivalents) were added successively at RT and the mixture was stirred at RT for 10 min. 4.2 g of ammonium chloride (78.5 mmol, 5 equivalents) and 19.2 ml of N,N-diisopropylethylamine (109.9 mmol, 7 equivalents) were then added, and the mixture was stirred at RT overnight. The mixture was concentrated by rotary evaporation, dichloromethane was added to the residue, the mixture was filtered, the filter cake was washed with dichloromethane and the product was dried under reduced pressure overnight.

This gave 5.38 g (108% of theory) of the title compound which was reacted further without purification.

LC-MS (Method 1): $R_t$=0.65 min

MS (ESpos): m/z=318.2 (M+H)$^+$

Example 25A

8-[(2,6-Difluorobenzyl)oxy]-2-methylimidazo[1,2-a]pyridine-3-carbonitrile

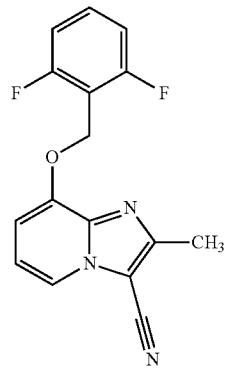 [SMILES: Cc1nc2c(OCc3c(F)cccc3F)cccn2c1C#N]

912 mg of 8-[(2,6-difluorobenzyl)oxy]-2-methylimidazo[1,2-a]pyridine-3-carboxamide (Example 24A, 2.9 mmol, 1 equivalent) were initially charged in 13 ml of THF, and 0.6 ml of pyridine (7.4 mmol, 2.56 equivalents) was added. Subsequently, 1.04 ml (7.4 mmol, 2.56 equivalents) of trifluoroacetic anhydride were added dropwise and the mixture was stirred at RT overnight. Subsequently, the mixture was added to water and extracted three times with ethyl acetate. The combined organic phases were washed once with saturated aqueous sodium bicarbonate solution, once with 1 N aqueous hydrochloric acid and once with saturated sodium chloride solution, dried over sodium sulfate and concentrated on a rotary evaporator. The residue was dried under reduced pressure overnight. This gave 787 mg (91% of theory) of the title compound.

LC-MS (Method 1): $R_t$=0.97 min

MS (ESpos): m/z=300.1 (M+H)$^+$ $^1$H-NMR (400 Mhz, DMSO-d$_6$): δ=2.44 (s, 3 H), 5.33 (s, 2 H), 7.10-7.16 (m, 1 H), 7.18-7.28 (m, 3 H), 7.54-7.64 (m, 1 H), 8.22 (d, 1 H).

Example 26A

8-[(2,6-Difluorobenzyl)oxy]-2-methylimidazo[1,2-a]pyridine-3-carboximidamide

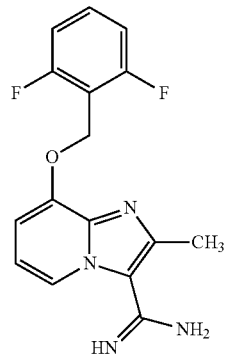 [SMILES: Cc1nc2c(OCc3c(F)cccc3F)cccn2c1C(=N)N]

Under argon, 135 mg (2.5 mmol, 2.52 equivalents) of ammonium chloride were initially charged in 3.9 ml of toluene, and the mixture was cooled to 0° C. At this temperature, 1.26 ml of 2 M trimethylaluminium in toluene (2.5 mmol, 2.52 equivalents) were added, and the solution was stirred at RT for 2 h. In another flask, 300 mg of 8-[(2,6-difluorobenzyl)oxy]-2-methylimidazo[1,2-a]pyridine-3-carbonitrile (Example 25A, 1.0 mmol, 1 equivalent) were initially charged in 3.3 ml of toluene, 2 ml of the solution prepared beforehand were added at RT and the mixture was stirred at 110° C. for 1 h. This procedure was repeated four times. The mixture was then cooled, silica gel and a 1:1 mixture of dichloromethane/methanol were added at RT and the mixture was stirred at RT for 30 min. The silica gel was filtered off over a frit. The silica gel was washed with methanol and the filtrate was concentrated under reduced pressure. The residue was purified by silica gel chromatography (mobile phase: dichloromethane; dichloromethane:methanol=10:2). This gave 137.5 mg (43% of theory) of the title compound.

LC-MS (Method 1): $R_t$=0.51 min

MS (ESpos): m/z=317.1 (M+H)$^+$ $^1$H-NMR (400 Mhz, DMSO-d$_6$): δ=2.46 (s, 3 H), 5.32 (s, 2 H), 7.04 (t, 1 H), 7.14 (d, 1 H), 7.24 (t, 2 H), 7.53-7.66 (m, 1 H), 8.17 (d, 1 H), 9.31 (d, 3 H).

Example 27A

8-[(2,6-Difluorobenzyl)oxy]-N-hydroxy-2-methylimidazo[1,2-a]pyridine-3-carboximidamide

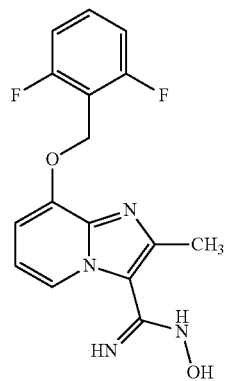 [SMILES: Cc1nc2c(OCc3c(F)cccc3F)cccn2c1C(=N)NO]

50.0 g (148.9 mmol) of 8-[(2,6-difluorobenzyl)oxy]-2-methylimidazo[1,2-a]pyridine-3-carbonitrile from Example 25A were suspended in ethanol (1.5 l), 51.75 g (744.6 mmol) of hydroxylamine hydrochloride and 103.0 ml (744.6 mmol) of triethylamine were added and the mixture was stirred at RT overnight. The mixture was then concentrated under reduced pressure, water (2.0 l) and ethanol (100 ml) were added and the mixture was stirred for 1 h. The solid formed was filtered off, washed with water and dried under high vacuum overnight. This gave 38.5 g (78% of theory) of the title compound.

LC-MS (Method 1): $R_t$=0.56 min

MS (ESpos): m/z=333.2 (M+H)$^+$

Example 28A

8-[(2,6-Difluorobenzyl)oxy]-2-methylimidazo[1,2-a]pyridine-3-carboximidamide hydrochloride

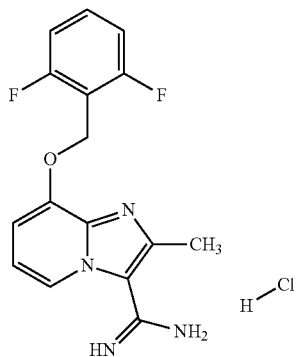 [SMILES: Cc1nc2c(OCc3c(F)cccc3F)cccn2c1C(=N)N ; Cl]

37.5 g (98.4 mmol, purity 87%) of 8-[(2,6-difluorobenzyl)oxy]-N-hydroxy-2-methylimidazo[1,2-a]pyridine-3-carboximidamide from Example 27A were initially charged in acetic acid (1.0 μl), and 11.14 ml (118.08 mmol) of acetic anhydride were added. 7.5 g of palladium/carbon (10%, moist) were then added, and the mixture was hydrogenated at atmospheric pressure for 16 h. The mixture was filtered through kieselguhr and washed with ethanol. After concentration, three times in each case 500 ml of toluene were added to the residue, and the mixture was concentrated under reduced pressure. The residue was stirred with 200 ml of ethyl acetate, filtered and dried under high vacuum. 22.0 g (59% of theory) of the title compound were obtained.

LC-MS (Method 1): $R_t$=0.51 min

MS (ESpos): m/z=317.2 (M+H)$^+$ $^1$H-NMR (400 Mhz, DMSO-d$_6$): δ=1.82 (s, 3H), 2.46 (s, 3 H), 5.31 (s, 2 H), 6.93 (t, 1 H), 7.01 (d, 1 H), 7.21-7.25 (m, 2 H), 7.55-7.63 (m, 1 H), 8.55 (br d, 1 H).

Example 29A

8-[(2,6-Difluorobenzyl)oxy]-2,6-dimethylimidazo[1,2-a]pyridine-3-carboxamide

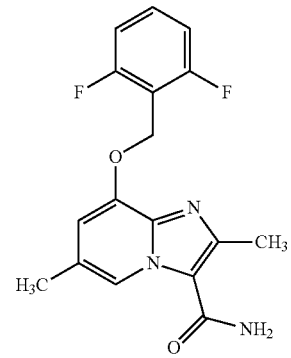

7.0 g (21.07 mmol) of 8-[(2,6-difluorobenzyl)oxy]-2,6-dimethylimidazo[1,2-a]pyridine-3-carboxylic acid from Example 11A were initially charged in 403 ml of dichloromethane, 6.06 g (31.60 mmol) of 1-(3-dimethylaminopropyl)-3-ethylcarbodiimide hydrochloride and 4.27 g (31.60 mmol) of 1-hydroxy-1H-benzotriazole hydrate were added and the mixture was stirred at room temperature for 10 min. Subsequently, 5.63 g (105.32 mmol) of ammonium chloride and 25.68 ml (147.5 mmol) of N,N-diisopropylethylamine were added and the mixture was stirred at room temperature overnight. Water was added to the reaction mixture, and the solid present was filtered off, then stirred with water at 50° C. for 30 min, filtered off again and washed with water. 4.59 g (65% of theory) of the title compound were obtained. The combined filtrate fractions (dichloromethane/water) were separated into the phases. The dichloromethane phase was washed in each case once with saturated aqueous sodium bicarbonate solution and saturated aqueous sodium chloride solution. The organic phase was dried over sodium sulfate, filtered and concentrated under reduced pressure. The residue was stirred with a little acetonitrile and filtered off. This gave a further 1.29 g (17% of theory; purity 93%) of the title compound.

LC-MS (Method 1): $R_t$=0.64 min
MS (ESpos): m/z=332 (M+H)$^+$
$^1$H-NMR (400 Mhz, DMSO-d$_6$): δ=2.31 (s, 3H), 2.50 (s, 3 H; hidden under DMSO signal), 5.28 (s, 2 H), 6.92 (s, 1 H), 7.22 (t, 2 H), 7.35 (br. s, 2 H), 7.53-7.63 (m, 1 H); 8.62 (s, 1 H).

Example 30A

8-[(2,6-Difluorobenzyl)oxy]-2,6-dimethylimidazo[1,2-a]pyridine-3-carbonitrile

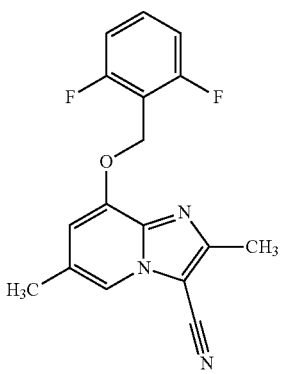

5.7 g (17.20 mmol) of 8-[(2,6-difluorobenzyl)oxy]-2,6-dimethylimidazo[1,2-a]pyridine-3-carboxamide Example 29A were initially charged in 77 ml of THF, and 3.56 ml (44.0 mmol) of pyridine were added. At RT, 6.22 ml (44.0 mmol) of trifluoroacetic anhydride were then added dropwise, and the reaction mixture was stirred at RT for 3 h. After the reaction had ended, the mixture was added to water and extracted three times with ethyl acetate. The combined organic phases were washed once with saturated aqueous sodium bicarbonate solution, once with 1 N aqueous hydrochloric acid and once with saturated sodium chloride solution, dried over sodium sulfate and concentrated under reduced pressure. The residue was dried under reduced pressure overnight. 5.47 g (90% of theory) of the title compound were obtained.

LC-MS (Method 1): $R_t$=1.12 min
MS (ESpos): m/z=314 (M+H)$^+$ $^1$H-NMR (400 Mhz, DMSO-d$_6$): δ=2.37 (s, 3 H), 2.41 (s, 3 H), 5.31 (s, 2 H), 7.12 (s, 1 H), 7.23 (t, 2 H), 7.54-7.63 (m, 1 H), 8.09 (s, 1 H).

Example 31A

8-[(2,6-Difluorobenzyl)oxy]-2,6-dimethylimidazo[1,2-a]pyridine-3-carboximidamide

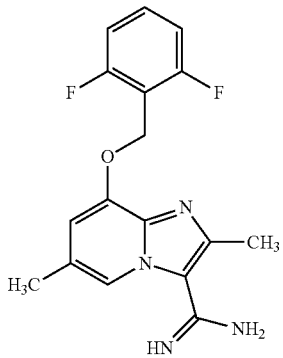

5.47 g (17.46 mmol) of 8-[(2,6-difluorobenzyl)oxy]-2,6-dimethylimidazo[1,2-a]pyridine-3-carbonitrile from Example 30A were reacted analogously to Example 26A. This gave 1.28 g (22% of theory) of the title compound.

LC-MS (Method 1): $R_t$=0.60 min
MS (ESpos): m/z=331.3 (M+H)$^+$
$^1$H-NMR (400 Mhz, DMSO-d$_6$): δ=2.35 (s, 3 H), 2.43 (s, 3 H), 5.31 (s, 2 H), 7.06 (s, 1 H), 7.24 (t, 2 H), 7.54-7.65 (m, 1 H), 8.02 (s, 1 H), 9.25 (br. s, 3 H).

Example 32A

2-Methyl-2-nitropropyl trifluoromethanesulfonate

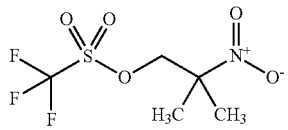

1.0 g (8.40 mmol) of 2-methyl-2-nitropropan-1-ol was initially charged in 20 ml of dichloromethane, 1.0 ml (12.59 mmol) of pyridine was added, the mixture was cooled to 0° C. and 1.85 ml (10.91 mmol) of trifluoromethanesulfonic anhydride was added slowly. The mixture was then stirred at 0° C. for 1 h. The course of the reaction was monitored by TLC (cyclohexane/ethyl acetate 7/3, staining reagent: potassium permanganate stain). The reaction solution was washed in each case once with water and saturated aqueous sodium chloride solution. The organic phase was dried over sodium sulfate and filtered and the filtrate was concentrated. This gave 2.18 g of the target compound (99% of theory). The target compound was stored at −18° C. and used without further purification.

MS (Method 13):
MS (ESpos): m/z=269 (M+NH$_4$)
$^1$H NMR (400 Mhz, DMSO-d$_6$) δ=1.64 (s, 6 H), 5.13 (s, 2 H).

Example 33A

8-[(2,6-Difluorobenzyl)oxy]-3-(2,5-difluoropyridin-4-yl)-2,6-dimethylimidazo[1,2-a]pyridine

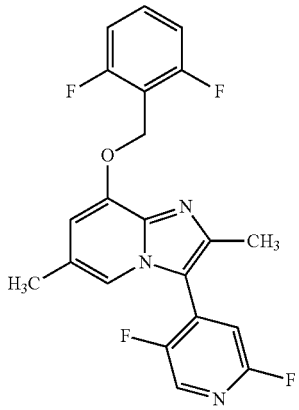 [SMILES: Cc1cc(OCc2c(F)cccc2F)c2nc(C)c(-c3cc(F)ncc3F)n2c1]

Under argon, 541 mg (3.40 mmol) of (2,5-difluoropyridin-4-yl)boric acid, 867 mg (4.09 mmol) of potassium phosphate and 70 mg (0.14 mmol) of bis(tri-tert-butylphosphine)palladium(0) were added in succession to 500 mg (1.36 mmol) of 3-bromo-8-[(2,6-difluorobenzyl)oxy]-2,6-dimethylimidazo[1,2-a]pyridine (Example 21A) in a mixture of 9.6 ml of ethanol, 4.8 ml of water and 4.8 ml of toluene. The suspension was degassed with argon and then stirred at 120° C. for 30 min. After the reaction had ended, the reaction mixture was concentrated and the residue was taken up in ethyl acetate/water and extracted. The aqueous phase was extracted twice with ethyl acetate. The combined organic phases were dried over sodium sulfate, filtered, concentrated on a rotary evaporator and dried under high vacuum. The residue was purified by silica gel chromatography (mobile phase gradient: dichloromethane to dichloromethane/ethyl acetate/methanol=50/3/1). This gave 382 mg of the target compound (68% of theory).

LC-MS (Method 1): $R_t$=0.86 min
MS (ESpos): m/z=402 (M+H)$^+$

Example 34A

6-{8-[(2,6-Difluorobenzyl)oxy]-2-methylimidazo[1,2-a]pyridin-3-yl}-1,3,5-triazine-2,4(1H,3H)-dione

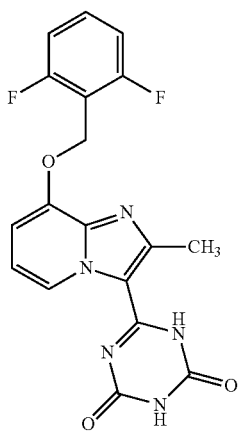

800 mg (2.27 mmol) of 8-[(2,6-difluorobenzyl)oxy]-2-methylimidazo[1,2-a]pyridine-3-carboximidamide hydrochloride from Example 28A were initially charged in 16 ml of dichloromethane, and 0.63 ml (4.25 mmol) of 1,8-diazabicyclo[5.4.0]undec-7-ene (DBU) and 1.09 g (4.25 mmol) of diphenylimido dicarbonate were added. The mixture was stirred at RT overnight. The reaction solution was then diluted with dichloromethane and extracted twice with water. The combined aqueous phases were extracted twice with dichloromethane. The combined organic phases were dried over sodium sulfate, filtered and concentrated on a rotary evaporator. The residue was purified by silica gel chromatography (mobile phase gradient: dichloromethane/methanol=60/1 to dichloromethane/methanol=20/1 to dichloromethane/methanol=10/1). This gave 418 mg of the target compound (39% of theory, purity 81%).

LC-MS (Method 1): $R_t$=0.65 min
MS (ESpos): m/z=386 (M+H)$^+$

Example 35A 3-(4,6-Dichloro-1,3,5-triazin-2-yl)-8-[(2,6-difluorobenzyl)oxy]-2-methylimidazo[1,2-a]pyridine

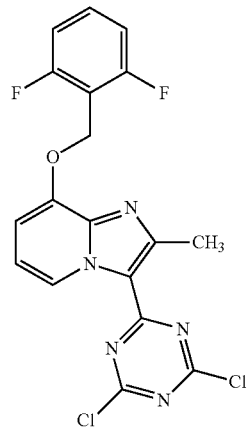 [SMILES: Cc1nc2c(OCc3c(F)cccc3F)cccn2c1-c1nc(Cl)nc(Cl)n1]

418 mg (0.88 mmol, purity 81%) of 6-{8-[(2,6-difluorobenzyl)oxy]-2-methylimidazo[1,2-a]pyridin-3-yl}-1,3,5-triazine-2,4(1H,3H)-dione from Example 34A were suspended in 3.6 ml (38.24 mmol) of phosphoryl chloride, and the mixture was then stirred at 120° C. overnight. For work-up, about 50 ml of water were heated to 60° C. Carefully, with vigorous stirring, the warm reaction solution was added dropwise, and the mixture was stirred for 1 h. This suspension was then cooled to RT and extracted twice with dichloromethane. The combined organic phases were dried over sodium sulfate, filtered and concentrated. The residue was taken up in dichloromethane and a little methanol and purified by silica gel chromatography (mobile phase gradient: cyclohexane/ethyl acetate=10/1 to cyclohexane/ethyl acetate=5/1 to cyclohexane/ethyl acetate=2/1). This gave 120 mg of the target compound (30% of theory).

LC-MS (Method 1): $R_t$=1.30 min
MS (ESpos): m/z=422 (M+H)$^+$

Example 36A ent-Benzyl-{1-[(4-chloro-6-{8-[(2,6-difluorobenzyl)oxy]-2-methylimidazo[1,2-a]pyridin-3-yl}-1,3,5-triazin-2-yl)amino]-5,5,5-trifluoro-2-methylpentan-2-yl}carbamate trifluoroacetate (enantiomer B)

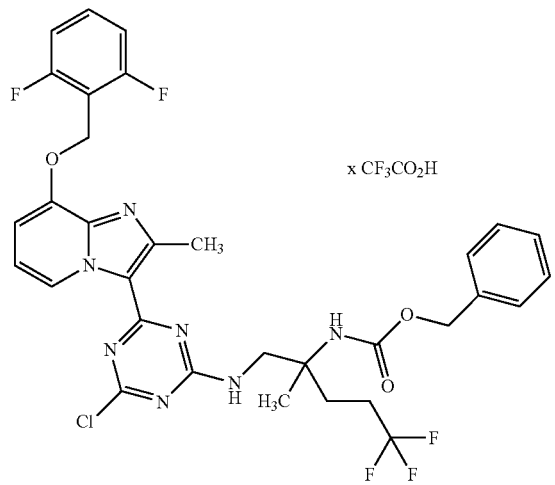 [SMILES: Cc1nc2c(OCc3c(F)cccc3F)cccn2c1-c1nc(Cl)nc(NCC(C)(CCC(F)(F)F)NC(=O)OCc2ccccc2)n1]

x CF₃CO₂H 40 mg (0.09 mmol) of 3-(4,6-dichloro-1,3,5-triazin-2-yl)-8-[(2,6-difluorobenzyl)oxy]-2-methylimidazo[1,2-a]pyridine from Example 35A were initially charged in 0.35 ml of NMP. At RT, 28 mg (0.09 mmol) of ent-benzyl (1-amino-5,5,5-trifluoro-2-methylpentan-2-yl)carbamate (enantiomer B; Example 409A in WO 2014/068099) were added and the mixture was stirred at room temperature for 4 h. Subsequently, 50 µl of NMP and 14 mg (0.045 mmol) of ent-benzyl (1-amino-5,5,5-trifluoro-2-methylpentan-2-yl)carbamate (enantiomer B) were added and stirring at room temperature was continued for 3.5 h. The reaction solution was diluted with acetonitrile, water/TFA was added and the mixture was purified by preparative HPLC (RP18 column, mobile phase: acetonitrile/water gradient with addition of 0.1% TFA). The product fractions were combined and concentrated on a rotary evaporator. The residue was dissolved in dichloromethane and a little methanol and washed twice with saturated aqueous sodium bicarbonate solution. The combined aqueous phases were reextracted twice with dichloromethane. The combined organic phases were dried over sodium sulfate, filtered and concentrated by rotary evaporation. This gave 54 mg of the target compound (71% of theory).

LC-MS (Method 1): $R_t$=1.30 min
MS (ESpos): m/z=690.5 (M+H)⁺

Example 37A

3-Bromo-8-(cyclohexylmethoxy)-2-methylimidazo[1,2-a]pyridine

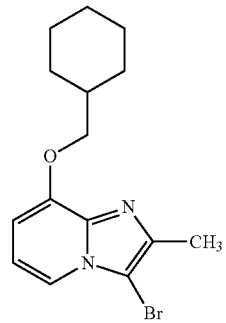 [SMILES: Cc1nc2c(OCC3CCCCC3)cccn2c1Br]

524 mg (6.24 mmol) of sodium bicarbonate were added to a solution of 600 mg (2.08 mmol) of 8-(cyclohexylmethoxy)-2-methylimidazo[1,2-a]pyridine-3-carboxylic acid from Example 6A in 8.3 ml of DMF. At RT, a solution of 389 mg (2.19 mmol) of N-bromosuccinimide in 5.53 ml of DMF was, very slowly [2.6 ml/h], added dropwise using a syringe pump. The reaction solution was diluted with dichloromethane and then washed twice with water. The combined aqueous phases were reextracted twice with dichloromethane. The combined organic phases were dried over sodium sulfate, filtered and concentrated by rotary evaporation. The residue was stirred with water, and the solid obtained was filtered off and dried under high vacuum. 515 mg of the title compound were isolated (71% of theory; 93% purity).

LC-MS (Method 1): $R_t$=0.92 min
MS (ESpos): m/z=323 (M+H)⁺

Example 38A

5-Chloro-2-nitropyridin-3-ol

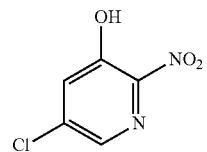 [SMILES: O=[N+]([O-])c1ncc(Cl)cc1O]

With ice cooling, 30 g of 5-chloropyridin-3-ol (232 mmol, 1 equivalent) were dissolved in 228 ml of concentrated sulfuric acid, and 24 ml of concentrated nitric acid were added slowly at 0° C. The reaction was warmed to RT and stirred overnight. The mixture was stirred into an ice/water mixture and stirred for 30 min. The solid was filtered off, washed with cold water and air-dried. This gave 33 g (82% of theory) of the title compound which was used without further purification for the next reaction.

LC-MS (Method 1): $R_t$=0.60 min
MS (ESneg): m/z=172.9/174.9 (M−H)⁻
¹H-NMR (400 Mhz, DMSO-d₆): δ=7.71 (d, 1 H); 8.10 (d, 1 H); 12.14 (br. 1 H).

Example 39A

5-Chloro-3-[(3-fluoropyridin-2-yl)methoxy]-2-nitropyridine

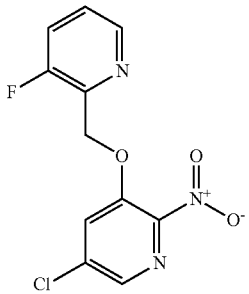 [SMILES: O=[N+]([O-])c1ncc(Cl)cc1OCc1ncccc1F]

20.0 g (114.6 mmol) of 5-chloro-2-nitropyridin-3-ol from Example 38A and 56.0 g (171.9 mmol) of caesium carbonate were initially charged in 319 ml of DMF. 17.51 g (120.3 mmol) of 2-(chloromethyl)-3-fluoropyridine (commercially available; additionally described in: K. Weidmann et al. Journal of Medicinal Chemistry 1992, 35, 438-450; U.S. Pat. No. 5,593,993, 1997; WO2007/2181 A2, 2007) were added and the reaction mixture was stirred at RT overnight. 6.0 g (41.2 mmol) of 2-(chloromethyl)-3-fluoropyridine were added and the mixture was stirred at RT for 24 h. Subsequently, another 6.0 g (41.2 mmol) of 2-(chloromethyl)-3-fluoropyridine and 5.0 g (15.3 mmol) of caesium carbonate were added and the mixture was stirred at 60° C. for 12 h. The reaction mixture was added carefully to 2.3 l of 0.5 M of aqueous hydrochloric acid. The mixture was extracted three times with in each case 500 ml of ethyl acetate. The combined organic phases were washed with 500 ml of saturated aqueous sodium chloride solution, dried and concentrated under reduced pressure. The crude product was purified by means of silica gel chromatography (mobile phase: cyclohexane/ethyl acetate gradient: 9/1 to 7/3). This gave 29.8 g (92% of theory) of the target compound.

LC-MS (Method 1): $R_t$=0.94 min.
MS (ESIpos): m/z=284 (M+H)$^+$.
$^1$H-NMR (400 Mhz, DMSO-d$_6$): δ=5.59 (d, 2H), 7.53-7.60 (m, 1H), 7.80-7.87 (m, 1H), 8.26 (d, 1H), 8.40-8.47 (m, 2H).

Example 40A

5-Chloro-3-[(3-fluoropyridin-2-yl)methoxy]pyridine-2-amine

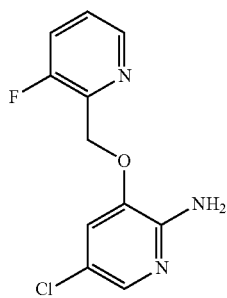 [SMILES: Nc1ncc(Cl)cc1OCc1ncccc1F]

Under argon, 29.8 g (105.1 mmol) of 5-chloro-3-[(3-fluoropyridin-2-yl)methoxy]-2-nitropyridine from Example 39A were initially charged in 317 ml of ethanol. 18.2 g (325.7 mmol) of iron powder were added, and the reaction mixture was heated to reflux. 80.4 ml of conc. aqueous hydrochloric acid were slowly added dropwise and the mixture was heated under reflux for a further 6 h. The reaction mixture was made alkaline with 33% strength ammonia solution and then concentrated under reduced pressure. Purification by silica gel chromatography (mobile phase: dichloromethane/methanol gradient 95/5 to 90/10) gave 25.0 g (94% of theory) of the target compound.

LC-MS (Method 1): $R_t$=0.70 min
MS (ESIpos): m/z=254 (M+H)$^+$
$^1$H-NMR (400 Mhz, DMSO-d$_6$): δ=5.27 (d, 2H), 5.87 (br. s, 2H), 7.32-7.35 (m, 1H), 7.51-7.58 (m, 2H), 7.77-7.85 (m, 1H), 7.45-7.50 (m, 1H).

Example 41A

Ethyl 6-chloro-8-[(3-fluoropyridin-2-yl)methoxy]-2-methylimidazo[1,2-a]pyridine-3-carboxylate

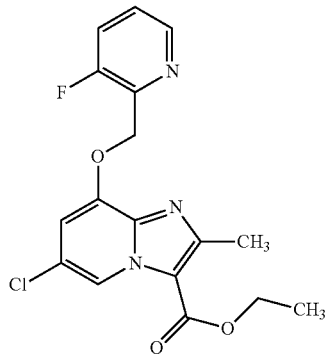 [SMILES: CCOC(=O)c1c(C)nc2c(OCc3ncccc3F)cc(Cl)cn12]

3.00 g (11.83 mmol) of 5-chloro-3-[(3-fluoropyridin-2-yl)methoxy]pyridine-2-amine from Example 40A and 9.73 g (59.13 mmol) of ethyl 2-chloro-3-oxobutanoate were dissolved in 72 ml of ethanol and, together with 4.5 g of 3 Å molecular sieve, stirred under reflux for 6 days. The mixture was cooled and filtered and the filtrate was concentrated under reduced pressure. The residue obtained was purified by silica gel chromatography (mobile phase: cyclohexane/ethyl acetate gradient 4/1 to 2/1). This gave 2.0 g (46% of theory) of the target compound.

LC-MS (Method 1): $R_t$=1.07 min
MS (ESIpos): m/z=364 (M+H)$^+$
$^1$H-NMR (400 Mhz, DMSO-d$_6$): δ=1.36 (t, 3H), 2.56 (s, 3H; superposed by solvent peak), 4.37 (q, 2H), 5.48 (d, 2H), 7.36 (d, 1H), 7.57-7.63 (m, 1H), 7.83-7.90 (m, 1H), 8.50 (d, 1H), 8.92 (d, 1H).

Example 42A

6-Chloro-8-[(3-fluoropyridin-2-yl)methoxy]-2-methylimidazo[1,2-a]pyridine-3-carboxylic acid

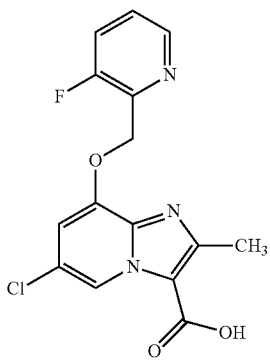 [SMILES: Cc1nc2c(OCc3ncccc3F)cc(Cl)cn2c1C(=O)O]

28.1 ml (28.1 mmol) of 1 M aqueous lithium hydroxide solution were added to 2.0 g (5.62 mmol) of ethyl 6-chloro-8-[(3-fluoropyridin-2-yl)methoxy]-2-methylimidazo[1,2-a]pyridine-3-carboxylate from Example 41A in 110 ml of THF/methanol (5/1), and the mixture was stirred at 40° C. for 2.5 h. Using 6 N aqueous hydrochloric acid, the reaction mixture, which had been cooled to RT, was adjusted to about pH 4, the solvent was concentrated to half its original volume and the precipitated solid was filtered off with suction and dried under reduced pressure. This gave 1.97 g (102% of theory) of the target compound (some of it possibly as hydrochloride salt).

LC-MS (Method 1): $R_t$=0.65 min

MS (ESIpos): m/z=336 (M+H)$^+$ $^1$H-NMR (400 Mhz, DMSO-d$_6$): δ=5.43-5.51 (m, 2H), 7.32 (d, 1H), 7.57-7.63 (m, 1H), 7.83-7.91 (m, 1H), 8.48-8.54 (m, 1H), 8.96-9.00 (m, 1H), 13.36 (br. s, 1H), [further signal under solvent peak].

Example 43A

3-Bromo-6-chloro-8-[(3-fluoropyridin-2-yl)methoxy]-2-methylimidazo[1,2-a]pyridine

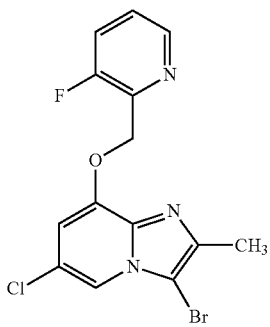 [SMILES: Cc1nc2c(OCc3ncccc3F)cc(Cl)cn2c1Br]

150 mg (1.79 mmol) of sodium bicarbonate were added to a solution of 200 mg (0.60 mmol) of 6-chloro-8-[(3-fluoropyridin-2-yl)methoxy]-2-methylimidazo[1,2-a]pyridine-3-carboxylic acid from Example 42A in 2.4 ml of DMF. At RT, a solution of 111 mg (0.63 mmol) of N-bromosuccinimide in 1.6 ml of DMF was, very slowly [2.6 ml/h], added dropwise using a syringe pump. The reaction solution was diluted with dichloromethane and then washed twice with water. The combined aqueous phases were extracted twice with dichloromethane. The combined organic phases were dried over sodium sulfate, filtered and concentrated by rotary evaporation. The residue was stirred with water, and the solid obtained was filtered off and dried under high vacuum. 156 mg of the title compound were isolated (71% of theory).

LC-MS (Method 1): $R_t$=0.95 min

MS (ESpos): m/z=370 (M+H)$^+$

WORKING EXAMPLES

Example 1

N-Benzyl-5-{8-[(2,6-difluorobenzyl)oxy]-2-methylimidazo[1,2-a]pyridin-3-yl}pyridine-2-amine

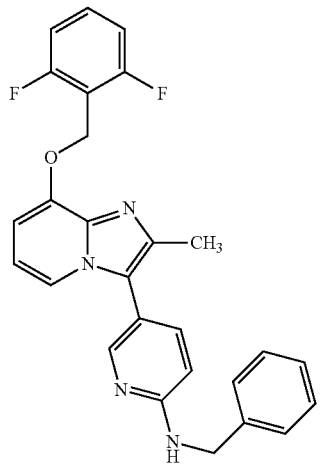 [SMILES: Cc1nc2c(OCc3c(F)cccc3F)cccn2c1-c1ccc(NCc2ccccc2)nc1]

35 mg (0.10 mmol) of 3-bromo-8-[(2,6-difluorobenzyl)oxy]-2-methylimidazo[1,2-a]pyridine (Example 19A), 5.8 mg (0.005 mmol) of tetrakis(triphenylphosphine)palladium (0), 22 mg (0.20 mmol) of sodium carbonate and 0.2 ml of water were added to 31 mg (0.10 mmol) of N-benzyl-5-(4,4,5,5-tetramethyl-1,3,2-dioxaborolan-2-yl)pyridine-2-amine in 0.6 ml of 1,4-dioxane, and the mixture was shaken at 85° C. overnight. After the reaction had ended, the reaction solution was filtered, the 1,4-dioxane was removed under reduced pressure and the residue was dissolved in a little DMSO and purified by preparative HPLC (Method 11). This gave 0.7 mg (2% of theory) of the title compound.

LC-MS (Method 12): $R_t$=0.89 min

MS (ESpos): m/z=457.3 (M+H)$^+$

Analogously to Example 1, the example compounds shown in Table 1 were prepared by reacting 3-bromo-8-[(2,6-difluorobenzyl)oxy]-2-methylimidazo[1,2-a]pyridine (Example 19A) with the appropriate boronic acids or boronic ester [4,4,5,5-tetramethyl-1,3,2-dioxaborolanyl=boronic acid pinacol ester].

TABLE 1

| Example No. | IUPAC name<br>Structure<br>(Yield) | Analytical data |
|---|---|---|
| 2 | 5-{8-[(2,6-difluorobenzyl)oxy]-2-methylimidazo[1,2-a]pyridin-3-yl}-N-(2-methoxyethyl)pyridine-2-amine<br>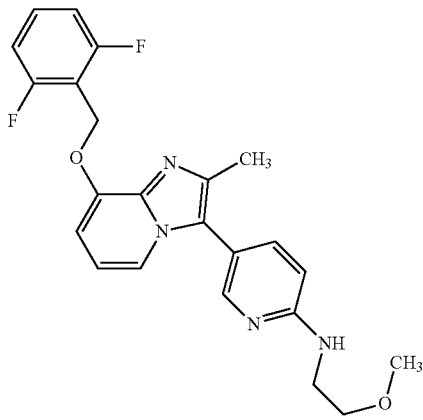<br>The boronic acid pinacol ester [1] was used.<br>(4% of theory, purity 100%) | LC-MS (Method 12): $R_t$ = 0.75 min<br>MS (ESpos): m/z = 425 (M + H)$^+$ |
| 3 | 5-{8-[(2,6-difluorobenzyl)oxy]-2-methylimidazo[1,2-a]pyridin-3-yl}-N-ethyl-N-methylpyridine-2-amine<br>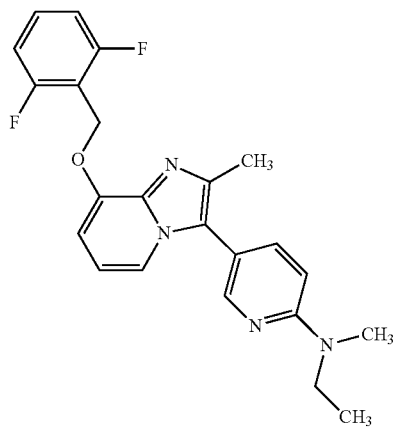<br>The boronic acid [2] was used.<br>(19% of theory, purity 77%) | LC-MS (Method 12): $R_t$ = 0.80 min<br>MS (ESpos): m/z = 409.2 (M + H)$^+$ |

TABLE 1-continued

| Example No. | IUPAC name<br>Structure<br>(Yield) | Analytical data |
|---|---|---|
| 4 | 8-[(2,6-difluorobenzyl)oxy]-3-[6-(2,6-dimethylmorpholin-4-yl)pyridin-3-yl]-2-methylimidazo[1,2-a]pyridine<br>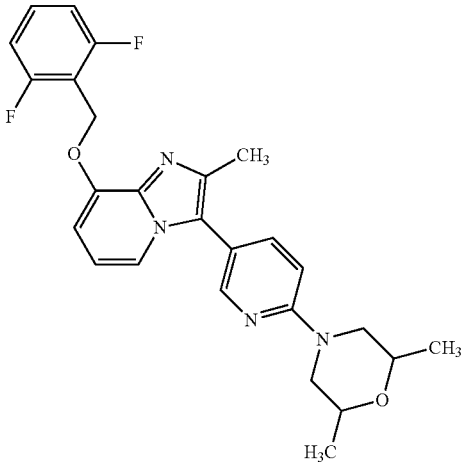<br>The boronic acid pinacol ester [3] was used.<br>(19% of theory, purity 83%) | LC-MS (Method 12): $R_t$ = 0.94 min<br>MS (ESpos): m/z = 465.2 (M + H)⁺ |
| 5 | 5-{8-[(2,6-difluorobenzyl)oxy]-2-methylimidazo[1,2-a]pyridin-3-yl}-N-phenylpyridine-2-amine<br>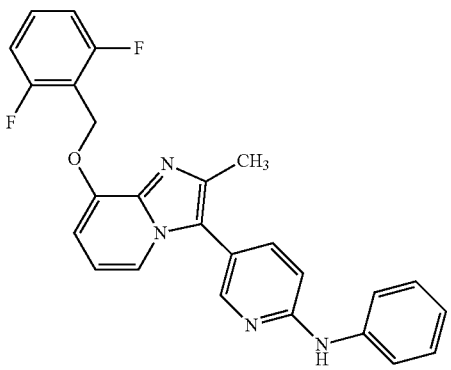<br>The boronic acid pinacol ester [4] was used.<br>(11% of theory, purity 82%) | LC-MS (Method 12): $R_t$ = 0.94 min<br>MS (ESpos): m/z = 443.2 (M + H)⁺ |

[1] Preparation analogous to ASTRAZENECA, patent: WO2007/86800 A1, 2007 from 5-bromo-N-(2-methoxyethyl)pyridine-2-amine.

[2] Preparation analogous to Majo, Vattoly J.; Prabhakaran, Jaya; Mann, J. John; Kumar, J.S. Dileep, *Advanced Synthesis and Catalysis*, 2003, vol. 345, p. 620-624 from 5-bromo-N-ethyl-N-methylpyridine-2-amine.

[3] Preparation analogous to XCOVERY, INC. patent: WO2008/88881 A1, 2008 from 4-(5-bromopyridin-2-yl)-2,6-dimethyl-morpholine.

[4] Preparation analogous to BioMarin IGA, Ltd.; Wren, Stephen Paul; Wynne, Graham Michael; Lecci, Cristina; Wilson, Francis Xavier; Davis, Paul James; patent: WO2010/57833 A1, 2010 from 5-bromo-N-phenylpyridine-2-amine.

Example 6

8-[(2,6-Difluorobenzyl)oxy]-2-methyl-3-[2-(4-methylpiperazin-1-yl)pyrimidin-5-yl]imidazo[1,2-a]pyridine

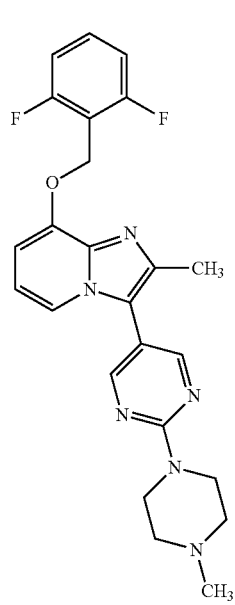 [SMILES: Cc1nc2c(OCc3c(F)cccc3F)cccn2c1-c1cnc(N2CCN(C)CC2)nc1]

125 mg (0.35 mmol) of 3-bromo-8-[(2,6-difluorobenzyl)oxy]-2-methylimidazo[1,2-a]pyridine (Example 19A), 118 mg (0.39 mmol) of 2-(4-methylpiperazin-1-yl)-5-(4,4,5,5-tetramethyl-1,3,2-dioxaborolan-2-yl)pyrimidine and 119 mg (1.42 mmol) of sodium bicarbonate were initially charged with 14 mg (0.02 mmol) of 1,1'-bis(diphenylphosphino)ferrocenepalladium(II) chloride/dichloromethane complex, and a degassed 3:1 mixture of 1,2-dimethoxyethane and water was added. The mixture was stirred overnight at 80° C. The reaction solution was diluted with acetonitrile/water, filtered through a Millipore filter and purified by preparative HPLC (RP18 column, mobile phase: acetonitrile/water gradient with addition of 0.1% TFA). The product fractions were concentrated and the residue was taken up in dichloromethane and washed twice with saturated aqueous sodium bicarbonate solution. The aqueous phase was extracted two more times with dichloromethane. The combined organic phases were dried over sodium sulfate, filtered, concentrated and lyophilized. This gave 77 mg of the target compound (48% of theory).

LC-MS (Method 16): $R_t$=0.46 min

MS (ESpos): m/z=451 (M+H)$^+$

Example 7

6-{8-[(2,6-Difluorobenzyl)oxy]-2,6-dimethylimidazo[1,2-a]pyridin-3-yl}-1,3,5-triazine-2,4-diamine

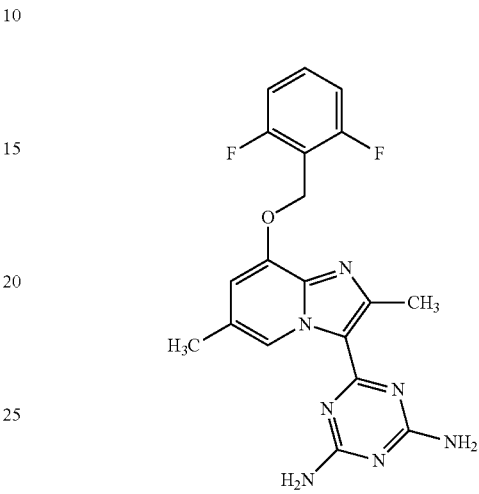

Under argon, 43 mg (0.31 mmol) of imidodicarbonimidediamide hydrochloride [biguanide hydrochloride] were initially charged in 0.93 ml abs. methanol, 148 mg (0.16 ml, 0.69 mmol) of sodium methoxide (25% in methanol) were added and the mixture was stirred at 50° C. for 30 min. Subsequently, 75 mg (0.21 mmol) of ethyl 8-[(2,6-difluorobenzyl)oxy]-2,6-dimethylimidazo[1,2-a]pyridine-3-carboxylate from Example 10A were added and the mixture was stirred under reflux overnight. After cooling, the reaction mixture was poured onto water and the solid formed was filtered off and dried. The crude product was dissolved in acetonitrile/water/TFA and purified by preparative HPLC (RP18 column, mobile phase: acetonitrile/water gradient with addition of 0.1% TFA). The product-containing fractions were concentrated, dissolved in dichloromethane and washed with saturated aqueous sodium bicarbonate solution. The aqueous phase was extracted twice with dichloromethane with addition of a little methanol. The combined organic phases were dried over sodium sulfate and filtered, the filtrate was concentrated and the residue was stirred with water. The precipitate was filtered off and dried under high vacuum. This gave 6.3 mg of the target compound (7.6% of theory).

LC-MS (Method 1): $R_t$=0.73 min

MS (ESpos): m/z=398 (M+H)$^+$ $^1$H-NMR (400 Mhz, DMSO-$d_6$) δ=2.38 (s, 3 H), 2.73 (s, 3 H), 5.29 (s, 2 H), 6.72 (br. s, 4 H), 6.92 (s, 1 H), 7.22 (t, 2 H), 7.54-7.64 (m, 1 H), 9.60 (s, 1 H).

Example 8

6-{8-[(2,6-Difluorobenzyl)oxy]-2,6-dimethylimidazo[1,2-a]pyridin-3-yl}-N,N-dimethyl-1,3,5-triazine-2,4-diamine

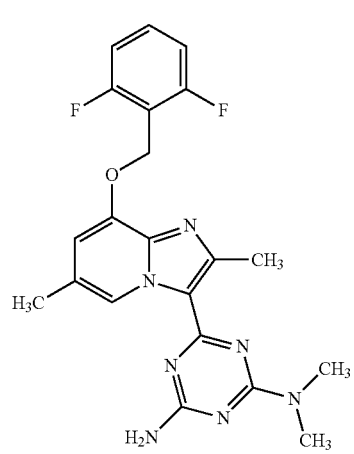

Under argon, 103 mg (0.62 mmol) of N,N-dimethylimidodicarbonimidediamide hydrochloride [methformin hydrochloride] were initially charged in 1.87 ml abs. methanol, 297 mg (0.31 ml, 1.38 mmol) of sodium methoxide (25% in methanol) were added and the mixture was stirred at 50° C. for 30 min. Subsequently, 150 mg (0.42 mmol) of ethyl 8-[(2,6-difluorobenzyl)oxy]-2,6-dimethylimidazo[1,2-a]pyridine-3-carboxylate from Example 10A were added and the mixture was stirred under reflux overnight. After cooling, the reaction mixture was poured onto water and the solid formed was filtered off with suction and dried. The crude product was dissolved in acetonitrile/water/TFA and purified by preparative HPLC (RP18 column, mobile phase: acetonitrile/water gradient with addition of 0.1% TFA). The crude product was purified again by silica gel chromatography (mobile phase: cyclohexane/ethyl acetate: 2/1 then 1/1). This gave 31 mg of the target compound (16% of theory, purity 92%).

LC-MS (Method 1): $R_t$=0.85 min

MS (ESpos): m/z=426 (M+H)$^+$ $^1$H-NMR (400 Mhz, DMSO-d$_6$) δ=2.37 (s, 3 H), 2.72 (s, 3 H), 3.05-3.20 (m, 6 H), 5.29 (s, 2 H), 6.78-7.09 (m, 3 H), 7.22 (t, 2 H), 7.54-7.64 (m, 1 H), 9.62 (s, 1 H).

Example 9

6-{8-[(2,6-Difluorobenzyl)oxy]-2,6-dimethylimidazo[1,2-a]pyridin-3-yl}-N-propyl-1,3,5-triazine-2,4-diamine

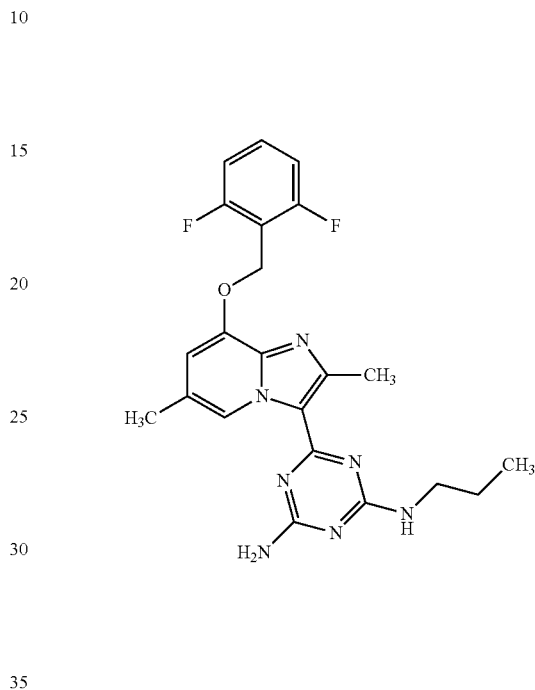

Under argon, 89 mg (0.62 mmol) of 1-amino(propylamino)methylene]guanidine were initially charged in 1.87 ml abs. methanol, 297 mg (0.31 ml, 1.38 mmol) of sodium methoxide (25% in methanol) were added and the mixture was stirred at 50° C. for 30 min. Subsequently, 150 mg (0.42 mmol) of ethyl 8-[(2,6-difluorobenzyl)oxy]-2,6-dimethylimidazo[1,2-a]pyridine-3-carboxylate from Example 10A were added and the mixture was stirred under reflux overnight. After cooling, the reaction mixture was poured onto water and the solid formed was filtered off with suction and dried. The crude product was dissolved in acetonitrile/water/TFA and purified by preparative HPLC (RP18 column, mobile phase: acetonitrile/water gradient with addition of 0.1% TFA). The crude product was purified again by silica gel chromatography (mobile phase: cyclohexane/ethyl acetate: 2/1 then 1/1). This gave 36 mg of the target compound (18% of theory, purity 93%).

LC-MS (Method 1): $R_t$=0.87 min

MS (ESpos): m/z=440 (M+H)$^+$ $^1$H-NMR (400 Mhz, DMSO-d$_6$) δ=0.91 (t, 3 H), 1.49-1.63 (2 H), 2.38 (s, 3 H), 2.72 (s, 3 H), 3.20-3.32 (m, 2 H), 5.30 (s, 2 H), 6.60-6.90 (m, 2 H), 6.91-6.98 (m, 1 H), 7.20-7.32 (m, 2 H), 7.55-7.63 (m, 1 H), 9.58-9.64 (m, 1 H).

Example 10

N'-(4-{8-[(2,6-Difluorobenzyl)oxy]-2,6-dimethyl-imidazo[1,2-a]pyridin-3-yl}-5-fluoropyridin-2-yl)-2-methylpropane-1,2-diamine

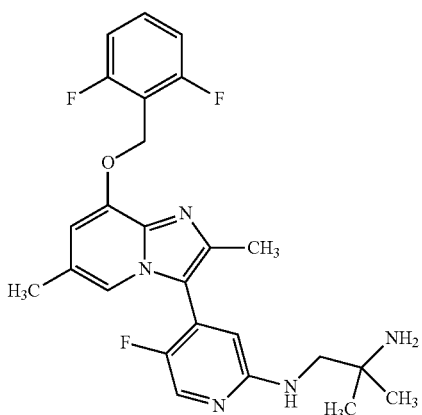

30 mg (0.072 mmol) of 8-[(2,6-difluorobenzyl)oxy]-3-(2,5-difluoropyridin-4-yl)-2,6-dimethylimidazo[1,2-a]pyridine from Example 33A were initially charged in 0.27 ml of NMP. At room temperature, 32 mg (0.36 mmol) of 2-methylpropane-1,2-diamine were added and the mixture was stirred at 150° C. in a closed vessel in an oil bath for 2 h. Another 13 mg (0.15 mmol) of 2-methylpropane-1,2-diamine were added and the mixture was stirred at 150° C. in a closed vessel in the microwave for 3 h. Another 19 mg (0.22 mmol) of 2-methylpropane-1,2-diamine were added and the mixture was stirred at 150° C. in a closed vessel in the microwave for 3 h. 0.27 ml of NMP was added, and the mixture was stirred in the microwave at 180° C. for 5 h. The reaction solution was diluted with acetonitrile/water, TFA was added and the mixture was purified by preparative HPLC (RP18 column, mobile phase: acetonitrile/water gradient with addition of 0.1% TFA). The product fractions were concentrated, dissolved in dichloromethane and washed twice with saturated aqueous sodium bicarbonate solution. The combined aqueous phases were extracted twice with dichloromethane. The combined organic phases were dried over sodium sulfate, filtered and concentrated by rotary evaporation. This gave 9 mg of the target compound (27% of theory).

LC-MS (Method 1): $R_t$=0.64 min
MS (ESpos): m/z=470 (M+H)$^+$
$^1$H-NMR (400 Mhz, DMSO-d$_6$) δ=1.05 (s, 6 H), 1.75 (br. s, 2 H), 2.24-2.29 (m, 6 H), 3.18 (d, 2 H), 5.30 (s, 2 H), 6.53 (t, 1 H), 6.68 (d, 1 H), 6.84 (s, 1 H), 7.19-7.28 (m, 2 H), 7.55-7.65 (m, 2 H), 8.08 (s, 1 H).

Example 11

N'-(4-Chloro-6-{8-[(2,6-difluorobenzyl)oxy]-2-methylimidazo[1,2-a]pyridin-3-yl}-1,3,5-triazin-2-yl)-2-methylpropane-1,2-diamine

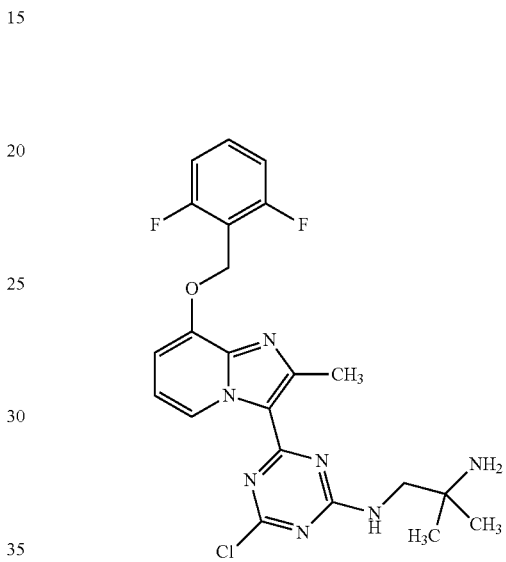

25 mg (0.058 mmol) of 3-(4,6-dichloro-1,3,5-triazin-2-yl)-8-[(2,6-difluorobenzyl)oxy]-2-methylimidazo[1,2-a]pyridine from Example 35A were initially charged in 0.22 ml of NMP. At room temperature, 5.2 mg (0.058 mmol) of 2-methylpropane-1,2-diamine were added and the mixture was stirred at RT in a closed vessel for 1.5 h. The reaction solution was diluted with acetonitrile/water, TFA was added and the mixture was purified by preparative HPLC (RP18 column, mobile phase: acetonitrile/water gradient with addition of 0.1% TFA). The product fractions were concentrated, dissolved in dichloromethane and washed twice with saturated aqueous sodium bicarbonate solution. The combined aqueous phases were extracted twice with dichloromethane. The combined organic phases were dried over sodium sulfate, filtered and concentrated by rotary evaporation. This gave 15 mg of the target compound (55% of theory).

LC-MS (Method 1): $R_t$=0.70 min
MS (ESpos): m/z=474 (M+H)$^+$
$^1$H-NMR (400 Mhz, DMSO-d$_6$) δ=1.07 (s, 6 H), 1.69 (br. s, 2 H), 2.73-2.77 (m, 3 H), 3.23-3.40 (m, 2 H; superposed by solvent peak), 5.33 (s, 2 H), 7.05-7.28 (m, 4 H), 7.55-7.64 (m, 1 H), 8.48 (br. s, 1 H), 9.48 and 9.68 (each d, together 1 H).

Example 12 ent-$N^1$-(4-{8-[(2,6-Difluorobenzyl)oxy]-2-methyl-imidazo[1,2-a]pyridin-3-yl}-1,3,5-triazin-2-yl)-5,5,5-trifluoro-2-methylpentane-1,2-diamine (enantiomer B)

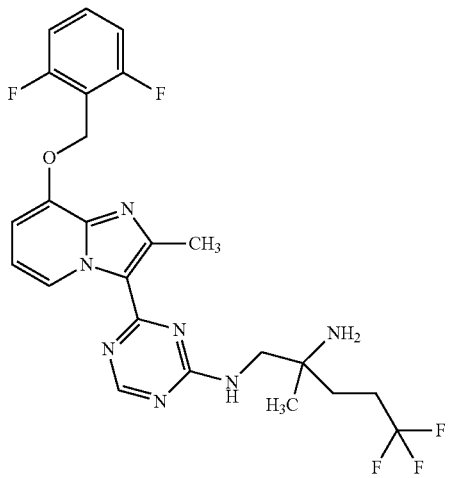 [SMILES: Cc1nc2c(OCc3c(F)cccc3F)cccn2c1-c1ncnc(NCC(C)(N)CCC(F)(F)F)n1]

54 mg (0.07 mmol) of ent-benzyl {1-[(4-chloro-6-{8-[(2,6-difluorobenzyl)oxy]-2-methylimidazo[1,2-a]pyridin-3-yl}-1,3,5-triazin-2-yl)amino]-5,5,5-trifluoro-2-methylpentan-2-yl}carbamate trifluoroacetate (enantiomer B) from Example 36A were dissolved in 1.7 ml of ethanol, and 5 µl (0.07 mmol) of trifluoroacetic acid were added. Under argon, 2 mg of palladium/activated carbon (10%) were added. The reaction mixture was hydrogenated at RT under standard pressure for 4.5 h. The reaction mixture was filtered through a Millipore filter, washed well with ethanol and concentrated using a rotary evaporator. The residue was dissolved again in 1.7 ml of ethanol, 5 µl (0.07 mmol) of trifluoroacetic acid and 2 mg of palladium/activated carbon (10%) were added under argon and the mixture was hydrogenated at standard pressure for 1.5 min. The reaction mixture was filtered through a Millipore filter, washed well with ethanol and concentrated using a rotary evaporator. The residue was taken up in acetonitrile, water/TFA was added and the mixture was purified by preparative HPLC (RP18 column, mobile phase: acetonitrile/water gradient with addition of 0.1% TFA). The product fractions were combined and concentrated on a rotary evaporator. The residue was dissolved in dichloromethane and washed twice with saturated aqueous sodium bicarbonate solution. The combined aqueous phases were extracted twice with dichloromethane. The combined organic phases were dried over sodium sulfate, filtered and concentrated. This gave 19 mg of the target compound (54% of theory).

LC-MS (Method 1): $R_t$=0.68 min
MS (ESpos): m/z=522 (M+H)$^+$ $^1$H-NMR (400 Mhz, DMSO-$d_6$) δ=1.01 (s, 3 H), 1.48-1.69 (m, 4 H), 2.21-2.48 (m, 2 H), 2.77 (s, 3 H), 3.26-3.42 (m, 2 H; superposed by solvent peak), 5.33 (s, 2 H), 7.00-7.09 (m, 1 H), 7.10-7.16 (m, 1 H), 7.19-7.28 (m, 2 H), 7.55-7.64 (m, 1 H), 7.96-8.08 (m, 1 H), 8.58 (d, 1 H), 9.61 and 9.76 (each d, together 1 H).

Example 13

8-[(2,6-Difluorobenzyl)oxy]-2,6-dimethyl-3-[2-(piperazin-1-yl)pyridin-4-yl]imidazo[1,2-a]pyridine

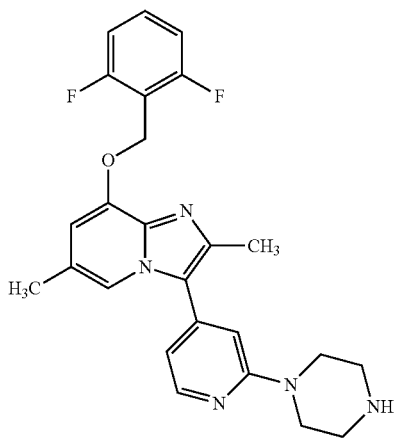 [SMILES: Cc1cc(OCc2c(F)cccc2F)c2nc(C)c(-c3ccnc(N4CCNCC4)c3)n2c1]

Under argon, 71 mg (0.25 mmol) of 1-[4-(4,4,5,5-tetramethyl-1,3,2-dioxaborolan-2-yl)pyridin-2-yl]piperazine, 104 mg (0.49 mmol) of potassium phosphate and 8 mg (0.016 mmol) of bis(tri-tert-butylphosphine)palladium(0) were added in succession to 60 mg (0.16 mmol) of 3-bromo-8-[(2,6-difluorobenzyl)oxy]-2,6-dimethylimidazo[1,2-a]pyridine (Example 21A) in a mixture of 1.2 ml of ethanol, 0.6 ml of water and 0.6 ml of toluene. The suspension was degassed with argon and then stirred at 120° C. for 40 min. After the reaction had ended, the reaction mixture was concentrated and the residue was taken up in ethyl acetate/water and extracted. The aqueous phase was extracted twice with ethyl acetate. The combined organic phases were dried over sodium sulfate, filtered, concentrated on a rotary evaporator and dried under high vacuum. The residue was purified by preparative HPLC (RP18 column, mobile phase: acetonitrile/water gradient with addition of 0.1% TFA). The product fractions were combined and concentrated on a rotary evaporator. The residue was dissolved in dichloromethane and a little methanol and washed twice with saturated aqueous sodium bicarbonate solution. The combined aqueous phases were extracted twice with dichloromethane. The combined organic phases were dried over sodium sulfate, filtered and concentrated. This gave 31 mg of the target compound (41% of theory).

LC-MS (Method 1): $R_t$=0.54 min
MS (ESpos): m/z=450 (M+H)$^+$

Example 14

8-[(2,6-Difluorobenzyl)oxy]-2,6-dimethyl-3-[3-(pyrrolidin-1-yl)phenyl]imidazo[1,2-a]pyridine

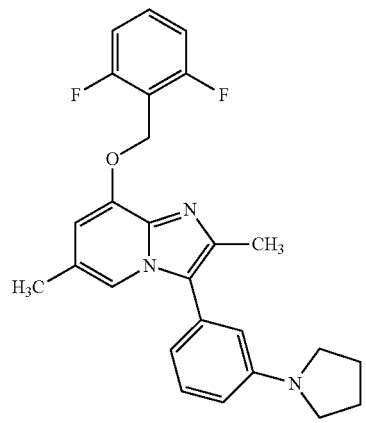 [SMILES: Cc1cc(OCc2c(F)cccc2F)c2nc(C)c(-c3cccc(N4CCCC4)c3)n2c1]

Under argon, 78 mg (0.41 mmol) of [3-(pyrrolidin-1-yl)phenyl]boric acid, 104 mg (0.49 mmol) of potassium phosphate and 8 mg (0.016 mmol) of bis(tri-tert-butylphosphine)palladium(0) were added in succession to 60 mg (0.16 mmol) of 3-bromo-8-[(2,6-difluorobenzyl)oxy]-2,6-dimethylimidazo[1,2-a]pyridine (Example 21A) in a mixture of 1.2 ml of ethanol, 0.6 ml of water and 0.6 ml of toluene. The suspension was degassed with argon and then stirred at 120° C. for 30 min. After the reaction had ended, the reaction mixture was concentrated and the residue was taken up in ethyl acetate/water and extracted. The aqueous phase was extracted twice with ethyl acetate. The combined organic phases were dried over sodium sulfate, filtered, concentrated on a rotary evaporator and dried under high vacuum. The residue was purified by preparative HPLC (RP18 column, mobile phase: acetonitrile/water gradient with addition of 0.1% TFA). The product fractions were combined and concentrated on a rotary evaporator. The residue was dissolved in dichloromethane and washed twice with saturated aqueous sodium bicarbonate solution. The combined aqueous phases were extracted twice with dichloromethane. The combined organic phases were dried over sodium sulfate, filtered and concentrated. This gave 32 mg of the target compound (44% of theory).

LC-MS (Method 1): $R_t$=1.00 min
MS (ESpos): m/z=434 (M+H)$^+$
$^1$H-NMR (500 Mhz, DMSO-d$_6$) δ=1.93-2.02 (m, 4 H), 2.24 (s, 3 H), 2.37 (s, 3 H), 3.23-3.32 (m, 4 H; superposed by solvent peak), 5.29 (s, 2 H), 6.54 (s, 1 H), 6.62 (d, 1 H), 6.66 (d, 1 H), 6.72 (s, 1 H), 7.19-7.28 (m, 2 H), 7.32 (t, 1 H), 7.55-7.63 (m, 1 H), 7.71 (s, 1 H).

Example 15

N-(3-{8-[(2,6-Difluorobenzyl)oxy]-2,6-dimethylimidazo[1,2-a]pyridin-3-yl}phenyl)acetamide

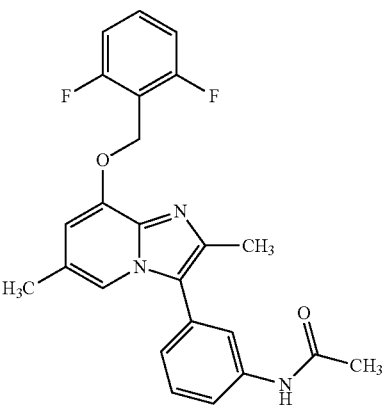 [SMILES: CC(=O)Nc1cccc(-c2c(C)nc3c(OCc4c(F)cccc4F)cc(C)cn23)c1]

Under argon, 44 mg (0.25 mmol) of (3-acetamidophenyl)boric acid, 104 mg (0.49 mmol) of potassium phosphate and 8 mg (0.016 mmol) of bis(tri-tert-butylphosphine)palladium(0) were added in succession to 60 mg (0.16 mmol) of 3-bromo-8-[(2,6-difluorobenzyl)oxy]-2,6-dimethylimidazo[1,2-a]pyridine (Example 21A) in a mixture of 1.2 ml of ethanol, 0.6 ml of water and 0.6 ml of toluene. The suspension was degassed with argon and then stirred at 120° C. for 30 min. After the reaction had ended, the reaction mixture was concentrated and the residue was taken up in ethyl acetate/water and extracted. The aqueous phase was extracted twice with ethyl acetate. The combined organic phases were dried over sodium sulfate, filtered, concentrated on a rotary evaporator and dried under high vacuum. The residue was purified by preparative HPLC (RP18 column, mobile phase: acetonitrile/water gradient with addition of 0.1% TFA). The product fractions were combined and concentrated on a rotary evaporator. The residue was dissolved in dichloromethane and washed twice with saturated aqueous sodium bicarbonate solution. The combined aqueous phases were extracted twice with dichloromethane. The combined organic phases were dried over sodium sulfate, filtered and concentrated. This gave 35 mg of the target compound (48% of theory).

LC-MS (Method 1): $R_t$=0.76 min
MS (ESpos): m/z=422 (M+H)$^+$

Example 16

2,6-Dimethyl-3-[4-(pyrrolidin-1-yl)pyrimidin-2-yl]-8-[(2,3,6-trifluorobenzyl)oxy]imidazo[1,2-a]pyridine trifluoroacetate

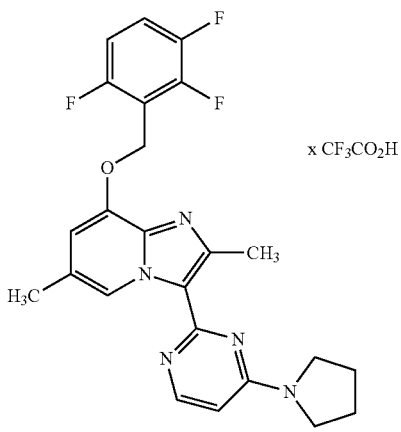 [SMILES: Cc1cc(OCc2c(F)ccc(F)c2F)c2nc(C)c(-c3nccc(N4CCCC4)n3)n2c1]

80 mg (0.26 mmol) of 2,6-dimethyl-8-[(2,3,6-trifluorobenzyl)oxy]imidazo[1,2-a]pyridine (Example 22A), 39 mg (0.21 mmol) of 2-chloro-4-(pyrrolidin-1-yl)pyrimidine and 26 mg (0.26 mmol) of potassium acetate were initially charged in 0.5 ml of NMP. Argon was passed through the reaction mixture for 5 min. 15 mg (0.01 mmol) of tetrakis(triphenylphosphine)palladium(0) were then added, and the mixture was stirred in the microwave at 150° C. for 12 h. The mixture was once more gassed with argon, 15 mg (0.01 mmol) of tetrakis(triphenylphosphine)palladium(0) were added and the mixture was stirred in the microwave at 150° C. for 4.5 h. The reaction mixture was cooled, water/TFA was added and the product was purified by preparative HPLC (RP18 column, mobile phase: acetonitrile/water gradient with addition of 0.1% TFA). This gave 5.5 mg of the target compound (3.4% of theory, purity 92%).

LC-MS (Method 1): $R_t$=0.98 min
MS (ESpos): m/z=454 (M+H)$^+$

Example 17

2-{2,6-Dimethyl-8-[(2,3,6-trifluorobenzyl)oxy]imidazo[1,2-a]pyridin-3-yl}-N,N-dimethylpyrimidine-4-amine

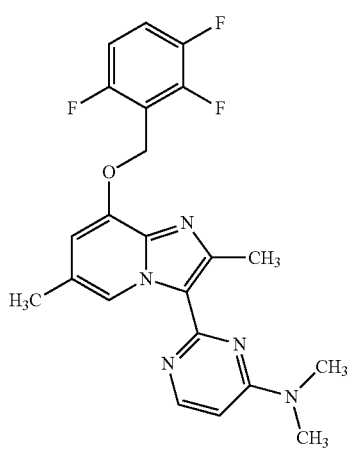

140 mg (0.46 mmol) of 2,6-dimethyl-8-[(2,3,6-trifluorobenzyl)oxy]imidazo[1,2-a]pyridine (Example 22A), 58 mg (0.37 mmol) of 2-chloro-N,N-dimethylpyrimidine-4-amine and 45 mg (0.46 mmol) of potassium acetate were initially charged in 0.7 ml of NMP. Argon was passed through the reaction mixture for 5 min. 26 mg (0.02 mmol) of tetrakis(triphenylphosphine)palladium(0) were then added, and the mixture was stirred in the microwave at 150° C. for 12 h. The reaction mixture was cooled, water/TFA was added and the product was purified by preparative HPLC (RP18 column, mobile phase: acetonitrile/water gradient with addition of 0.1% TFA). The product fractions were concentrated and purified by silica gel chromatography (mobile phase: dichloromethane/methanol gradient). The product fractions were concentrated and re-purified by thick-layer chromatography (mobile phase: dichloromethane/methanol/ethyl acetate=10/1/2). This gave 1 mg of the target compound (0.3% of theory, purity 55%).

LC-MS (Method 1): $R_t$=0.75 min
MS (ESpos): m/z=428 (M+H)$^+$

Example 18

N-Benzyl-2-{2,6-dimethyl-8-[(2,3,6-trifluorobenzyl)oxy]imidazo[1,2-a]pyridin-3-yl}pyrimidine-4-amine

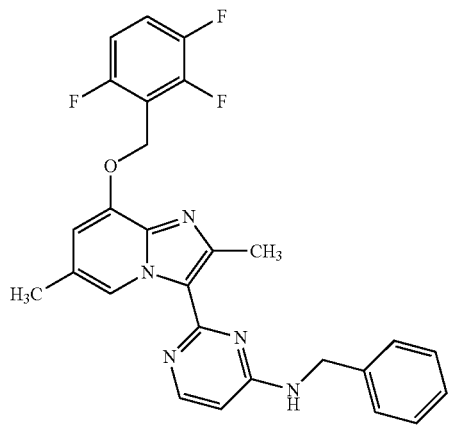 [SMILES: Cc1cc(OCc2c(F)ccc(F)c2F)c2nc(C)c(-c3nccc(NCc4ccccc4)n3)n2c1]

100 mg (0.33 mmol) of 2,6-dimethyl-8-[(2,3,6-trifluorobenzyl)oxy]imidazo[1,2-a]pyridine (Example 22A), 57 mg (0.26 mmol) of N-benzyl-2-chloropyrimidine-4-amine and 32 mg (0.33 mmol) of potassium acetate were initially charged in 0.95 ml of NMP. Argon was passed through the reaction mixture for 5 min. 38 mg (0.03 mmol) of tetrakis(triphenylphosphine)palladium(0) were then added, and the mixture was stirred in the microwave at 150° C. for 8 h. The reaction mixture was cooled, acetonitrile/water/TFA was added and the product was purified by preparative HPLC (RP18 column, mobile phase: acetonitrile/water gradient with addition of 0.1% TFA). The product fractions were concentrated and purified by thick-layer chromatography (mobile phase: dichloromethane/methanol/ethyl acetate=10/1/2). The product fractions were concentrated and re-purified by preparative HPLC (Kinetix, 5μ, C18 column, mobile phase: acetonitrile/water (50/50) with addition of 0.2%

TFA). This gave 1.5 mg of the target compound (0.6% of theory, purity 60%).

LC-MS (Method 1): $R_t$=0.92 min

MS (ESpos): m/z=490 (M+H)$^+$

Example 19

N-{3-[8-(Cyclohexylmethoxy)-2-methylimidazo[1,2-a]pyridin-3-yl]phenyl}acetamide

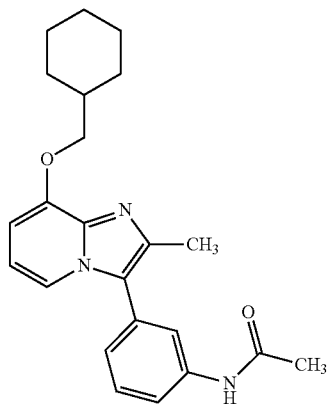 [SMILES: CC(=O)Nc1cccc(-c2c(C)nc3c(OCC4CCCCC4)cccn23)c1]

Under argon, 46 mg (0.26 mmol) of (3-acetamidophenyl)boric acid, 110 mg (0.52 mmol) of potassium phosphate and 9 mg (0.017 mmol) of bis(tri-tert-butylphosphine)palladium (0) were added in succession to 60 mg (0.17 mmol; purity 93%) of 3-bromo-8-(cyclohexylmethoxy)-2-methylimidazo[1,2-a]pyridine (Example 37A) in a mixture of 1.2 ml of ethanol, 0.6 ml of water and 0.6 ml of toluene. The suspension was degassed with argon and then stirred at 120° C. for 30 min. After the reaction had ended, the reaction mixture was concentrated and the residue was taken up in ethyl acetate/water and extracted. The aqueous phase was extracted twice with ethyl acetate. The combined organic phases were dried over sodium sulfate, filtered, concentrated on a rotary evaporator and dried under high vacuum. The residue was purified by preparative HPLC (RP18 column, mobile phase: acetonitrile/water gradient with addition of 0.1% TFA). The product fractions were combined and concentrated on a rotary evaporator. The residue was dissolved in dichloromethane and a little methanol and washed twice with saturated aqueous sodium bicarbonate solution. The combined aqueous phases were extracted twice with dichloromethane. The combined organic phases were dried over sodium sulfate, filtered and concentrated. The product fractions were purified once more by thick-layer chromatography (mobile phase: dichloromethane/methanol=15/1). This gave 34 mg of the target compound (51% of theory).

LC-MS (Method 1): $R_t$=0.78 min

MS (ESpos): m/z=378 (M+H)$^+$

Example 20

N-(3-{6-Chloro-8-[(3-fluoropyridin-2-yl)methoxy]-2-methylimidazo[1,2-a]pyridin-3-yl}phenyl)acetamide

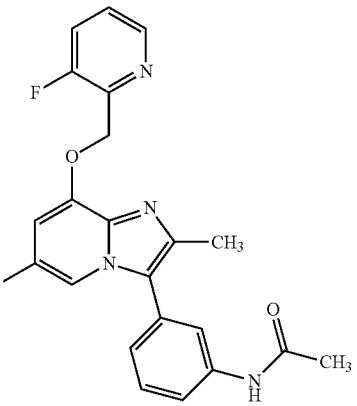

Under argon, 17 mg (0.09 mmol) of (3-acetamidophenyl)boric acid, 65 mg (0.31 mmol) of potassium phosphate and 5.2 mg (0.01 mmol) of bis(tri-tert-butylphosphine)palladium (0) were added in succession to 40 mg (0.10 mmol) of 3-bromo-6-chloro-8-[(3-fluoropyridin-2-yl)methoxy]-2-methylimidazo[1,2-a]pyridine (Example 43A) in a mixture of 0.75 ml of ethanol, 0.37 ml of water and 0.37 ml of toluene. The suspension was degassed with argon and then stirred at 100° C. for 30 min. After the reaction had ended, the reaction mixture was taken up in ethyl acetate/water and extracted. The aqueous phase was extracted twice with ethyl acetate. The combined organic phases were dried over sodium sulfate, filtered and concentrated by rotary evaporation. The residue was purified by preparative HPLC (RP18 column, mobile phase: acetonitrile/water gradient with addition of 0.1% TFA). The product fractions were concentrated and purified by thick-layer chromatography (mobile phase: dichloromethane/methanol=10/1). The product fractions were dissolved in dichloromethane and washed twice with saturated aqueous sodium bicarbonate solution. The combined aqueous phases were extracted twice with dichloromethane. The combined organic phases were dried over sodium sulfate, filtered and concentrated. This gave 3 mg of the target compound (6% of theory).

LC-MS (Method 1): $R_t$=0.71 min

MS (ESpos): m/z=425 (M+H)$^+$

B. ASSESSMENT OF PHARMACOLOGICAL EFFICACY

The following abbreviations are used:
ATP adenosine triphosphate
Brij 35 polyoxyethylene(23) lauryl ether
BSA bovine serum albumin
DTT dithiothreitol
TEA triethanolamine The pharmacological action of the compounds of the invention can be demonstrated in the following assays:

B-1. Measurement of sGC Enzyme Activity by Means of PPi Detection

Soluble guanylyl cyclase (sGC) converts GTP to cGMP and pyrophosphate (PPi) when stimulated. PPi is detected with the aid of the method described in WO 2008/061626. The signal that arises in the assay increases as the reaction progresses and serves as a measure of the sGC enzyme activity. With the aid of a PPi reference curve, the enzyme can be characterized in a known manner, for example in terms of conversion rate, stimulability or Michaelis constant.

Conduct of the Test

To conduct the test, 29 µl of enzyme solution (0-10 nM soluble guanylyl cyclase (prepared according to Honicka et al., Journal of Molecular Medicine 77 (1999) 14-23), in 50 mM TEA, 2 mM magnesium chloride, 0.1% BSA (fraction V), 0.005% Brij 35, pH 7.5) were initially charged in the microplate, and 1 µl of the stimulator solution (0-10 µM 3-morpholinosydnonimine, SIN-1, Merck in DMSO) was added. The microplate was incubated at RT for 10 min. Then 20 µl of detection mix (1.2 nM Firefly Luciferase (*Photinus pyralis* luciferase, Promega), 29 µM dehydroluciferin (prepared according to Bitler & McElroy, Arch. Biochem. Biophys. 72 (1957) 358), 122 µM luciferin (Promega), 153 µM ATP (Sigma) and 0.4 mM DTT (Sigma) in 50 mM TEA, 2 mM magnesium chloride, 0.1% BSA (fraction V), 0.005% Brij 35, pH 7.5) were added. The enzyme reaction was started by adding 20 µl of substrate solution (1.25 mM guanosine 5'-triphosphate (Sigma) in 50 mM TEA, 2 mM magnesium chloride, 0.1% BSA (fraction V), 0.005% Brij 35, pH 7.5) and analysed continuously in a luminometer.

B-2. Effect on a Recombinant Guanylate Cyclase Reporter Cell Line

The cellular activity of the compounds according to the invention is determined using a recombinant guanylate cyclase reporter cell line, as described in F. Wunder et al., *Anal. Biochem.* 339, 104-112 (2005).

Representative MEC values (MEC=minimum effective concentration) for the compounds of the invention are shown in the table below (in some cases as mean values from individual determinations):

TABLE A

| Example No. | MEC [µM] |
|---|---|
| 1 | 0.1 |
| 2 | 0.1 |
| 3 | 0.2 |
| 4 | 1.0 |
| 5 | 3.0 |
| 6 | 10 |
| 7 | 0.3 |
| 8 | 0.3 |
| 9 | 0.3 |
| 10 | 0.1 |
| 11 | 0.3 |
| 12 | 1.0 |
| 13 | 0.2 |
| 14 | 6.5 |
| 15 | 0.02 |
| 16 | 3.0 |
| 19 | 0.2 |
| 20 | 0.3 |

B-3. Vasorelaxant Effect In Vitro

Rabbits are stunned by a blow to the neck and exsanguinated. The aorta is removed, freed from adhering tissue and divided into rings of width 1.5 mm, which are placed individually under prestress into 5 ml organ baths with carbogen-sparged Krebs-Henseleit solution at 37° C. having the following composition (each in mM): sodium chloride: 119; potassium chloride: 4.8; calcium chloride dihydrate: 1; magnesium sulfate heptahydrate: 1.4; potassium dihydrogenphosphate: 1.2; sodium bicarbonate: 25; glucose: 10. The contractile force is determined with Statham UC2 cells, amplified and digitalized using A/D transducers (DAS-1802 HC, Keithley Instruments Munich), and recorded in parallel on linear recorders. To generate a contraction, phenylephrine is added to the bath cumulatively in increasing concentration. After several control cycles, the substance to be studied is added in increasing dosage each time in every further run, and the magnitude of the contraction is compared with the magnitude of the contraction attained in the last preceding run. This is used to calculate the concentration needed to reduce the magnitude of the control value by 50% ($IC_{50}$ value). The standard administration volume is 5 µl; the DMSO content in the bath solution corresponds to 0.1%.

B-4. Blood Pressure Measurement on Anaesthetized Rats

Male Wistar rats having a body weight of 300-350 g are anaesthetized with thiopental (100 mg/kg i.p.). After tracheotomy, a catheter is introduced into the femoral artery to measure the blood pressure. The substances to be tested are administered as solutions, either orally by means of a gavage or intravenously via the femoral vein (Stasch et al. Br. J. Pharmacol. 2002; 135: 344-355).

B-5. Radiotelemetry Measurement of Blood Pressure in Conscious, Spontaneously Hypertensive Rats A commercially available telemetry system from DATA SCIENCES INTERNATIONAL DSI, USA, is employed for the blood pressure measurement on conscious rats described below.

The system consists of 3 main components:
implantable transmitters (Physiotel® telemetry transmitter) receivers (Physiotel® receiver) which are linked via a multiplexer (DSI Data Exchange Matrix) to a
data acquisition computer.

The telemetry system makes it possible to continuously record blood pressure, heart rate and body motion of conscious animals in their usual habitat.

Animal Material

The studies are conducted on adult female spontaneously hypertensive rats (SHR Okamoto) with a body weight of >200 g. SHR/NCrl from the Okamoto Kyoto School of Medicine, 1963, were a cross of male Wistar Kyoto rats having greatly elevated blood pressure and female rats having slightly elevated blood pressure, and were handed over at F13 to the U.S. National Institutes of Health.

After transmitter implantation, the experimental animals are housed singly in type 3 Makrolon cages. They have free access to standard feed and water.

The day/night rhythm in the experimental laboratory is changed by the room lighting at 6:00 am and at 7:00 pm.

Transmitter Implantation

The TA11 PA-C40 telemetry transmitters used are surgically implanted under aseptic conditions in the experimental animals at least 14 days before the first experimental use. The animals instrumented in this way can be used repeatedly after the wound has healed and the implant has settled.

For the implantation, the fasted animals are anaesthetized with pentobarbital (Nembutal, Sanofi: 50 mg/kg i.p.) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (Vet-BonD™, 3M). The transmitter housing is fixed intraperitoneally to the abdominal wall muscle, and the wound is closed layer by layer.

An antibiotic (Tardomyocel COMP, Bayer, 1 ml/kg s.c.) is administered postoperatively for prophylaxis of infection.

Substances and Solutions

Unless stated otherwise, the substances to be studied are administered orally by gavage to a group of animals in each case (n=6). In accordance with an administration volume of 5 ml/kg of body weight, the test substances are dissolved in suitable solvent mixtures or suspended in 0.5% tylose.

A solvent-treated group of animals is used as control.

Experimental Procedure

The telemetry measuring unit present is configured for 24 animals. Each experiment is recorded under an experiment number (Vyear month day).

Each of the instrumented rats living in the system is assigned a separate receiving antenna (1010 Receiver, DSI).

The implanted transmitters can be activated externally by means of an incorporated magnetic switch. They are switched to transmission in the run-up to the experiment. The signals emitted can be detected online by a data acquisition system (Dataquest™ A.R.T. for WINDOWS, DSI) and processed accordingly. The data are stored in each case in a file created for this purpose and bearing the experiment number.

In the standard procedure, the following are measured for 10-second periods in each case:
systolic blood pressure (SBP)
diastolic blood pressure (DBP)
mean arterial pressure (MAP)
heart rate (HR)
activity (ACT).

The acquisition of measurements is repeated under computer control at 5-minute intervals. The source data obtained as absolute values are corrected in the diagram with the currently measured barometric pressure (Ambient Pressure Reference Monitor; APR-1) and stored as individual data. Further technical details are given in the extensive documentation from the manufacturer company (DSI).

Unless indicated otherwise, the test substances are administered at 9:00 am on the day of the experiment. Following the administration, the parameters described above are measured over 24 hours.

Evaluation

After the end of the experiment, the acquired individual data are sorted using the analysis software (DATAQUEST™ A.R.T.™ ANALYSIS). The blank value is assumed here to be the time 2 hours before administration, and so the selected data set encompasses the period from 7:00 am on the day of the experiment to 9:00 am on the following day.

The data are smoothed over a predefinable period by determination of the average (15-minute average) and transferred as a text file to a storage medium. The measured values presorted and compressed in this way are transferred to Excel templates and tabulated. For each day of the experiment, the data obtained are stored in a dedicated file bearing the number of the experiment. Results and test protocols are stored in files in paper form sorted by numbers.

Literature

Klaus Witte, Kai Hu, Johanna Swiatek, Claudia Miissig, Georg Ertl and Björn Lemmer: Experimental heart failure in rats: effects on cardiovascular circadian rhythms and on myocardial β-adrenergic signaling. Cardiovasc Res 47 (2): 203-405, 2000; Kozo Okamoto: Spontaneous hypertension in rats. Int Rev Exp Pathol 7: 227-270, 1969; Maarten van den Buuse: Circadian Rhythms of Blood Pressure, Heart Rate, and Locomotor Activity in Spontaneously Hypertensive Rats as Measured With Radio-Telemetry. Physiology & Behavior 55(4): 783-787, 1994.

B-6. Determination of Pharmacokinetic Parameters Following Intravenous and Oral Administration The pharmacokinetic parameters of the compounds according to the invention are determined in male CD-1 mice, male Wistar rats and female beagles. Intravenous administration in the case of mice and rats is carried out by means of a species-specific plasma/DMSO formulation, and in the case of dogs by means of a water/PEG400/ethanol formulation. In all species, oral administration of the dissolved substance is performed via gavage, based on a water/PEG400/ethanol formulation. The removal of blood from rats is simplified by inserting a silicone catheter into the right *Vena jugularis externa* prior to substance administration. The operation is carried out at least one day prior to the experiment with isofluran anaesthesia and administration of an analgesic (atropine/rimadyl (3/1) 0.1 ml s.c.). The blood is taken (generally more than 10 time points) within a time window including terminal time points of at least 24 to a maximum of 72 hours after substance administration. The blood is removed into heparinized tubes. The blood plasma is then obtained by centrifugation; if required, it is stored at −20° C. until further processing.

An internal standard (which may also be a chemically unrelated substance) is added to the samples of the compounds of the invention, calibration samples and qualifiers, and there follows protein precipitation by means of acetonitrile in excess. Addition of a buffer solution matched to the LC conditions, and subsequent vortexing, is followed by centrifugation at 1000 g. The supernatant is analysed by LC-MS/MS using C18 reversed-phase columns and variable mobile phase mixtures. The substances are quantified via the peak heights or areas from extracted ion chromatograms of specific selected ion monitoring experiments.

The plasma concentration/time plots determined are used to calculate the pharmacokinetic parameters such as AUC, $C_{max}$, $t_{1/2}$ (terminal half-life), F (bioavailability), MRT (mean residence time) and CL (clearance), by means of a validated pharmacokinetic calculation program.

Since the substance quantification is performed in plasma, it is necessary to determine the blood/plasma distribution of the substance in order to be able to adjust the pharmacokinetic parameters correspondingly. For this purpose, a defined amount of substance is incubated in heparinized whole blood of the species in question in a rocking roller mixer for 20 min. After centrifugation at 1000 g, the plasma concentration is measured (by means of LC-MS/MS; see above) and determined by calculating the ratio of the $C_{blood}$/$C_{plasma}$ value.

B-7. Metabolic Study

To determine the metabolic profile of the inventive compounds, they are incubated with recombinant human cytochrome P450 (CYP) enzymes, liver microsomes or primary fresh hepatocytes from various animal species (e.g. rats, dogs), and also of human origin, in order to obtain and to compare information about a very substantially complete hepatic phase I and phase II metabolism, and about the enzymes involved in the metabolism. The compounds of the invention were incubated with a concentration of about 0.1-10 µM. To this end, stock solutions of the compounds of the invention having a concentration of 0.01-1 mM in acetonitrile were prepared, and then pipetted with a 1:100 dilution into the incubation mixture. The liver microsomes and recombinant enzymes were incubated at 37° C. in 50 mM potassium phosphate buffer pH 7.4 with and without NADPH-generating system consisting of 1 mM $NADP^+$, 10 mM glucose-6-phosphate and 1 unit glucose-6-phosphate dehydrogenase. Primary hepatocytes were incubated in suspension in Williams E medium, likewise at 37° C. After an incubation time of 0-4 h, the incubation mixtures were stopped with acetonitrile (final concentration about 30%)

and the protein was centrifuged off at about 15 000×g. The samples thus stopped were either analyzed directly or stored at −20° C. until analysis.

The analysis is carried out by high-performance liquid chromatography with ultraviolet and mass spectrometry detection (HPLC-UV-MS/MS). To this end, the supernatants of the incubation samples are chromatographed with suitable C18 reversed-phase columns and variable mobile phase mixtures of acetonitrile and 10 mM aqueous ammonium formate solution or 0.05% formic acid. The UV chromatograms in conjunction with mass spectrometry data serve for identification, structural elucidation and quantitative estimation of the metabolites, and for quantitative metabolic reduction of the compound of the invention in the incubation mixtures.

B-8. Caco-2 Permeability Test

The permeability of a test substance was determined with the aid of the Caco-2 cell line, an established in vitro model for permeability prediction at the gastrointestinal barrier (Artursson, P. and Karlsson, J. (1991). Correlation between oral drug absorption in humans and apparent drug permeability coefficients in human intestinal epithelial (Caco-2) cells. Biochem. Biophys. 175 (3), 880-885). The Caco-2 cells (ACC No. 169, DSMZ, Deutsche Sammlung von Mikroorganismen und Zellkulturen, Braunschweig, Germany) were sown in 24-well plates having an insert and cultivated for 14 to 16 days. For the permeability studies, the test substance was dissolved in DMSO and diluted to the final test concentration with transport buffer (Hanks Buffered Salt Solution, Gibco/Invitrogen, with 19.9 mM glucose and 9.8 mM HEPES). In order to determine the apical to basolateral permeability ($P_{app}$A-B) of the test substance, the solution comprising the test substance was applied to the apical side of the Caco-2 cell monolayer, and transport buffer to the basolateral side. In order to determine the basolateral to apical permeability ($P_{app}$B-A) of the test substance, the solution comprising the test substance was applied to the basolateral side of the Caco-2 cell monolayer, and transport buffer to the apical side. At the start of the experiment, samples were taken from the respective donor compartment in order to ensure the mass balance. After an incubation time of two hours at 37° C., samples were taken from the two compartments. The samples were analyzed by means of LC-MS/MS and the apparent permeability coefficients ($P_{app}$) were calculated. For each cell monolayer, the permeability of Lucifer Yellow was determined to ensure cell layer integrity. In each test run, the permeability of atenolol (marker for low permeability) and sulfasalazine (marker for active excretion) was also determined as quality control.

B-9. hERG Potassium Current Assay

The hERG (human ether-a-go-go related gene) potassium current makes a significant contribution to the repolarization of the human cardiac action potential (Scheel et al., 2011). Inhibition of this current by pharmaceuticals can in rare cases cause potentially lethal cardiac arrhythmias, and is therefore studied at an early stage during drug development.

The functional hERG assay used here is based on a recombinant HEK293 cell line which stably expresses the KCNH2(HERG) gene (Zhou et al., 1998). These cells are studied by means of the "whole-cell voltage-clamp" technique (Hamill et al., 1981) in an automated system (Patchliner™; Nanion, Munich, Germany), which controls the membrane voltage and measures the hERG potassium current at room temperature. The PatchControlHT™ software (Nanion) controls the Patchliner system, data capture and data analysis. The voltage is controlled by 2 EPC-10 quadro amplifiers controlled by the PatchMasterPro™ software (both: HEKA Elektronik, Lambrecht, Germany). NPC-16 chips with moderate resistance (~2 MΩ; Nanion) serve as the planar substrate for the voltage clamp experiments.

NPC-16 chips are filled with intra- and extracellular solution (cf. Himmel, 2007) and with cell suspension. After forming a gigaohm seal and establishing whole-cell mode (including several automated quality control steps), the cell membrane is clamped at the −80 mV holding potential. The subsequent voltage clamp protocol changes the command voltage to +20 mV (for 1000 ms), −120 mV (for 500 ms), and back to the −80 mV holding potential; this is repeated every 12 s. After an initial stabilization phase (about 5-6 minutes), test substance solution is introduced by pipette in rising concentrations (e.g. 0.1, 1, and 10 mol/l) (exposure about 5-6 minutes per concentration), followed by several washing steps.

The amplitude of the inward "tail" current which is generated by a change in potential from +20 mV to −120 mV serves to quantify the hERG potassium current, and is described as a function of time (IgorPro™ Software). The current amplitude at the end of various time intervals (for example stabilization phase before test substance, first/second/third concentration of test substance) serves to establish a concentration/effect curve, from which the half-maximum inhibiting concentration $IC_{50}$ of the test substance is calculated.

Hamill O P, Marty A, Neher E, Sakmann B, Sigworth F J. Improved patch-clamp techniques for high-resolution current recording from cells and cell-free membrane patches. Pfluegers Arch 1981; 391:85-100.

Himmel H M. Suitability of commonly used excipients for electrophysiological in-vitro safety pharmacology assessment of effects on hERG potassium current and on rabbit Purkinje fiber action potential. J Phannacol Toxicol Methods 2007; 56:145-158.

Scheel O, Himmel H, Rascher-Eggstein G, Knott T. Introduction of a modular automated voltage-clamp platform and its correlation with manual human ether-a-go-go related gene voltage-clamp data. Assay Drug Dev Technol 2011; 9:600-607.

Zhou Z F, Gong Q, Ye B, Fan Z, Makielski J C, Robertson G A, January C T. Properties of hERG channels stably expressed in HEK293 cells studied at physiological temperature. Biophys J 1998; 74:230-241.

C. WORKING EXAMPLES OF PHARMACEUTICAL COMPOSITIONS

The compounds of the invention can be converted to pharmaceutical preparations as follows:

Tablet:

Composition:

100 mg of the compound of the invention, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm.

Production:

The mixture of compound of the invention, lactose and starch is granulated with a 5% solution (w/w) of the PVP in water. The granules are dried and then mixed with the magnesium stearate for 5 minutes. This mixture is compressed using a conventional tableting press (see above for format of the tablet). The guide value used for the pressing is a pressing force of 15 kN.

Suspension for Oral Administration:
Composition:
1000 mg of the compound of the invention, 1000 mg of ethanol (96%), 400 mg of Rhodigel® (xanthan gum from FMC, Pennsylvania, USA) and 99 g of water.
10 ml of oral suspension correspond to a single dose of 100 mg of the compound of the invention.
Production:
The Rhodigel is suspended in ethanol; the compound of the invention is added to the suspension. The water is added while stirring. The mixture is stirred for about 6 h until the swelling of the Rhodigel is complete.
Solution for Oral Administration:
Composition:
500 mg of the compound of the invention, 2.5 g of polysorbate and 97 g of polyethylene glycol 400. 20 g of oral solution correspond to a single dose of 100 mg of the compound of the invention.
Production:
The compound of the invention is suspended in the mixture of polyethylene glycol and polysorbate with stirring. The stirring operation is continued until dissolution of the compound of the invention is complete.
i.v. solution:
The compound of the invention is dissolved in a concentration below the saturation solubility in a physiologically acceptable solvent (e.g. isotonic saline solution, glucose solution 5% and/or PEG 400 solution 30%). The resulting solution is subjected to sterile filtration and dispensed into sterile and pyrogen-free injection vessels.

The invention claimed is:
1. A compound of the formula (I)

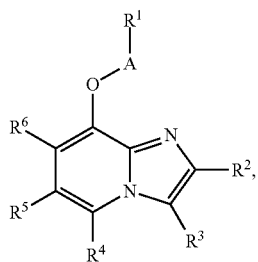

(I)

in which
A represents $CH_2$, $CD_2$ or $CH(CH_3)$,
$R^1$ represents $(C_3-C_7)$-cycloalkyl, phenyl or pyridyl,
  where $(C_3-C_7)$-cycloalkyl may be substituted by 1 to 4 substituents independently of one another selected from the group consisting of fluorine, trifluoromethyl and $(C_1-C_4)$- alkyl,
  where phenyl is substituted by 1 to 4 substituents independently of one another selected from the group consisting of halogen, cyano, monofluoromethyl, difluoromethyl, trifluoromethyl, $(C_1-C_4)$-alkyl, $(C_1-C_4)$-alkoxy and difluoromethoxy
  and
  where pyridyl is substituted by 1 or 2 substituents independently of one another selected from the group consisting of halogen, cyano and $(C_1-C_4)$-alkyl,
$R^2$ represents $(C_1-C_4)$-alkyl, cyclopropyl, cyclobutyl, monofluoromethyl, difluoromethyl or trifluoromethyl,
$R^3$ represents 6-membered heteroaryl,
  where 6-membered heteroaryl is up to disubstituted by —$NR^9R^{10}$,
  in which
  $R^9$ represents hydrogen or $(C_1-C_4)$-alkyl,
  $R^{10}$ represents hydrogen, $(C_1-C_6)$-alkyl, phenyl or $(C_1-C_4)$-alkylcarbonyl,
    in which $(C_1-C_6)$-alkyl may be substituted by 1 or 2 substituents independently of one another selected from the group consisting of $(C_1-C_4)$-alkoxy, amino and phenyl, and up to pentasubstituted by fluorine,
  or
  $R^9$ and $R^{10}$ together with the nitrogen atom to which they are attached form a 4- to 6-membered heterocycle,
    in which the 4- to 6-membered heterocycle may be substituted by 1 or 2 $(C_1-C_4)$-alkyl substituents,
  where 6-membered heteroaryl may be substituted by 1 or 2 substituents independently of one another selected from the group consisting of fluorine, chlorine, bromine, cyclopropyl, methyl and ethyl,
$R^4$ represents hydrogen,
$R^5$ represents hydrogen, fluorine, chlorine, cyano, $(C_1-C_4)$-alkyl, cyclopropyl, difluoromethyl or trifluoromethyl,
$R^6$ represents hydrogen or fluorine,
and the N-oxides, salts, and salts of the N-oxides thereof.
2. The compound of the formula (I) as claimed in claim 1 in which
A represents $CH_2$,
$R^1$ represents cyclohexyl, phenyl or pyridyl,
  where phenyl is substituted by 1 to 4 substituents independently of one another selected from the group consisting of fluorine, chlorine, cyano and methyl,
  and
  where pyridyl is substituted by 1 or 2 fluorine substituents,
$R^2$ represents methyl, cyclopropyl or trifluoromethyl,
$R^3$ represents 3-pyridyl, 4-pyridyl, 2-pyrimidyl, 5-pyrimidyl or 1,3,5-triazinyl,
  where 3-pyridyl, 4-pyridyl, 2-pyrimidyl and 5-pyrimidyl are substituted by —$NR^9R^{10}$,
  in which
  $R^9$ represents hydrogen or methyl,
  $R^{10}$ represents $(C_1-C_6)$-alkyl or phenyl,
    in which $(C_1-C_6)$-alkyl may be substituted by 1 or 2 substituents independently of one another selected from the group consisting of $(C_1-C_4)$-alkoxy, amino and phenyl, and up to trisubstituted by fluorine,
  or
  $R^9$ and $R^{10}$ together with the nitrogen atom to which they are attached form a 5- or 6-membered heterocycle,
    in which the 5- or 6-membered heterocycle may be substituted by 1 or 2 methyl substituents,
  where 3-pyridyl, 4-pyridyl, 2-pyrimidyl and 5-pyrimidyl may be substituted by 1 or 2 substituents independently of one another selected from the group consisting of fluorine, chlorine and methyl,
  where 1,3,5-triazinyl is up to disubstituted by —$NR^{9A}R^{10A}$,
  in which
  $R^{9A}$ represents hydrogen or methyl,
  $R^{10A}$ represents hydrogen, $(C_1-C_6)$-alkyl or phenyl, in which $(C_1-C_6)$-alkyl may be substituted by amino and up to three times by fluorine,
or
$R^{9A}$ and $R^{10A}$ together with the nitrogen atom to which they are attached form a 5- or 6-membered heterocycle,
in which the 5- or 6-membered heterocycle may be substituted by 1 or 2 methyl substituents,
where 1,3,5-triazinyl may be substituted by chlorine,
$R^4$ represents hydrogen,
$R^5$ represents hydrogen, chlorine, methyl or cyclopropyl,
$R^6$ represents hydrogen,
and the N-oxides, salts, and salts of the N-oxides thereof.

3. The compound of the formula (I) as claimed in claim 1 in which
A represents $CH_2$,
$R^1$ represents cyclohexyl, phenyl or pyridyl,
where phenyl is substituted by 1 to 3 fluorine substituents,
where pyridyl is substituted by 1 fluorine substituent,
$R^2$ represents methyl,
$R^3$ represents 3-pyridyl, 4-pyridyl, 2-pyrimidyl, 5-pyrimidyl or 1,3,5-triazinyl,
where 3-pyridyl, 4-pyridyl, 2-pyrimidyl and 5-pyrimidyl are substituted by $-NR^9R^{10}$,
in which
$R^9$ represents hydrogen or methyl,
$R^{10}$ represents $(C_1-C_6)$-alkyl or phenyl,
in which $(C_1-C_6)$-alkyl may be substituted by 1 or 2 substituents independently of one another selected from the group consisting of $(C_1-C_4)$-alkoxy, amino and phenyl, and up to trisubstituted by fluorine,
or
$R^9$ and $R^{10}$ together with the nitrogen atom to which they are attached form a 5- or 6-membered heterocycle,
in which the 5- or 6-membered heterocycle may be substituted by 1 or 2 methyl substituents,
where 3-pyridyl, 4-pyridyl, 2-pyrimidyl and 5-pyrimidyl may be substituted by 1 or 2 substituents independently of one another selected from the group consisting of fluorine, chlorine and methyl,
where 1,3,5-triazinyl is up to disubstituted by $-NR^{9A}R^{10A}$,
in which
$R^{9A}$ represents hydrogen or methyl,
$R^{10A}$ represents hydrogen, $(C_1-C_6)$-alkyl or phenyl,
in which $(C_1-C_6)$-alkyl may be substituted by amino and up to three times by fluorine,
where 1,3,5-triazinyl may be substituted by chlorine,
$R^4$ represents hydrogen,
$R^5$ represents hydrogen, chlorine, methyl or cyclopropyl,
$R^6$ represents hydrogen,
and the N-oxides, salts, and salts of the N-oxides thereof.

4. The compound of the formula (I) as claimed in claim 1, in which
A represents $CH_2$,
$R^1$ represents cyclohexyl,
or
represents a phenyl group of the formula

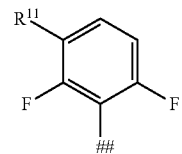

where
represents the point of attachment to A,
and
$R^{11}$ represents hydrogen or fluorine,
or
represents a pyridyl group of the formula

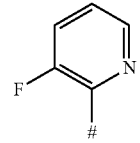

where
represents the point of attachment to A,
$R^2$ represents methyl,
$R^3$ represents 3-pyridyl, 4-pyridyl, 2-pyrimidyl, 5-pyrimidyl or 1,3,5-triazinyl,
where 3-pyridyl is substituted in the 4-position by $-NR^9R^{10}$,
where 4-pyridyl is substituted in the 3-position by $-NR^9R^{10}$,
where 2-pyrimidyl is substituted in the 4-position by $-NR^9R^{10}$,
where 5-pyrimidyl is substituted in the 2-position by $-NR^9R^{10}$,
in which in each case
$R^9$ represents hydrogen or methyl,
$R^{10}$ represents $(C_1-C_6)$-alkyl or phenyl,
in which $(C_1-C_6)$-alkyl may be substituted by 1 or 2 substituents independently of one another selected from the group consisting of $(C_1-C_4)$-alkoxy, amino and phenyl, and up to trisubstituted by fluorine,
or
$R^9$ and $R^{10}$ together with the nitrogen atom to which they are attached form a pyrrolidinyl, morpholinyl or piperazinyl ring,
in which the pyrrolidinyl, morpholinyl or piperazinyl ring may be substituted by 1 or 2 methyl substituents,
where 4-pyridyl may be substituted in the 2-position by fluorine,
where 1,3,5-triazinyl is up to disubstituted by $-NR^{9A}R^{10A}$,
in which
$R^{9A}$ represents hydrogen or methyl,
$R^{10A}$ represents hydrogen, $(C_1-C_6)$-alkyl or phenyl,
in which $(C_1-C_6)$-alkyl may be substituted by amino and up to three times by fluorine,
where 1,3,5-triazinyl may be substituted by chlorine,
$R^4$ represents hydrogen,
$R^5$ represents hydrogen, chlorine or methyl,
$R^6$ represents hydrogen,
and the N-oxides, salts, and salts of the N-oxides thereof.

5. A medicament comprising the compound of the formula (I) as defined in claim 1 in combination with an inert, non-toxic, pharmaceutically suitable excipient.

6. A medicament comprising the compound of the formula (I) as defined in claim 1 in combination with a further active compound selected from the group consisting of organic nitrates, NO donors, cGMP-PDE inhibitors, antithrombotic agents, hypotensive agents and lipid metabolism modifiers.

* * * * *